United States Patent [19]
Kawamoto et al.

[11] Patent Number: 5,977,097
[45] Date of Patent: Nov. 2, 1999

[54] 1-METHYLCARBAPENEM DERIVATIVES

[75] Inventors: Isao Kawamoto; Katsuya Ishikawa, both of Tokyo; Katsuhiko Kojima, Yono; Yasuo Shimoji; Satoshi Ohya, both of Tokyo; Munetsugu Morimoto, Hikone, all of Japan

[73] Assignee: Sankyo Company Limited, Tokyo, Japan

[21] Appl. No.: 09/176,804

[22] Filed: Oct. 22, 1998

Related U.S. Application Data

[63] Continuation of application No. PCT/JP97/01452, Apr. 25, 1997.

[30] Foreign Application Priority Data

Apr. 26, 1996 [JP] Japan ..................... 8-107364

[51] Int. Cl.⁶ .................. A61K 31/40; C07D 487/04
[52] U.S. Cl. ........................... 514/210; 540/350
[58] Field of Search .............. 540/350; 514/210

[56] References Cited

U.S. PATENT DOCUMENTS

| | | | |
|---|---|---|---|
| 5,122,604 | 6/1992 | Sunagawa et al. | 540/350 |
| 5,712,267 | 1/1998 | Kawamoto et al. | 514/210 |

FOREIGN PATENT DOCUMENTS

| | | |
|---|---|---|
| 0 337 637 | 10/1989 | European Pat. Off. |
| 0 443 883 | 8/1991 | European Pat. Off. |
| 518558 | 12/1992 | European Pat. Off. |
| 0 560 613 | 9/1993 | European Pat. Off. |
| 2-28180 | 1/1990 | Japan. |
| 2-3687 | 1/1990 | Japan. |
| 4-211083 | 8/1992 | Japan. |
| 5-310740 | 11/1993 | Japan. |
| 5-339269 | 12/1993 | Japan. |
| 6-172356 | 6/1994 | Japan. |
| 6-199860 | 7/1994 | Japan. |
| 7-48375 | 2/1995 | Japan. |
| 7-228570 | 8/1995 | Japan. |
| 8-48667 | 2/1996 | Japan. |

OTHER PUBLICATIONS

Kropp et al "Metabolism of Thienamycin and Related Carbapenem Antibiotics by the Renal Dipeptidase, Dehydropeptidase–1", Antimicrobial Agents and Chemotherapy, vol. 22, No. 1, pp. 62–70 (1982).

Norrby et al "Urinary Recovery of N–Formimidoyl Thienamycin (MK0787) as Affected by Coadministration of N–Formimidoyl Thienamycin Dehydropeptidase Inhibitors", Antimicrobial Agents and Chemotherapy, vol. 23, No. 2, pp. 300–307 (1983).

Kawamoto et al "A Convenient Synthesis of Versatile Side–chain Intermediates for Carbapenem Antiobiotics", Synlett, pp. 575–577 (1995).

*Primary Examiner*—Mukund J. Shah
*Assistant Examiner*—Brenda Coleman
*Attorney, Agent, or Firm*—Frishauf, Holtz, Goodman, Langer & Chick, P.C.

[57] ABSTRACT

A 1-methylcarbapenem compound represented by the following formula:

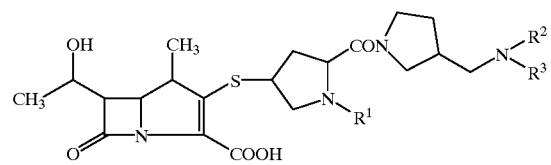

(I)

[wherein $R^1$ represents a hydrogen atom or a lower alkyl group, $R^2$ represents a hydrogen atom or a lower alkyl group, $R^3$ represents a hydrogen atom, a lower alkyl group, a lower alkyl group which has a substituent, a cycloalkyl group or a group of formula —C(=NH)$R^4$ (in which $R^4$ represents a hydrogen atom, a lower alkyl group or an amino group)]; or a pharmacologically acceptable salt or derivative thereof. The 1-methylcarbapenem compounds of the present invention exhibit excellent antibacterial activity and are therefore effective as a preventive or remedy of infections.

9 Claims, No Drawings

1-METHYLCARBAPENEM DERIVATIVES

This application is a continuation application of International Application PCT/JP97/01452 filed Apr. 25, 1997.

TECHNICAL FIELD

The present invention relates to 1-methylcarbapenem compounds having excellent antibacterial activity, pharmacologically acceptable salts or derivatives thereof; compositions for the prevention or treatment of bacterial infections which comprise any one of said compounds, salts and derivatives as an effective ingredient; use of said compounds, salts or derivatives for the preparation of a medicament used for the prevention or treatment of bacterial infections; a method for the prevention or treatment of bacterial infections which comprises administering a pharmacologically effective amount of any one of said compounds, salts and derivatives to warm-blooded animals, and processes for the preparation of said compounds, salts or derivatives.

BACKGROUND OF THE INVENTION

Thienamycin derivatives which are carbapenem antibiotics have excellent antibacterial activity, but they have poor chemical stability and tend to lose their activity due to decomposition by dehydropeptidase I, which is an enzyme present in the human body, and exhibit a low recovery rate in urine [in H. Kropp et al., Antimicrob. Agents Chemother., 22, 62 (1982); S. R. Norrby et al., ibid., 23, 300 (1983)]. In addition, they happen to exhibit nephrotoxicity in some kinds of experimental animals. Among the thienamycin derivatives, imipenem has been used as a mixture with cilastatin which is a dehydropeptidase I inhibitor, while panipenem has been put on the market as a mixture with betamipron which is an organic anion transport inhibitor. After that, chemical stability and stability against dehydropeptidase I were found to be improved by introducing a methyl group at the 1-position of the carbapenem skeleton and then a carbapenem derivatives usable as a single active ingredient preparation such as meropenem (U.S. Pat. No. 5,122,604) has been on the market. As 1-methylcarbapenem derivatives such as meropenem have come to be used frequently in the clinical situation, however, resistant strains against it in *Pseudomonas aeruginosa* and the like have started to be recognized.

There is accordingly an increasing need for agents which exhibit stronger and well-balanced antibacterial activity against a wide range of bacteria, including strains of *Pseudomonas aeruginosa* which exhibit resistance against meropenem, and are free from nephrotoxicity. In Japanese Patent Application Kokai No. Hei 5-310740, Japanese Patent Application Kokai No. Hei 5-339269, Japanese Patent Application Kokai No. Hei 6-172356 and Japanese Patent Application Kokai No. Hei 6-199860, 1-methylcarbapenem derivatives synthesized for satisfying the above-described need are disclosed.

DETAILED DESCRIPTION OF THE INVENTION

With a view toward overcoming the above-described defects of 1-methylcarbapenem derivatives, the present inventors carried out investigations. As a result, it has been found that compared with the conventional 1-methylcarbapenem derivatives, compounds (I) of the present invention have superior antibacterial activity, are more stable against dehydropeptidase I, have improved recovery rates in urine and are superior in pharmacokinetics such as half-life in blood. It has also been found that the compounds (I) of the present invention have low nephrotoxicity and are therefore effective as an antibacterial agent used for the treatment or prevention (particularly treatment) of bacterial infections.

In Japanese Patent Application Kokai No. Hei 5-310740, Japanese Patent Application Kokai No. Hei 5-339269 and Japanese Patent Application Kokai No. Hei 6-172356, 3-(aminomethyl)pyrrolidine-containing compounds [a compound represented by the formula (I) wherein $R^1$, $R^2$ and $R^3$ are hydrogen atoms at the same time, and the like] are disclosed, but they do not contain any disclosure about the preparation of compounds which belong to the present invention and have a substituent at the amino part of the 3-(aminomethyl)pyrrolidine group.

The present invention provides 1-methylcarbapenem compounds having excellent antibacterial activity, pharmacologically acceptable salts or derivatives thereof, compositions for the prevention or treatment of bacterial infections which comprise any one of said compounds, salts and derivatives as an effective ingredient; use of said compounds, salts or derivatives for the preparation of a medicament used for the prevention or treatment of bacterial infections; a method for the prevention or treatment of bacterial infections which comprises administering a pharmacologically effective amount of any one of said compounds, salts and derivatives to warm-blooded animals; and processes for the preparation of said compounds, salts or derivatives.

The 1-methylcarbapenem derivatives of the present invention are represented by formula:

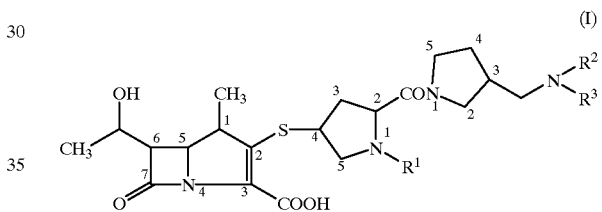

wherein:

$R^1$ represents a hydrogen atom or a lower alkyl group;

$R^2$ represents a hydrogen atom or a lower alkyl group; and $R^3$ represents a hydrogen atom, a lower alkyl group, a lower alkyl group which has 1 to 3 substituents (each of said substituents is a hydroxyl group, a halogen atom, a carbamoyl group, a carbamoyl group substituted by 1 or 2 lower alkyl groups, a carbamoyloxy group, a carbamoyloxy group substituted by 1 or 2 lower alkyl groups, a lower alkoxy group, an amino group or an amino group substituted by 1 or 2 lower alkyl groups), a cycloalkyl group or a group of formula —C(=NH)$R^4$ (in which $R^4$ represents a hydrogen atom, a lower alkyl group or an amino group), or $R^2$ and $R^3$ taken together represent an alkylene group which is optionally interrupted by one oxygen, nitrogen or sulfur atom (said nitrogen atom may be substituted by a lower alkyl group);

with the proviso that $R^1$, $R^2$ and $R^3$ do not represent hydrogen atoms at the same time.

In the above description, the "lower alkyl group" in the definitions of $R^1$, $R^2$, $R^3$ and $R^4$ is a straight or branched $C_{1-4}$ alkyl group. Examples of such a group include methyl, ethyl, n-propyl, isopropyl, n-butyl and t-butyl groups, of which a methyl or ethyl group is preferred, a methyl group being more preferred.

Examples of the "halogen atom" in the definition of $R^3$ include fluorine, chlorine and bromine atoms, of which a fluorine atom is preferred.

Examples of the "carbamoyl group substituted by 1 or 2 lower alkyl groups" in the definition of $R^3$ include methylcarbamoyl, ethylcarbamoyl, dimethylcarbamoyl and diethylcarbamoyl groups, of which a methylcarbamoyl or dimethylcarbamoyl group is preferred.

Examples of the "carbamoyloxy group substituted by 1 or 2 lower alkyl groups" in the definition of $R^3$ include methylcarbamoyloxy, ethylcarbamoyloxy, dimethylcarbamoyloxy and diethylcarbamoyloxy groups, of which a methylcarbamoyloxy or dimethylcarbamoyloxy group is preferred.

Examples of the "amino group substituted by 1 or 2 lower alkyl groups" in the definition of $R^3$ include methylamino, ethylamino, dimethylamino and diethylamino groups, of which a methylamino or dimethylamino group is preferred.

The "lower alkoxy group" in the definition of $R^3$ is a $C_{1-4}$ alkoxy group and examples include methoxy, ethoxy, propoxy and butoxy groups, of which a methoxy group is preferred.

Preferred examples of the "substituent" of the "lower alkyl group having 1 to 3 substituents" in the definition of $R^3$ include a hydroxy group, a fluorine atom, a carbamoyl, methylcarbamoyl, dimethylcarbamoyl, carbamoyloxy, methoxy, amino, methylamino or dimethylamino group.

Examples of the above-described "lower alkyl group having 1 to 3 substituents" include 2-hydroxyethyl, 3-hydroxypropyl, 2-hydroxypropyl, 2,3-dihydroxypropyl, fluoromethyl, difluoromethyl, trifluoromethyl, 2-fluoroethyl, 2,2,2-trifluoroethyl, chloromethyl, dichloromethyl, trichloromethyl, 2-chloroethyl, carbamoylmethyl, N-methylcarbamoylmethyl, N,N-dimethylcarbamoylmethyl, 2-carbamoylethyl, 2-(N-methylcarbamoyl)ethyl, 2-(N,N-dimethylcarbamoyl)ethyl, 2-carbamoyloxyethyl, 2-(N,N-dimethylcarbamoyloxy)ethyl, 2-methoxyethyl, 2-ethoxyethyl, 2-aminoethyl, 3-aminopropyl, 2-aminopropyl, 2-(methylamino)ethyl, 3-(methylamino)propyl, 2-(dimethylamino)ethyl and 3-(dimethylamino)propyl groups; of which a 2-hydroxyethyl, 2-fluoroethyl, 2,2,2-trifluoroethyl, carbamoylmethyl, 2-carbamoylethyl, N-methylcarbamoylmethyl, N,N-dimethylcarbamoylmethyl, 2-methoxyethyl, 2-carbamoyloxyethyl, 2-aminoethyl, 2-(methylamino)ethyl or 2-(dimethylamino)ethyl group is preferred, a 2-hydroxyethyl, carbamoylmethyl, 2-aminoethyl or 2-(methylamino)ethyl group being more preferred.

The "cycloalkyl group" in the definition of $R^3$ is a $C_{3-6}$ cycloalkyl group and examples of such a group includes cyclopropyl, cyclobutyl, cyclopentyl and cyclohexyl groups; of which a cyclopropyl or cyclobutyl group is preferred, a cyclopropyl group being more preferred.

Examples of the "group represented by the formula —C(=NH)R$^4$" include formimidoyl, acetimidoyl, propioimidoyl and amidino groups; of which a formimidoyl, acetimidoyl or amidino group is preferred.

The "alkylene group" of the "alkylene group which is optionally interrupted by one oxygen, nitrogen or sulfur atom" in the definition of the groups of $R^2$ and $R^3$ taken together is a straight or branched $C_{2-6}$ alkylene group and examples of such a group include ethylene, propylene, trimethylene, 1-methyltrimethylene, 2-methyltrimethylene, tetramethylene, 1-methyltetramethylene, 2-methyltetramethylene and pentamethylene groups.

Examples of the alkylene group which is interrupted by one oxygen, nitrogen or sulfur atom include ethyleneoxyethylene ($CH_2CH_2OCH_2CH_2$), ethyleneaminoethylene ($CH_2CH_2NHCH_2CH_2$), ethyleneaminopropylene ($CH_2CH_2NHCH_2CH_2CH_2$) and ethylenethioethylene ($CH_2CH_2SCH_2CH_2$).

The nitrogen atom interrupted in the alkylene group is optionally substituted by a lower alkyl group. The lower alkyl group is a $C_{1-4}$ alkyl group, of which a methyl group is preferred.

Examples of the "alkylene group which is optionally interrupted by one oxygen, nitrogen or sulfur atom" include ethylene, trimethylene, tetramethylene, pentamethylene, ethyleneoxyethyl, ethylenethioethyl, ethyleneaminoethyl, ethyleneaminopropyl, ethylene(methylamino)ethyl, ethylene(ethylamino)ethyl and ethylene(methylamino) propyl groups; of which a trimethylene, tetramethylene, pentamethylene, ethyleneoxyethyl, ethylenethioethyl, ethyleneaminoethyl, ethylene(methyl)aminoethyl or ethyleneaminopropyl group is preferred, a tetramethylene group being more preferred.

Preferred examples of $R^1$ include a hydrogen atom and a $C_{1-4}$ alkyl group; of which a hydrogen atom or a methyl or ethyl group is more preferred, a hydrogen atom or a methyl group being most preferred.

Preferred examples of $R^2$ include a hydrogen atom and a $C_{1-4}$ alkyl group; of which a hydrogen atom or a methyl or ethyl group is more preferred, a hydrogen atom or a methyl group being most preferred.

Preferred examples of $R^3$ include a hydrogen atom, a $C_{1-4}$ alkyl group, a $C_{1-4}$ alkyl group having 1 to 3 substituents (examples of said substituent include a hydroxyl group, halogen atoms, a carbamoyl group, a carbamoyl group substituted with 1 or 2 $C_{1-4}$ alkyl groups, a carbamoyloxy group, a carbamoyloxy group substituted with 1 or 2 $C_{1-4}$ alkyl groups, a $C_{1-4}$ alkoxy group, an amino group and an amino group substituted with 1 or 2 $C_{1-4}$ alkyl groups), a $C_{3-6}$ cycloalkyl group and a group of formula —C(=NHR$^4$) (wherein $R^4$ represents a hydrogen atom, a $C_{1-4}$ alkyl group or an amino group); of which a hydrogen atom or a methyl, ethyl, 2-hydroxyethyl, 2-fluoroethyl, 2,2,2-trifluoroethyl, carbamoylmethyl, 2-carbamoylethyl, N-methylcarbamoylmethyl, N,N-dimethylcarbamoylmethyl, 2-methoxyethyl, 2-carbamoyloxyethyl, 2-aminoethyl, 2-(methylamino)ethyl, 2-(dimethylamino)ethyl, cyclopropyl, formimidoyl, acetimidoyl or amidino group is preferred, a hydrogen atom or a methyl, 2-hydroxyethyl, carbamoylmethyl, 2-aminoethyl, 2-(methylamino)ethyl, cyclopropyl, formimidoyl, acetimidoyl or amidino group being more preferred, and a hydrogen atom or a methyl, formimidoyl, acetimidoyl or amidino group being most preferred.

Preferred examples of the group of $R^2$ and $R^3$ taken together include a $C_{2-6}$ alkylene group which is optionally interrupted by one oxygen, nitrogen or sulfur atom (said nitrogen atom is optionally substituted by a $C_{1-4}$ alkyl group); of which a trimethylene, tetramethylene, pentamethylene, ethyleneoxyethylene, ethylenethioethylene, ethyleneaminoethylene, ethylene (methylamino)ethylene or ethyleneaminopropylene group is preferred, a tetramethylene group being most preferred.

The compound (I) can be converted into its "pharmacologically acceptable salts or derivatives" if necessary.

Examples of the "pharmacologically acceptable salts" include salts of a mineral acid such as hydrochloride, hydrobromide, hydroiodide, phosphate, sulfate and nitrate; sulfonates such as methanesulfonate, ethanesulfonate, benzenesulfonate and p-toluenesulfonate; organic acid salts such as oxalate, tartrate, citrate, maleate, succinate, acetate, benzoate, mandelate, ascorbate, lactate, gluconate and malate; amino acid salts such as glycine salt, lysine salt, arginine salt, ornithine salt, glutamate and aspartate; inorganic salts such as lithium salt, sodium salt, potassium salt, calcium salt and magnesium salt; and salts with an organic base such as ammonium salt, triethylamine salt, diisopropylamine salt and cyclohexylamine salt; of which a hydrochloride, hydrobromide, phosphate, sulfate, methanesulfonate, p-toluenesulfonate, oxalate, tartrate, citrate, acetate, lactate, glutamate, aspartate, sodium salt, potassium salt, ammonium salt or triethylamine salt is preferred, a hydrochloride, sulfate, methanesulfonate, citrate, acetate or lactate being more preferred, and a hydrochloride or sulfate being most preferred.

The compound (I) of the present invention happens to absorb water and form a product with absorbed water or a hydrate when it is left alone in the air, prepared by the lyophilization of its aqueous solution, or recrystallized. Such salts are also included in the present invention.

The "pharmacologically acceptable derivative" is a derivative in which some of the carboxyl, hydroxyl and amino groups or the like of compound (I) are protected by a protecting group (a so-called prodrug-forming group) which may be cleaved in vivo by a chemical or biological method such as hydrolysis to afford the original compound (I) or salt thereof. Whether a derivative is such a derivative or not can be determined by orally or intravenously administering the derivative to an animal such as rat or mouse and studying the body fluid of the animal. If the original compound or a pharmacologically acceptable salt thereof can be detected from the body fluid, the derivative is determined as a prodrug of compound (I). Examples of such a protecting group for the carboxyl, hydroxyl, amino groups or the like include acyloxyalkyl, alkoxycarbonyloxyalkyl, phthalidyl, (2-oxo-1,3-dioxolen-4-yl)alkyl which may have an alkyl or aryl group at the 5-position, acyl, alkoxycarbonyl and aminoacyl groups.

Examples of the acyloxyalkyl group include pivaloyloxymethyl, isobutyryloxymethyl, 1-(isobutyryloxy) ethyl, acetoxymethyl, 1-(acetoxy)ethyl, 1-methylcyclohexylcarbonyloxymethyl, 1-methylcyclopentylcarbonyloxymethyl, 2-ethylbutyryloxymethyl and hexanoyloxymethyl groups; of which a pivaloyloxymethyl, acetoxymethyl or 1-methylcyclohexylcarbonyloxymethyl group is preferred.

Examples of the alkoxycarbonyloxyalkyl group include t-butoxycarbonyloxymethyl, 1-(methoxycarbonyloxy)ethyl, 1-(ethoxycarbonyloxy)ethyl, 1-(isopropoxycarbonyloxy) ethyl, 1-(t-butoxycarbonyloxy)ethyl, 1-(cyclohexylcarbonyloxy)ethyl and 1-(cyclopentylcarbonyloxy)ethyl groups; of which a 1-(isopropoxycarbonyloxy)ethyl or 1-(cyclopentylcarbonyloxy)ethyl group is preferred.

Examples of the 1-(2-oxo-1,3-dioxolen-4-yl)alkyl group which may have an alkyl or an aryl group at the 5-position include 2-oxo-1,3-dioxolen-4-ylmethyl, 1-(2-oxo-1,3-dioxolen-4-yl)ethyl, 5-methyl-2-oxo-1,3-dioxolen-4-ylmethyl, 1-(5-methyl-2-oxo-1,3-dioxolen-4-yl)ethyl, 5-ethyl-2-oxo-1,3-dioxolen-4-ylmethyl, 5-propyl-2-oxo-1,3-dioxolen-4-ylmethyl and 5-phenyl-2-oxo-1,3-dioxolen-4-ylmethyl groups; of which a 5-methyl-2-oxo-1,3-dioxolen-4-ylmethyl group is preferred.

Among the above-exemplified protecting groups, a 5-methyl-2-oxo-1,3-dioxolen-4-ylmethyl, acetoxymethyl, pivaloyloxymethyl, 1-methylcyclohexylcarbonyloxymethyl, 1-(isopropoxycarbonyloxy)ethyl or 1-(cyclohexyloxycarbonyloxy)ethyl group is more preferred and they are preferably used as a protecting group of the carboxyl group to make an ester derivative of compound (I).

The compounds (1) of the present invention include individual isomers and a mixture of the isomers. The preferred example of the isomer is a compound which has an R configuration at the 1-position of the carbapenem skeleton, a (5S,6S) configuration at the 5- and 6-positions similarly to thienamycin, and an R configuration as a hydroxyl-containing -carbon at the substituent of the 6-position.

The (2S,4S) configuration is suited for the 2- and 4-positions of the 2-(substituted pyrrolidine)-4-ylthio group of the substituent at the 2-position of the carbapenem skeleton.

There is no particular limitation on the configuration at the 3-position of the 3-(substituted aminomethyl)pyrrolidin-1-yl group.

Preferred examples of the compound of formula (I) include the compounds wherein:

$R^1$ represents a hydrogen atom or a $C_{1-4}$ alkyl group;

$R^2$ represents a hydrogen atom or a $C_{1-4}$ alkyl group; and $R^3$ represents a hydrogen atom, a $C_{1-4}$ alkyl group, a $C_{1-4}$ alkyl group having 1 to 3 substituents (each of said substituent represents a hydroxyl group, a halogen atom, a carbamoyl group, a carbamoyl group substituted by 1 or 2 $C_{1-4}$ alkyl groups, a carbamoyloxy group, a carbamoyloxy group substituted by 1 or 2 $C_{1-4}$ alkyl groups, a $C_{1-4}$ alkoxy group, an amino group or an amino group substituted by 1 or 2 $C_{1-4}$ alkyl groups), a $C_{3-6}$ cycloalkyl group or a group of formula —C(=NH)$R^4$ (wherein $R^4$ represents a hydrogen atom, a $C_{1-4}$ alkyl group or an amino group), or $R^2$ and $R^3$ taken together represent a $C_{2-6}$ alkylene group which is optionally interrupted by one oxygen, nitrogen or sulfur atom (said nitrogen atom may be substituted by the $C_{1-4}$ alkyl group).

More preferred examples include compounds wherein:

$R^1$ represents a hydrogen atom or a methyl or ethyl group;

$R^2$ represents a hydrogen atom or a methyl or ethyl group; and $R^3$ represents a hydrogen atom or a methyl, ethyl, 2-hydroxyethyl, 2-fluoroethyl, 2,2,2-trifluoroethyl, carbamoylmethyl, 2-carbamoylethyl, N-methylcarbamoylmethyl, N,N-dimethylcarbamoylmethyl, 2-methoxyethyl, 2-carbamoyloxyethyl, 2-aminoethyl, 2-(methylamino) ethyl, 2-(dimethylamino)ethyl, cyclopropyl, formimidoyl, acetimidoyl or amidino group, or $R^2$ and $R^3$ taken together represent a trimethylene, tetramethylene, pentamethylene, ethyleneoxyethylene, ethylenethioethylene, ethyleneaminoethylene, ethylene (methylamino)ethylene or ethyleneaminopropylene group.

Still more preferred examples include compounds wherein:

$R^1$ represents a hydrogen atom or a methyl group;

$R^2$ represents a hydrogen atom or a methyl group; and $R^3$ represents a methyl, 2-hydroxyethyl, carbamoylmethyl, 2-aminoethyl, 2-(methylamino) ethyl, cyclopropyl, formimidoyl, acetimidoyl or amidino group, or $R^2$ and $R^3$ taken together represent a tetramethylene group.

Most preferred examples include compounds wherein:

$R^1$ represents a hydrogen atom or a methyl group;

$R^2$ represents a hydrogen atom or a methyl group; and $R^3$ represents a hydrogen atom or a methyl, formimidoyl, acetimidoyl or amidino group.

In the above-exemplified preferred, more preferred, still more preferred and most preferred compounds (I), the stereoisomer represented by the following formula:

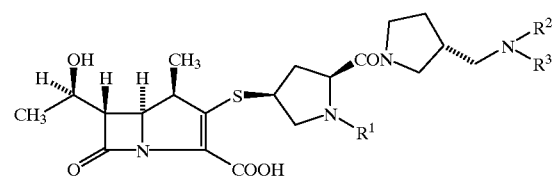

or the following formula:

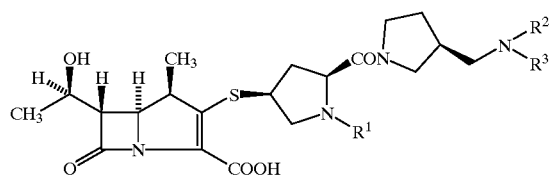

are more preferred compounds.

The preferred compounds of the formula (I) can be exemplified in Table 1.

TABLE 1

(I)

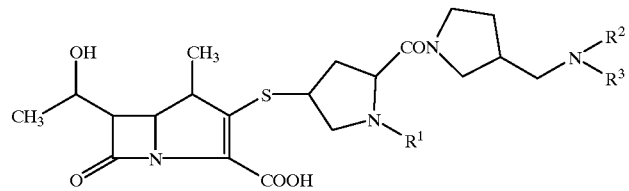

| Exemplified Compound No. | R¹ | R² | R³ |
|---|---|---|---|
| 1 | H | H | Me |
| 2 | H | H | Et |
| 3 | H | H | CH$_2$CH$_2$OH |
| 4 | H | H | CH$_2$CH$_2$F |
| 5 | H | H | CH$_2$CF$_3$ |
| 6 | H | H | CH$_2$CONH$_2$ |
| 7 | H | H | CH$_2$CH$_2$CONH$_2$ |
| 8 | H | H | CH$_2$CONHMe |
| 9 | H | H | CH$_2$CONMe$_2$ |
| 10 | H | H | CH$_2$CH$_2$OMe |
| 11 | H | H | CH$_2$CH$_2$OCONH$_2$ |
| 12 | H | H | CH$_2$CH$_2$NH$_2$ |
| 13 | H | H | CH$_2$CH$_2$NHMe |
| 14 | H | H | CH$_2$CH$_2$NMe$_2$ |
| 15 | H | H | cPr |
| 16 | H | H | C(=NH)H |
| 17 | H | H | C(=NH)Me |
| 18 | H | H | C(=NH)NH$_2$ |
| 19 | H | Me | Me |
| 20 | H | Me | Et |
| 21 | H | Me | CH$_2$CH$_2$OH |
| 22 | H | Me | CH$_2$CH$_2$F |
| 23 | H | Me | CH$_2$CF$_3$ |
| 24 | H | Me | CH$_2$CONH$_2$ |
| 25 | H | Me | CH$_2$CH$_2$CONH$_2$ |
| 26 | H | Me | CH$_2$CONHMe |
| 27 | H | Me | CH$_2$CONMe$_2$ |
| 28 | H | Me | CH$_2$CH$_2$OMe |
| 29 | H | Me | CH$_2$CH$_2$OCONH$_2$ |
| 30 | H | Me | CH$_2$CH$_2$NH$_2$ |
| 31 | H | Me | CH$_2$CH$_2$NHMe |
| 32 | H | Me | CH$_2$CH$_2$NMe$_2$ |
| 33 | H | Me | cPr |
| 34 | H | Me | C(=NH)H |
| 35 | H | Me | C(=NH)Me |
| 36 | H | Me | C(=NH)NH$_2$ |
| 37 | H | Et | Et |
| 38 | H | Et | CH$_2$CH$_2$OH |
| 39 | H | Et | CH$_2$CH$_2$F |
| 40 | H | Et | CH$_2$CF$_3$ |
| 41 | H | Et | CH$_2$CONH$_2$ |
| 42 | H | Et | CH$_2$CH$_2$CONH$_2$ |
| 43 | H | Et | CH$_2$CONHMe |
| 44 | H | Et | CH$_2$CONMe$_2$ |
| 45 | H | Et | CH$_2$CH$_2$OMe |
| 46 | H | Et | CH$_2$CH$_2$OCONH$_2$ |
| 47 | H | Et | CH$_2$CH$_2$NH$_2$ |
| 48 | H | Et | CH$_2$CH$_2$NHMe |
| 49 | H | Et | CH$_2$CH$_2$NMe$_2$ |
| 50 | H | Et | cPr |
| 51 | H | Et | C(=NH)H |

TABLE 1-continued

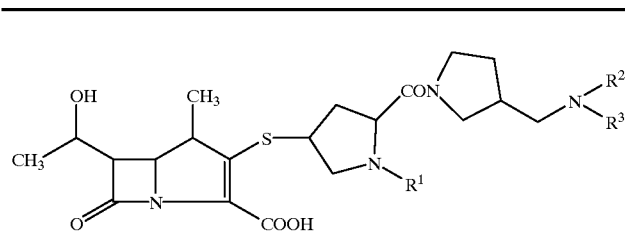

(I)

| Exemplified Compound No. | $R^1$ | $R^2$ | $R^3$ |
|---|---|---|---|
| 52 | H | Et | C(=NH)Me |
| 53 | H | Et | C(=NH)NH$_2$ |
| 54 | H | | —CH$_2$CH$_2$CH$_2$CH$_2$— |
| 55 | H | | —CH$_2$CH$_2$CH$_2$CH$_2$CH$_2$— |
| 56 | H | | —CH$_2$CH$_2$OCH$_2$CH$_2$— |
| 57 | H | | —CH$_2$CH$_2$SCH$_2$CH$_2$— |
| 58 | H | | —CH$_2$CH$_2$NHCH$_2$CH$_2$— |
| 59 | H | | —CH$_2$CH$_2$NHCH$_2$CH$_2$CH$_2$— |
| 60 | H | | —CH$_2$CH$_2$NMeCH$_2$CH$_2$— |
| 61 | Me | H | H |
| 62 | Me | H | Me |
| 63 | Me | H | Et |
| 64 | Me | H | CH$_2$CH$_2$OH |
| 65 | Me | H | CH$_2$CH$_2$F |
| 66 | Me | H | CH$_2$CF$_3$ |
| 67 | Me | H | CH$_2$CONH$_2$ |
| 68 | Me | H | CH$_2$CH$_2$CONH$_2$ |
| 69 | Me | H | CH$_2$CONHMe |
| 70 | Me | H | CH$_2$CONMe$_2$ |
| 71 | Me | H | CH$_2$CH$_2$OMe |
| 72 | Me | H | CH$_2$CH$_2$OCONH$_2$ |
| 73 | Me | H | CH$_2$CH$_2$NH$_2$ |
| 74 | Me | H | CH$_2$CH$_2$NHMe |
| 75 | Me | H | CH$_2$CH$_2$NMe$_2$ |
| 76 | Me | H | cPr |
| 77 | Me | H | C(=NH)H |
| 78 | Me | H | C(=NH)Me |
| 79 | Me | H | C(=NH)NH$_2$ |
| 80 | Me | Me | Me |
| 81 | Me | Me | Et |
| 82 | Me | Me | CH$_2$CH$_2$OH |
| 83 | Me | Me | CH$_2$CH$_2$F |
| 84 | Me | Me | CH$_2$CF$_3$ |
| 85 | Me | Me | CH$_2$CONH$_2$ |
| 86 | Me | Me | CH$_2$CH$_2$CONH$_2$ |
| 87 | Me | Me | CH$_2$CONHMe |
| 88 | Me | Me | CH$_2$CONMe$_2$ |
| 88 | Me | Me | CH$_2$CH$_2$OMe |
| 89 | Me | Me | CH$_2$CH$_2$OCONH$_2$ |
| 90 | Me | Me | CH$_2$CH$_2$NH$_2$ |
| 91 | Me | Me | CH$_2$CH$_2$NHMe |
| 92 | Me | Me | CH$_2$CH$_2$NMe$_2$ |
| 93 | Me | Me | cPr |
| 94 | Me | Me | C(=NH)H |
| 95 | Me | Me | C(=NH)Me |
| 96 | Me | Me | C(=NH)NH$_2$ |
| 97 | Me | Et | Et |
| 98 | Me | Et | CH$_2$CH$_2$OH |
| 99 | Me | Et | CH$_2$CH$_2$F |
| 100 | Me | Et | CH$_2$CF$_3$ |
| 101 | Me | Et | CH$_2$CONH$_2$ |
| 102 | Me | Et | CH$_2$CH$_2$CONH$_2$ |
| 103 | Me | Et | CH$_2$CONHMe |
| 104 | Me | Et | CH$_2$CONMe$_2$ |
| 105 | Me | Et | CH$_2$CH$_2$OMe |
| 106 | Me | Et | CH$_2$CH$_2$OCONH$_2$ |
| 107 | Me | Et | CH$_2$CH$_2$NH$_2$ |
| 108 | Me | Et | CH$_2$CH$_2$NHMe |
| 109 | Me | Et | CH$_2$CH$_2$NMe$_2$ |
| 110 | Me | Et | cPr |
| 111 | Me | Et | C(=NH)H |
| 112 | Me | Et | C(=NH)Me |
| 113 | Me | Et | C(=NH)NH$_2$ |
| 114 | Me | | —CH$_2$CH$_2$CH$_2$CH$_2$— |

TABLE 1-continued (I)

| Exemplified Compound No. | R¹ | R² | R³ |
|---|---|---|---|
| 115 | Me | | —CH₂CH₂CH₂CH₂CH₂— |
| 116 | Me | | —CH₂CH₂OCH₂CH₂— |
| 117 | Me | | —CH₂CH₂SCH₂CH₂— |
| 118 | Me | | —CH₂CH₂NHCH₂CH₂— |
| 119 | Me | | —CH₂CH₂NHCH₂CH₂CH₂— |
| 120 | Me | | —CH₂CH₂NMeCH₂CH₂— |
| 121 | Et | H | H |
| 122 | Et | H | Me |
| 123 | Et | H | Et |
| 124 | Et | H | CH₂CH₂OH |
| 125 | Et | H | CH₂CH₂F |
| 126 | Et | H | CH₂CF₃ |
| 127 | Et | H | CH₂CONH₂ |
| 128 | Et | H | CH₂CH₂CONH₂ |
| 129 | Et | H | CH₂CONHMe |
| 130 | Et | H | CH₂CONMe₂ |
| 131 | Et | H | CH₂CH₂OMe |
| 132 | Et | H | CH₂CH₂OCONH₂ |
| 133 | Et | H | CH₂CH₂NH₂ |
| 134 | Et | H | CH₂CH₂NHMe |
| 135 | Et | H | CH₂CH₂NMe₂ |
| 136 | Et | H | cPr |
| 137 | Et | H | C(=NH)H |
| 138 | Et | H | C(=NH)Me |
| 139 | Et | H | C(=NH)NH₂ |
| 140 | Et | Me | Me |
| 141 | Et | Me | Et |
| 142 | Et | Me | CH₂CH₂OH |
| 143 | Et | Me | CH₂CH₂F |
| 144 | Et | Me | CH₂CF₃ |
| 145 | Et | Me | CH₂CONH₂ |
| 146 | Et | Me | CH₂CH₂CONH₂ |
| 147 | Et | Me | CH₂CONHMe |
| 148 | Et | Me | CH₂CONMe₂ |
| 149 | Et | Me | CH₂CH₂OMe |
| 150 | Et | Me | CH₂CH₂OCONH₂ |
| 151 | Et | Me | CH₂CH₂NH₂ |
| 152 | Et | Me | CH₂CH₂NHMe |
| 153 | Et | Me | CH₂CH₂NMe₂ |
| 154 | Et | Me | cPr |
| 155 | Et | Me | C(=NH)H |
| 156 | Et | Me | C(=NH)Me |
| 157 | Et | Me | C(=NH)NH₂ |
| 158 | Et | Et | Et |
| 159 | Et | Et | CH₂CH₂OH |
| 160 | Et | Et | CH₂CH₂F |
| 161 | Et | Et | CH₂CF₃ |
| 162 | Et | Et | CH₂CONH₂ |
| 163 | Et | Et | CH₂CH₂CONH₂ |
| 164 | Et | Et | CH₂CONHMe |
| 165 | Et | Et | CH₂CONMe₂ |
| 166 | Et | Et | CH₂CH₂OMe |
| 167 | Et | Et | CH₂CH₂OCONH₂ |
| 168 | Et | Et | CH₂CH₂NH |
| 169 | Et | Et | CH₂CH₂NHMe |
| 170 | Et | Et | CH₂CH₂NMe₂ |
| 171 | Et | Et | cPr |
| 172 | Et | Et | C(=NH)H |
| 173 | Et | Et | C(=NH)Me |
| 174 | Et | Et | C(=NH)NH₂ |
| 175 | Et | | —CH₂CH₂CH₂CH₂— |
| 176 | Et | | —CH₂CH₂CH₂CH₂CH₂— |
| 177 | Et | | —CH₂CH₂OCH₂CH₂— |
| 178 | Et | | —CH₂CH₂SCH₂CH₂— |

TABLE 1-continued (I)

[Structure of compound (I) showing a carbapenem core with OH, CH₃, CH₃ substituents, a thio-linked pyrrolidine bearing CON-pyrrolidine-CH₂-NR²R³ group, and COOH]

| Exemplified Compound No. | R¹ | R² | R³ |
| --- | --- | --- | --- |
| 179 | Et | —CH₂CH₂NHCH₂CH₂— | |
| 180 | Et | —CH₂CH₂NHCH₂CH₂CH₂— | |
| 181 | Et | —CH₂CH₂NMeCH₂CH₂— | |

In the above Table-1, Me, Et and cPr represent a methyl, ethyl and cyclopropyl group, respectively.

Among the compounds exemplified in the above Table-1, compounds of Exemplified Compound Nos: 1, 3, 6, 12, 13, 16, 17, 18, 34, 35, 36, 61, 62, 77, 78, 79, 94, 95 and 96 are more preferred.

Of which, the compounds specified by the following chemical names are most preferred:

Stereoisomers of Exemplified Compound No. 1
(1R,5S,6S)-6-[(1R)-1-hydroxyethyl]-1-methyl-2-[(2S,4S)-2-[(3R)-3-methylaminomethylpyrrolidin-1-ylcarbonyl]pyrolidin-4-ylthio]-1-carbapen-2-em-3-carboxylic acid (Compound of Example 3)
(1R,5S,6S)-6-[(1R)-1-hydroxyethyl]-1-methyl-2-[(2S,4S)-2-[(3S)-3-methylaminomethylpyrrolidin-1-ylcarbonyl]pyrolidin-4-ylthio]-1-carbapen-2-em-3-carboxylic acid (Compound of Example 5)

Stereoisomers of Exemplified Compound No. 3
(1R,5S,6S)-6-[(1R)-1-hydroxyethyl]-2-[(2S,4S)-2-[(3R)-3-(2-hydroxyethylaminomethyl)pyrrolidin-1-ylcarbonyl]-1-methyl-1-carbapen-2-em-3-carboxylic acid
(1R,5S,6S)-6-[(1R)-1-hydroxyethyl]-2-[(2S,4S)-2-[(3S)-3-(2-hydroxyethylaminomethyl)pyrrolidin-1-ylcarbonyl]-1-methyl-1-carbapen-2-em-3-carboxylic acid (Compound of Example 13)

Stereoisomers of Exemplified Compound No. 6
(1R,5S,6S)-2-[(2S,4S)-2-[(3R)-3-(carbamoylmethylaminomethyl)pyrrolidin-1-ylcarbonyl]pyrrolidin-4-ylthio]-6-[(1R)-1-hydroxyethyl]-1-methyl-1-carbapen-2-em-3-carboxylic acid (Compound of Example 14)
(1R,5S,6S)-2-[(2S,4S)-2-[(3S)-3-(carbamoylmethylaminomethyl)pyrrolidin-1-ylcarbonyl]pyrrolidin-4-ylthio]-6-[(1R)-1-hydroxyethyl]-1-methyl-1-carbapen-2-em-3-carboxylic acid Stereoisomers of Exemplified Compound No. 12
(1R,5S,6S)-2-[(2S,4S)-2-[(3R)-3-(2-aminoethylaminomethyl)pyrrolidin-1-ylcarbonyl]pyrrolidin-4-ylthio]-6-[(1R)-1-hydroxyethyl]-1-methyl-i-carbapen-2-em-3-carboxylic acid
(1R, 5S,6S)-2-[(2S,4S)-2-[(3S)-3-(2-aminoethylaminomethyl)pyrrolidin-1-ylcarbonyl]pyrrolidin-4-ylthio]-6-[(1R)-1-hydroxyethyl]-1-methyl- 1-carbapen-2-em-3-carboxylic acid Stereoisomers of Exemplified Compound No. 13
(1R,5S,6S)-2-[(2S,4S)-2-[(3R)-3-(2-N-methylamino) ethylaminomethyl)pyrrolidin-1-ylcarbonyl]pyrrolidin-4-ylthio]-6-[(1R)-1-hydroxyethyl]-1-methyl-1-carbapen-2-em-3-carboxylic acid
(1R, 5S,6S)-2-[(2S,4S)-2-[(3S)-3-(2-N-methylamino) ethylaminomethyl)pyrrolidin-1-ylcarbonyl]pyrrolidin-4-ylthio]-6-[( 1 R)-1-hydroxyethyl]-1-methyl-1-carbapen-2-em-3-carboxylic acid Stereoisomers of Exemplified Compound No. 16
(1R,5S,6S)-2-[(2S,4S)-2-[(3R)-3-formimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid (Compound of Example 23)
(1R, 5S,6S)-2-[(2S,4S)-2-[(3S)-3-formimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid Stereoisomers of Exemplified Compound No. 17
(1R,5S,6S)-2-[(2S,4S)-2-[(3R)-3-acetimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid (Compound of Example 8)
(1R,5S,6S)-2-[(2S,4S)-2-[(3S)-3-acetimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid (Compound of Example 10)

Stereoisomers of Exemplified Compound No. 18
(1R,5S,6S)-2-[(2S,4S)-2-[(3R)-3-guanidinomethylpyrrolidin-1-ylcarbonyl]pyrrolidin-4-ylthio]-6-[(1R)-1-hydroxyethyl]-1-methyl-1-carbapen-2-em-3-carboxylic acid (Compound of Example 7)
(1R,5S,6S)-2-[(2S,4S)-2-[(3S)-3-guanidinomethylpyrrolidin-1-ylcarbonyl]pyrrolidin4-ylthio]-6-[(1R)-1-hydroxyethyl]-1-methyl-1-carbapen-2-em-3-carboxylic acid (Compound of Example 11)

Stereoisomers of Exemplified Compound No. 34
(1R, 5S,6S)-2-[(2S,4S)-2-[(3R)-3-N-methyl-N-formimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid (Compound of Example 21)
(1R,5S,6S)-2-[(2S,4S)-2-[(3S)-3-N-methyl-N-formimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid Stereoisomers of Exemplified Compound No. 35
(1R, 5S,6S)-2-[(2S,4S)-2-[(3R)-3-N-methyl-N-acetimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid (Compound of Example 20)
(1R,5S,6S)-2-[(2S,4S)-2-[(3S)-3-N-methyl-N-acetimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid Stereoisomers of Exemplified Compound No. 36
(1R,5S,6S)-2-[(2S,4S)-2-[(3R)-3-(1-methylguanidinomethyl)pyrrolidin-1-ylcarbonyl]pyrrolidin-4-ylthio]-6-[(1R)-1-hydroxyethyl]-1-methyl-1-carbapen-2-em-3-carboxylic acid (Compound of Example 19)
(1R,5S,6S)-2-[(2S,4S)-2-[(3S)-3-(1-methylguanidinomethyl)pyrrolidin-1-ylcarbonyl]pyrrolidin-4-ylthio]-6-[(1R)-1-hydroxyethyl]-1-methyl-1-carbapen-2-em-3-carboxylic acid Stereoisomers of Exemplified Compound No. 61
(1R,5S,6S)-2-[(2S,4S)-2-[(3R)-3-aminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid (Compound of Example 1)
(1R,5S,6S)-2-[(2S,4S)-2-[(3S)-3-aminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid (Compound of Example 2)

Stereoisomers of Exemplified Compound No. 62
(1R,5S,6S)-6-[(1R)-1-hydroxyethyl]-1-methyl-2-[(2S,4S)-2-[(3R)-3-methylaminomethylpyrrolidin-1-ylcarbonyl]-1-methylpyrrolidin-4-ylthio]-1-carbapen-2-em-3-carboxylic acid (Compound of Example 4)
(1R, 5S,6S)-6-[(1R)-1-hydroxyethyl]-1-methyl-2-[(2S,4S)-2-[(3S)-3-methylaminomethylpyrrolidin-1-ylcarbonyl]-1-methylpyrrolidin-4-ylthio]-1-carbapen-2-em-3-carboxylic acid (Compound of Example 6)

Stereoisomers of Exemplified Compound No. 77
(1R,5S,6S)-2-[(2S,4S)-2-[(3R)-3-formimidoylaminomethylpyrrolidin-1-ylcarbonyl]-1-methylpyrrolidin4-ylthio]-6-[(1R)-1-hydroxyethyl]-1-methyl-1-carbapen-2-em-3-carboxylic acid (Compound of Example 26)
(1R, 5S,6S)-2-[(2S,4S)-2-[(3S)-3-formimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomers of Exemplified Compound No. 78
(1R, 5S,6S)-2-[(2S,4S)-2-[(3R)-3-acetimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid (Compound of Example 25)
(1R,5S,6S)-2-[(2S,4S)-2-[(3S)-3-acetimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomers of Exemplified Compound No. 79
(1R,5S,6S)-2-[(2S,4S)-2-[(3R)-3-guanidinomethylpyrrolidin-1-ylcarbonyl]-1-methylpyrrolidin-4-ylthio]-6-[(1R)-1-hydroxyethyl]-1-methyl-1-carbapen-2-em-3-carboxylic acid (Compound of Example 24)
(1R, 5S,6S)-2-[(2S,4S)-2-[(3S)-3-guanidinomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomers of Exemplified Compound No. 94
(1R, 5S,6S)-2-[(2S,4S)-2-[(3R)-3-N-methyl-N-formimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid (Compound of Example 29)
(1R,5S,6S)-2-[(2S,4S)-2-[(3S)-3-N-methyl-N-formimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomers of Exemplified Compound No. 95
(1R,5S,6S)-2-[(2S,4S)-2-[(3R)-3-N-methyl-N-acetimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid (Compound of Example 28)
(1R,5S,6S)-2-[(2S,4S)-2-[(3S)-3-N-methyl-N-acetimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomers of Exemplified Compound No. 96
(1R,5S,6S)-2-[(2S,4S)-2-[(3R)-3-(1-methylguanidinomethyl)pyrrolidin-1-ylcarbonyl]-1-methylpyrrolidin4-ylthio]-6-[(1R)-1-hydroxyethyl]-1-methyl-1-carbapen-2-em-3-carboxylic acid (Compound of Example 27)
(1R,5S,6S)-2-[(2S,4S)-2-[(3S)-3-(1-methylguanidinomethyl)pyrrolidin-1-ylcarbonyl]-1-methylpyrrolidin-4-ylthio]-6-[(1R)-1-hydroxyethyl]-1-methyl-1-carbapen-2-em-3-carboxylic acid The 1-methylcarbapenem derivatives of the present invention represented by the formula (I) can be prepared by reacting a carbapenem compound of formula (II):

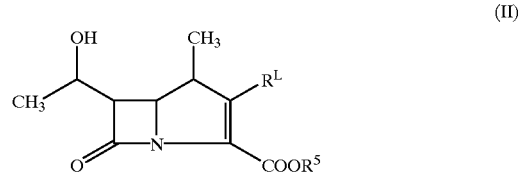

(II)

(wherein $R^L$ represents a leaving group and $R^5$ represents a carboxy protecting group) with a mercaptopyrrolidine derivative of formula (III):

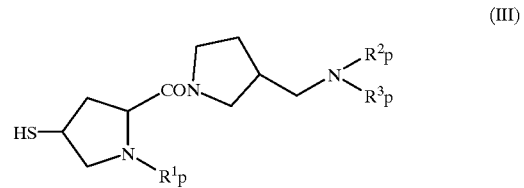

(III)

(wherein $R^1p$ represents an amino protecting group or has the same meaning as described in $R^1$, $R^2p$ represents an amino protecting group or has the same meaning as described in $R^2$ except that the amino, hydroxyl or imino group contained in $R^2$ may be protected, $R^3p$ represents an amino protecting group or has the same meaning as described in $R^3$ except that the amino, hydroxyl or imino group contained in $R^3$ may be protected) and then removal of the protecting group if necessary. Furthermore, it can be converted into its pharmacologically acceptable salts or derivatives if necessary.

The compound (I) of the present invention can be prepared by processes (Method A or Method B) illustrated below.

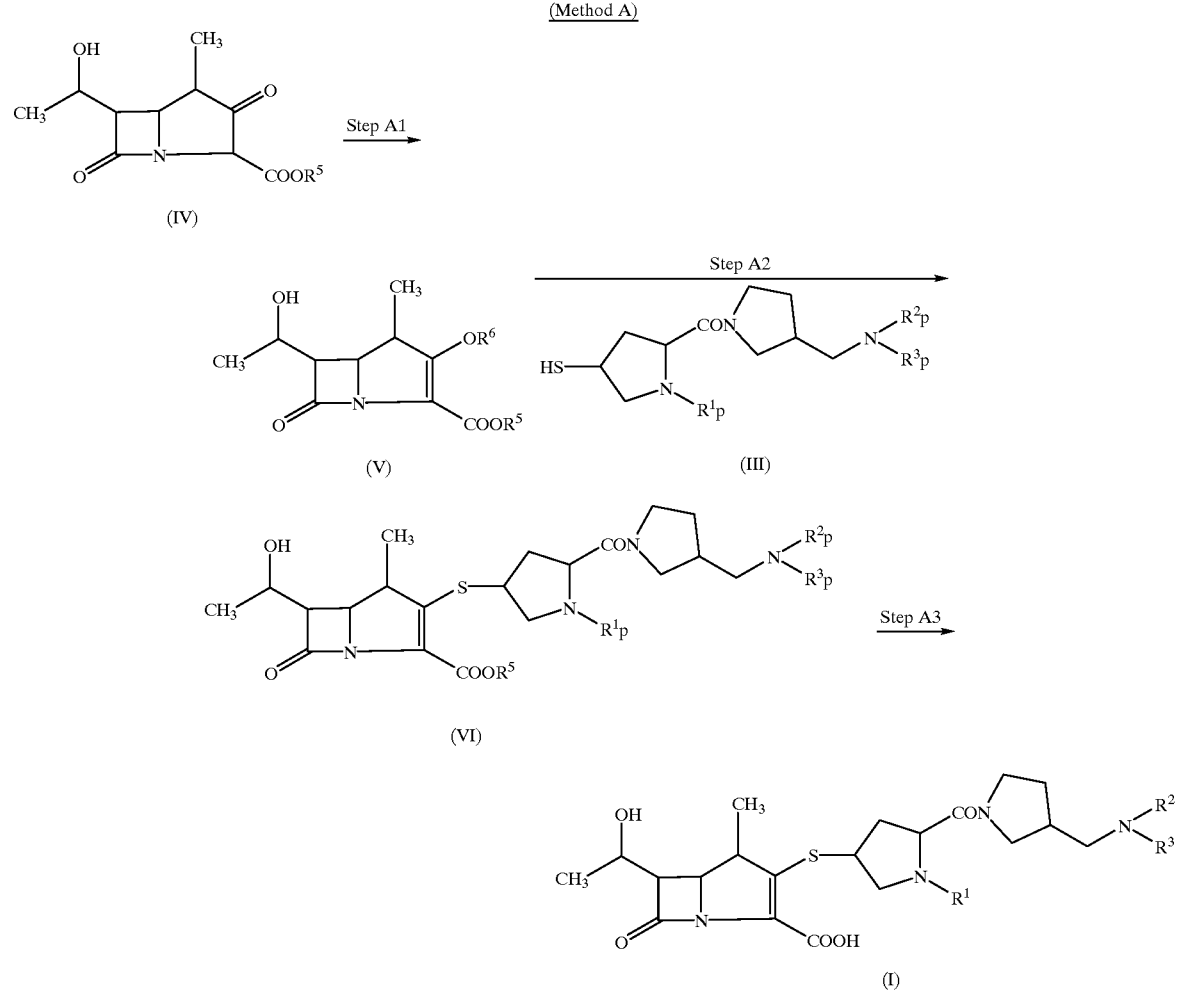

-continued (Method B)

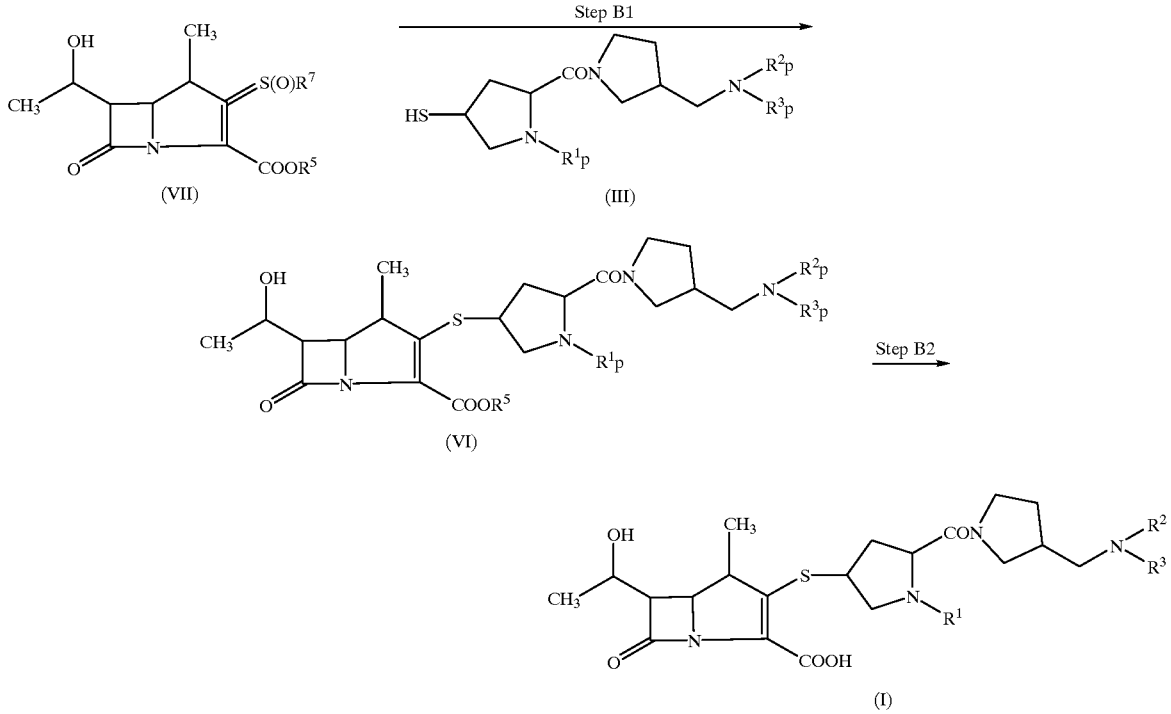

In the above formulae, $R^1$, $R^2$, $R^3$, $R^1p$, $R^2p$ and $R^3p$ have the same meanings as described above, and $R^5$ represents a carboxy protecting group.

The protecting group of the hydroxyl, amino or imino group contained in $R^1p$, $R^2p$ or $R^3p$ is a protecting group ordinarily used in the field of organic synthetic chemistry (Greene & Wuts, Protective Groups in Organic Synthesis, 2nd Edition, 1991, John Wiley & Sons, Inc.). Preferred examples include a benzyl group which may have a substituent such as benzyl and 4-nitrobenzyl; a benzyloxycarbonyl group which may have a substituent such as benzyloxycarbonyl and 4-nitrobenzyloxycarbonyl; or an allyloxycarbonyl group which may be substituted at the 2-position such as allyloxycarbonyl, 2-chloroallyloxycarbonyl and 2-methylallyloxycarbonyl; of which a 4-nitrobenzyl or 4-nitrobenzyloxycarbonyl group is more preferred.

The "carboxy protecting group" as $R^5$ is a protective group ordinarily used in the field of synthetic organic synthesis (Greene & Wuts, Protective Groups in Organic Synthesis, 2nd Edition, 1991, John Wiley & Sons, Inc.). Examples include a $C_{1-4}$ alkyl group such as methyl, ethyl or t-butyl; a benzyl group which may have a substituent such as benzyl, 4-methoxybenzyl, 4-nitrobenzyl or 2-nitrobenzyl; a benzhydryl group; an allyl group which may have a substituent at the 2-position such as allyl, 2-chloroallyl or 2-methylallyl; a halogenoethyl group such as 2,2,2-trichloroethyl, 2,2-dibromoethyl or 2,2,2-tribromoethyl; or 2-trimethylsilylethyl group; of which a 4-nitrobenzyl or benzyl group is more preferred.

$R^6$ represents a $C_{1-4}$ alkanesulfonyl group such as methanesulfonyl, trifluoromethanesulfonyl, ethanesulfonyl, propanesulfonyl, isopropanesulfonyl or butanesulfonyl, a $C_{6-10}$ arylsulfonyl group such as phenylsulfonyl, tolylsulfonyl or naphthylsulfonyl; a di-($C_{1-6}$ alkyl)phosphoryl group such as dimethylphosphoryl, diethylphosphoryl, dipropylphosphoryl, diisopropylphosphoryl, dibutylphosphoryl, dipentylphosphoryl or dihexylphosphoryl; or a di($C_{6-10}$ aryl)phosphoryl group such as diphenylphosphoryl or ditolylphosphoryl; of which a diphenylphosphoryl group is preferred.

$R^7$ represents a $C_{1-4}$ alkyl group such as methyl, ethyl, propyl or isopropyl; a halogeno-($C_{1-4}$ alkyl) group such as fluoromethyl, chloromethyl, fluoroethyl, chloroethyl, fluoropropyl, difluoromethyl, difluoroethyl, dichloroethyl, trifluoromethyl or trifluoroethyl; a 2-acetylaminoethyl group; a 2-acetylaminovinyl group; a $C_{6-10}$ aryl group, such as phenyl or naphthyl, which may have substituents (said aryl group may have one to three substituents. They are the same as or different from each other and each substituent is described below. Examples include a halogen atom such as fluorine, chlorine and bromine; a $C_{1-4}$ alkyl group such as methyl, ethyl, propyl and isopropyl; a $C_{1-4}$ alkoxy group such as methoxy, ethoxy, propoxy and isopropoxy; a ($C_{1-4}$ alkoxy)carbonyl group such as methoxycarbonyl, ethoxycarbonyl and t-butoxycarbonyl; a carbamoyl group, a mono- or di-($C_{1-4}$ alkyl)carbamoyl group; a nitro group; a hydroxyl group; and a cyano group); or a heteroaryl group which has one or two nitrogen atoms, such as pyridyl or pyrimidinyl, and may have substituents (said heteroaryl group may have one to three substituents. They are the same or different from each other and each includes a halogen atom and a $C_{1-4}$ alkyl group which have been exemplified above as the substituent of the aryl group).

Incidentally, examples of the "leaving group" of $R^L$ include a group represented by formula —$OR^6$ or —$S(O)R^7$.

In method A, a Compound (I) is prepared by reacting the compound of formula (IV) with a sulfonylating or phosphorylating agent in the presence of a base to afford a compound of formula (V) (Step A1); by reacting Compound (V) with a compound of formula (III) in the presence of a base to give a compound of formula (VI) (Step A2); and finally, by removing any protecting groups from the compound of formula (VI) (Step A3). Each step will be described below.

Step A1

In Step A1 a compound of formula (V) is prepared by reacting a compound of formula (IV) with a sulfonylating or phosphorylating agent in an inert solvent in the presence of a base.

Examples of the sulfonylating agent include $C_{1-4}$ alkanesulfonic anhydrides such as methanesulfonic anhydride, trifluoromethanesulfonic anhydride and ethanesulfonic anhydride; and $C_{6-10}$ arylsulfonic anhydrides such as benzenesulfonic anhydride and p-toluenesulfonic anhydride; of which p-toluenesulfonic anhydride is preferred.

Examples of the phosphorylating agent include di($C_{1-4}$ alkyl)phosphoryl halides such as dimethylphosphoryl chloride and diethylphosphoryl chloride; and di($C_{6-10}$ aryl) phosphoryl halides such as diphenylphosphoryl chloride and diphenylphosphoryl bromide; of which diphenylphosphoryl chloride is preferred.

There is no particular limitation on the nature of the solvent to be employed, provided that it has no adverse effect on the reaction. Examples of suitable solvents include halogenated hydrocarbons such as methylene chloride, 1,2-dichloroethane and chloroform, nitriles such as acetonitrile, amides such as N,N-dimethylformamide and N,N-dimethylacetamide, esters such as ethyl acetate and methyl acetate, and ethers such as diethyl ether, tetrahydrofuran and dioxane; of which acetonitrile, N,N-dimethylformamide or tetrahydrofuran is preferred, acetonitrile being most preferred.

There is no particular limitation on the nature of the base to be employed, provided that it does not affect the other part of the compound, particularly the β-lactam ring. Preferred examples of the base include organic bases such as triethylamine, diisopropylethylamine, pyridine and 4-dimethylaminopyridine; of which diisopropylethylamine is more preferred.

Although no particular limitation is imposed on the reaction temperature, reaction at a relatively low temperature is desirable in order to suppress side reactions. The reaction is usually carried out at a temperature from −20° C. to 40° C. (preferably from −10° C. to 20° C.). The reaction time mainly depends on the reaction temperature or nature of reagents; however it ranges from 10 minutes to 5 hours (preferably from 15 minutes to 1 hour).

After the completion of the reaction, a resulting compound (V) of the present step is obtained from the reaction mixture by known means. For example, to the reaction mixture or to the residue obtained by distilling off the solvent from the reaction mixture, an organic solvent which is not miscible with water is added, followed by washing with water and distilling off the organic solvent. If necessary, the resulting compound can be further purified by known means, for example, by recrystallization, reprecipitation or chromatography. It is also possible to subject the resulting compound (V) to the subsequent reaction (step A2) without isolation from the reaction mixture, if desired.

Step A2

In Step A2 a compound of formula (VI) is prepared by reacting a compound (V) with a mercaptopyrrolidine derivative of formula (III) in an inert solvent in the presence of a base.

There is no particular limitation on the nature of the solvent to be employed, provided that it has no adverse effect on the reaction. Examples of suitable solvents include halogenated hydrocarbons such as methylene chloride, 1,2-dichloroethane and chloroform; nitriles such as acetonitrile; amides such as N,N-dimethylformamide and N,N-dimethylacetamide; esters such as ethyl acetate and methyl acetate; and ethers such as diethyl ether, tetrahydrofuran and dioxane; of which acetonitrile, N,N-dimethylformamide or tetrahydrofuran is preferred, acetonitrile being more preferred.

Although no particular limitation is imposed on the nature of the base to be employed in the present step, preferred examples include organic amines such as triethylamine and diisopropylethylamine and inorganic bases such as potassium carbonate and sodium carbonate; of which diisopropylethylamine is more preferred.

Although no particular limitation is imposed on the reaction temperature, the reaction is usually carried out at a temperature from −20° C. to 40° C. (preferably from −10° C. to 20° C.). The reaction time ranges from 30 minutes to 108 hours (preferably from 1 hour to 18 hours).

After the completion of the reaction, the resulting compound (VI) of the present step is obtained from the reaction mixture by known means. For example, to the reaction mixture or to the residue obtained by distilling off the solvent from the reaction mixture, an organic solvent which is not miscible with water is added, followed by washing with water and distilling off the organic solvent. If necessary, the resulting compound can be further purified by known means, for example, by recrystallization, reprecipitation or chromatography. It is also possible to subject the resulting compound (VI) to the subsequent reaction (step A3) without isolation from the reaction mixture, if desired.

Step A3

In Step A3, a compound (VI) is converted to a compound (I) by removal of any protecting groups from the compound (VI).

Although the method for removal of a protecting group depends on the nature of it, the protecting group is usually removed by a method ordinarily employed in the field of synthetic organic chemistry (Greene & Wuts, Protective Groups in Organic Synthesis, 2nd Edition, 1991, John Wiley & Sons, Inc.).

(1) When the protecting group $R^5$ is, for example, a benzyl group which may have a substituent, such as benzyl or 4-nitrobenzyl, or a benzhydryl group, and when the protecting group of the hydroxyl, amino or imino group contained in $R^1p$, $R^2p$ or $R^3p$ is a benzyl group which may have a substituent, such as benzyl or 4-nitrobenzyl, or a benzyloxycarbonyl group which may have a substituent, such as benzyloxycarbonyl or 4-nitrobenzyloxycarbonyl, the protecting group can be removed by reacting with a reducing agent such as the combination of hydrogen with a hydrogenation catalyst or an alkali metal sulfide.

Examples of the reducing agent include combinations of hydrogen with a hydrogenation catalyst such as palladium-carbon and alkali metal sulfides such as sodium sulfide and potassium sulfide; of which the combination of hydrogen with palladium-carbon is preferred.

There is no particular limitation on the nature of the solvent to be employed, provided that it has no adverse effect on the present reaction; however, alcohols such as methanol and ethanol, ethers such as tetrahydrofuran and dioxane and a mixture of said organic solvents and water are preferred.

The reaction temperature usually ranges from 0° C. to 50° C. (preferably from 10° C. to 40° C.). The reaction time depends on the natures of the starting compound and the reducing agent; however it usually ranges from 5 minutes to 12 hours (preferably from 30 minutes to 4 hours).

After the completion of the reaction, a compound (I) is obtained from the reaction mixture by known means. For example, the resulting compound can be obtained by filtering off an insoluble material from the reaction mixture and then distilling off the solvent.

(2) When the protecting group $R^5$ is an allyl group which may be substituted at the 2-position such as allyl, 2-chloroallyl or 2-methylallyl and when the protective group of the hydroxyl group, amino group or imino group contained in $R^1p$, $R^2p$ or $R^3p$ is an allyloxycarbonyl group which may be substituted at the 2-position such as allyloxycarbonyl, 2-chloroallyloxycarbonyl or 2-methylallyloxycarbonyl, the protecting groups can be removed by reacting with a deprotecting agent; for example, a palladium-trialkyltin hydride such as bis(triphenylphosphine)palladium chloride-tributyltin hydride or tetrakis(triphenylphosphine)palladium-tributyltin hydride or a palladium-alkali metal salt of an organic carboxylic acid such as tetrakis(triphenylphosphine)palladium-potassium 2-ethylhexanoate or -sodium 2-ethylhexanoate.

Preferred examples of the deprotecting agents include bis(triphenylphosphine)palladium chloride-tributyltin hydride and tetrakis(triphenylphosphine)palladium-potassium 2-ethylhexanoate.

There is no particular limitation on the nature of the solvent to be used, provided that it has no adverse effect on the present reaction. Examples include the halogenated hydrocarbons such as methylene chloride, chloroform and 1,2-dichloroethane, esters such as ethyl acetate, ethers such as tetrahydrofuran, dioxane and 1,2-dimethoxyethane, nitriles such as acetonitrile, alcohols such as methanol, ethanol and propanol and water, and a mixture thereof, of which methylene chloride, ethyl acetate and mixtures thereof are preferred.

Although no particular limitation is imposed on the reaction temperature, the reaction is usually carried out at a temperature from –20° C. to 100° C. (preferably from 0° C. to 60° C.). The reaction time usually ranges from 30 minutes to 48 hours (preferably from 30 minutes to 12 hours).

After completion of the reaction, a compound (I) is obtained from the reaction mixture by known means. For example, the insoluble material precipitated by the reaction is filtered off from the reaction mixture, followed by distilling off the solvent, to afford a compound (I).

(3) When the protecting group $R^5$ is a halogenoethyl group such as 2,2-dibromoethyl or 2,2,2-trichloroethyl, the protecting group can be removed by reacting with a reducing agent such as the combination of a metal such as zinc with an acid such as acetic acid or hydrochloric acid.

Preferred examples of the reducing agent include the combination of zinc with acetic acid.

There is no particular limitation on the nature of the solvent to be employed, provided that it has no adverse effect on the present reaction. Preferred examples include alcohols such as methanol and ethanol, ethers such as tetrahydrofuran and dioxane, aliphatic acids such as acetic acid and mixtures of said organic solvents and water.

The reaction temperature usually ranges from 0° C. to 40° C. (preferably from 10° C. to 30° C.). The reaction time depends on the natures of the starting compound and reducing agent; however, it usually ranges from 5 minutes to 12 hours (preferably from 30 minutes to 4 hours).

After the completion of the reaction, a compound (I) is obtained from the reaction mixture by known means. For example, the insoluble matter is filtered off from the reaction mixture, followed by distilling off the solvent, whereby a compound (I) can be obtained.

If necessary, the resulting compound (I) can be purified by known means, for example, by recrystallization, preparative thin-layer chromatography or column chromatography.

On the other hand, Method B is another process for the preparation of compound (I). Described specifically, a compound of formula (VII) is subjected to a reaction with a compound of formula (III) in the presence of a base to give a compound of formula (VI) (Step B1) and then any protecting groups in the compound (IV) are removed to afford a compound (I) (Step B2). The starting compound of formula (VII) used in this synthetic process is prepared by the method disclosed in Japanese Patent Application Kokai No. SHO 62-30781. A description of each step will next be made.

Step B1

In Step B1 a compound of formula (VI) is prepared by reacting Compound (VII) with a mercaptopyrrolidine derivative (III) in an inert solvent in the presence of a base.

There is no particular limitation on the nature of the solvent to be employed, provided that it has no adverse effect on the present reaction. Examples of suitable solvents include tetrahydrofuran, acetonitrile, dimethylformamide, dimethylsulfoxide and water, and a mixture thereof, of which the acetonitrile is preferred.

There is no particular limitation on the nature of the base to be employed, provided that it does not affect the other part of the compound, particularly the β-lactam ring. Examples of suitable bases include organic bases such as diisopropylethylamine, triethylamine, N-methylpiperidine and 4-dimethylaminopyridine; and inorganic bases such as potassium carbonate and sodium bicarbonate, of which diisopropylethylamine is preferred.

Although no particular limitation is imposed on the reaction temperature, it is preferred to carry out the reaction at a relatively low temperature in order to suppress side reactions. The reaction temperature usually ranges from –20° C. to 40° C. (preferably from –10° C. to 20° C.).

The reaction time mainly depends on the reaction temperature or nature of the reaction reagent; however it usually ranges from 15 minutes to 75 hours (preferably from 30 minutes to 18 hours).

After the completion of the reaction, the resulting compound (VI) of this step is obtained from the reaction mixture by known means. To the reaction mixture or a residue available by distilling off the solvent from the reaction mixture, an organic solvent which is not miscible with water is added, followed by washing with water and distilling off the organic solvent. If necessary, the resulting compound can be further purified by known means; for example, by recrystallization, reprecipitation or chromatography. It is also possible to subject the resulting compound (VI) to the subsequent reaction (step B2) without isolation from the reaction mixture, if necessary.

Step B2

In the Step B2 a compound (I) is prepared by removal of any protecting groups from the compound (VI).

This step can be accomplished by a similar method to that described in Step A3 of Method A.

The 1-methylcarbapenem compound of the formula (I) thus obtained by Method A or B can be converted into its pharmacologically acceptable salt or derivative (preferably an ester derivative) by a method well known in the field of β-lactam antibiotics.

Incidentally, the mercaptopyrrolidine compound (IV) to be used as a starting material in each of Methods A and B can be prepared by a known method; for example, the methods described in I. Kawamoto et al., Synlett, 575(1995), Japanese Patent Application Kokai No. Hei 2-28180, Japanese Patent Application Kokai No. Hei 2-3687, Japanese Patent Application No. Hei 4-211083 or Japanese Patent Application Kokai No. Hei 5-339269.

The compounds of formula (I) and pharmacologically acceptable salt thereof of the present invention exhibit strong and well-balanced antibacterial activity against a wide range of bacteria including Gram positive bacteria such as *Staphylococcus aureus* and *Bacillus subtilis,* Gram negative bacteria such as *Escherichia col,* Shigella species, *Klebsiella penumoniae,* Proteus species, Serratia species, Enterobacter species and *Pseudomonas aeruginosa,* and anaerobes such as *Bacteroides fragilis.* They also exhibit excellent antibacterial activity against *Pseudomonas aeruginosa* having resistance against meropenem. In addition, the compounds (I) of the present invention exhibit high stability against β-lactamases and against dehydropeptidase-I, and high recovery rates in urine. Furthermore, the compounds (I) of the present invention are excellent in in vivo kinetics such as half-life in blood and are relatively free from nephrotoxicity. Judging from these advantages, they are excellent antibiotics.

Compared with aminomethyl compounds [compounds represented by the formula (I) wherein $R^1$, $R^2$ and $R^3$ represent hydrogen atoms; Compound A and Compound B disclosed in Japanese Patent Application Kokai No. Hei 5-310740], the compounds (I) having a substituent at the amino group exhibited superior activity against *Pseudomonas aeruginosa,* superior in vivo kinetics and lower nephrotoxicity.

Accordingly, the compounds of the formula (I) and pharmacologically acceptable salts or derivatives thereof of the present invention are excellent antibacterial agents for the treatment or prevention (preferably, treatment) of infections caused by various bacteria.

Capability of Utility in Industry

When compounds (I) or pharmacologically acceptable salts thereof are used as antibacterial agents, they can be administered orally in the form of tablets, capsules, granules, powders or syrups by using them as they are or mixing them with a necessary pharmacologically acceptable additive such as excipient or diluent, or administered parenterally in the form of injections.

The above formulations can be prepared in a known manner by using additives. Examples of the additives include excipients (e.g. sugar derivatives such as lactose, sucrose, dextrose, mannitol or sorbitol; starch derivative such as corn starch, potato starch, α-starch, dextrin or carboxymethyl starch; cellulose derivatives such as crystalline cellulose, low-substituted hydroxypropylcellulose, hydroxypropylmethylcellulose, carboxymethylcellulose, carboxymethylcellulose calcium or internally cross-linked carboxymethylcellulose sodium; acacia; dextran; pullulan; silicate derivatives such as light silicic anhydride, synthetic aluminum silicate or magnesium aluminometasilicate; phosphate derivatives such as calcium phosphate; carbonate derivatives such as calcium carbonate; or sulfate derivatives such as calcium sulfate), binders (e.g. the above-exemplified excipients, gelatin, polyvinyl pyrrolidone; or Macrogol), disintegrators (e.g. the above-exemplified excipients or chemically modified starch or cellulose derivatives such as cross carmellose sodium, carboxymethyl starch sodium or crosslinked polyvinylpyrrolidone), lubricants (e.g. talc, stearic acid, metal salts of stearic acid such as calcium stearate or magnesium stearate; colloidal silica; veegum; wax such as spermaceti; boric acid; glycol; carboxylic acids such as fumaric acid or adipic acid; sodium carboxylates such as sodium benzoate; sulfates such as sodium sulfate; leucine; lauryl sulfates such as sodium lauryl sulfate or magnesium lauryl sulfate; silicic acids such as silicic anhydride or silicic hydrate; or starch derivatives exemplified above as the excipient), stabilizers (e.g. p-hydroxybenzoates such as methyl p-hydroxybenzoate or propyl p-hydroxybenzoate; alcohols such as chlorobutanol, benzyl alcohol or phenylethyl alcohol; benzalkonium chloride; phenol derivatives such as phenol or cresol; thimerosal; acetic anhydride; or sorbic acid), corrigents (e.g. ordinarily-employed sweeteners, souring agents or flavors), suspending agents (e.g. Polysorbate 80 or carboxymethylcellulose sodium), diluents and solvents for formulation (e.g. water, ethanol or glycerin).

The dose of the compounds (I) will vary depending on the condition and age of the patient. Orally, they are administered in an amount of 10 mg (preferably 50 mg) in a single dose as a lower limit and 2000 mg (preferably 1000 mg) in a single dose as an upper limit, while intravenously, they are administered in an amount of 10 mg (preferably 100 mg) in a single dose as a lower limit and 3000 mg (preferably 2000 mg) in a single dose as an upper limit. It is desirable to be administered to an adult in a single dose or in divided dose (sixth) per day depending on the condition of the patient.

Best Modes for Carrying out the Invention

The present invention will hereinafter be described in more detail by examples, referential examples, tests and formulation examples. However the present invention is not limited to or by these examples. Incidentally, in the nuclear magnetic resonance spectrum in the examples and referential examples, sodium trimethylsilylpropionate-$d_4$ was used as an internal standard for the measurement in heavy water, while tetramethylsilane was used as an internal standard in the other solvents, unless otherwise indicated.

EXAMPLE 1

(1R,5S,6S)-2-[(2S,4S)-2-[(3R)-3-Aminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomer of Exemplified Compound No. 61

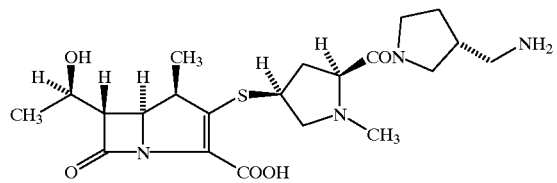

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.72 g) in anhydrous acetonitrile (7 ml), N,N-diisopropylethylamine (0.21 ml) and a solution of (2S,4S)-4-mercapto-1-methyl-2-[(3R)-3-(4-nitrobenzyloxycarbonylaminomethyl)pyrrolidin-1-ylcarbonyl]pyrrolidine (0.54 g) in anhydrous acetonitrile (10 ml) were added while stirring in an ice bath. The resulting mixture was stirred overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column ( ethyl acetate/methanol=7/3), whereby 4-nitrobenzyl (1R,5S,6S)-6-[(1R)-1-hydroxyethyl]-1-methyl-2-[(2S,4S)-1-methyl-2-[(3R)-3-(4-nitrobenzyloxycarbonylaminomethyl)pyrrolidin-1-ylcarbonyl]pyrrolidin-4-ylthio]-1-carbapen-2-em-3-carboxylate (0.74 g) was obtained.

Infrared absorption spectrum (KBr) ν max cm$^{-1}$: 1771, 1721, 1637, 1608, 1522, 1490, 1274, 1245, 1210, 1181, 1137, 1107, 1074, 1046, 1026, 1014.

Nuclear magnetic resonance spectrum (270 MHz, CDCl$_3$)δ ppm: 1.27 (3H,d,J=7.3Hz), 1.36(3H,d,J=6.6Hz), 1.45–2.80(5H,m), 2.31,2.31(3H,sx2), 2.98–3.90(13H,m), 4.18–4.30(2H,m), 5.10–5.50(4H,m), 7.48(2H,d,J=8.6Hz), 7.63(2H,d,J=8.6Hz), 8.20(4H,d,J=8.6Hz).

(2) To a solution of the compound (0.73 g), which had been obtained in (1), in tetrahydrofuran (40 ml) and water (28 ml), a 10% palladium-carbon catalyst (1.46 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was separated by reversed-phase column chromatography ["Cosmosil 75C18-PREP" (NACALAI TESQUE, INC.), acetonitrile/water=6/94–1/9 (elution while an acetonitrile concentration was increased gradually from 6% to 10%)], followed by concentration by evaporation under reduced pressure and lyophilization, whereby crude title compound (246 mg) was obtained as a powder.

Out of the 246 mg of the crude title compound, a 230 mg portion was separated and purified through an HPLC preparative column ["Cosmosil 5C 18-AR" (NACALAI TESQUE, INC.), acetonitrile/water=6/94–1/9 (elution while an acetonitrile concentration was increased gradually from 6% to 10%)], followed by concentration by evaporation under reduced pressure and lyophilization, whereby the title compound (156 mg) was obtained as a powder.

Infrared absorption spectrum (KBr) ν max cm$^{-1}$: 1758, 1633, 1594, 1488, 1455, 1385, 1340, 1313, 1253, 1225, 1210, 1181, 1149, 1095.

Nuclear magnetic resonance spectrum (400 MHz, D$_2$O) δ ppm: 1.21(3H,d,J=7.2Hz), 1.30(3H,d,J=6.4Hz), 1.63–1.86 (2H,m), 2.14–2.93(4H,m), 2.32(3H,s), 3.03–4.01(13H,m), 4.17–4.30(2H,m).

EXAMPLE 2

(1R,5S,6S)-2-[(2S,4S)-2-[(3S)-3-Aminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomer of Exemplified Compound No. 61

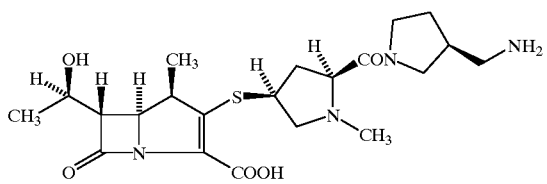

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.73 g) in anhydrous acetonitrile (7 ml), N,N-diisopropylethylamine (0.22 ml) and a solution of (2S,4S)-4-mercapto-1-methyl-2-[(3S)-3-(4-nitrobenzyloxycarbonylaminomethyl)pyrrolidin-1-ylcarbonyl]pyrrolidine (0.57 g) in anhydrous acetonitrile (10 ml) were added while stirring in an ice bath. The resulting mixture was stirred overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=7/3), whereby 4-nitrobenzyl (1R,5S,6S)-6-[(1R)-1-hydroxyethyl]-1-methyl-2-[(2S,4S)-1-methyl-2-[(3S)-3-(4-nitrobenzyloxycarbonylaminomethyl)pyrrolidin-1-ylcarbonyl]pyrrolidin-4-ylthio]-1-carbapen-2-em-3-carboxylate (0.78 g) was obtained.

Infrared absorption spectrum (KBr) ν max cm$^{-1}$: 1771, 1721, 1638, 1608, 1522, 1490, 1453, 1375, 1347, 1324, 1274, 1246, 1210, 1181, 1137.

Nuclear magnetic resonance spectrum (270 MHz, CDCl$_3$) δ ppm: 1.25(3H,d,J=7.3Hz), 1.36(3H,d,J=6.6Hz), 1.46–2.80 (5H,m), 2.31(3H,s), 2.98–4.00(13H,m), 4.18–4.31(2H,m), 5.11–5.50(4H,m), 7.42–7.67(4H,m), 8.13–8.25(4H,m).

(2) To a solution of the compound (0.76 g), which had been obtained in (1), in tetrahydrofuran (40 ml) and water (28 ml), a 10% palladium-carbon catalyst (1.55 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was separated by reversed-phase column chromatography ["Cosmosil 75C18-PREP" (NACALAI TESQUE, INC.), acetonitrile/water=6/94–1/9], followed by concentration by evaporation under reduced pressure and lyophilization, whereby crude title compound (248 mg) was obtained as a powder. Out of 248 mg of the compound, a 189 mg portion was separated and purified through an HPLC preparative column ["Cosmosil SC 18-AR" (NACALAI TESQUE, INC.), acetonitrile/water=6/94–1/9], followed by concentration by evaporation under reduced pressure and lyophilization, whereby the title compound (125 mg) was obtained as a powder.

Infrared absorption spectrum (KBr) ν max cm$^{-1}$: 1759, 1633, 1595, 1488, 1455, 1384, 1253, 1211, 1180, 1148, 1095.

Nuclear magnetic resonance spectrum (400 MHz, D$_2$O) δ ppm: 1.21(3H,d,J=7.2Hz), 1.30(3H,d,J=6.4Hz), 1.63–1.87 (1H,m),2.13–2.40(1H,m), 2.31,2.30(3H,sx2), 2.53–2.93 (3H,m), 3.08–3.90(1 1H,m), 4.18–4.29(2H,m).

EXAMPLE 3

(1R,5S,6S)-6-[(1R)-1-Hydroxyethyl]-1-methyl-2-[(2S,4S)-2-[(3R)-3-methylaminomethylpyrrolidin-1-ylcarbonyl]pyrrolidin-4-ylthio]-1-carbapen-2-em-3-carboxylic acid Stereoisomer of Exemplified Compound No. 1

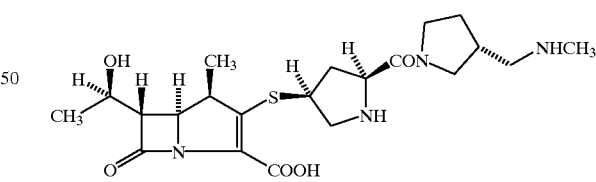

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (1.76 g) in anhydrous acetonitrile (20 ml), N,N-diisopropylethylamine (0.51 ml) and a solution of (2S,4S)-4-mercapto-2-[(3S)-3-(N-methyl-N-4-nitrobenzyloxycarbonylaminomethyl)pyrrolidin-1-ylcarbonyl]-1-(4-nitrobenzyloxycarbonyl)pyrrolidine (1.92 g) in anhydrous acetonitrile (20 ml) were added while stirring in an ice bath. The resulting mixture was stirred overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=95/5–9/1), whereby 4-nitrobenzyl (1R,5S,6S)-6-[(1R)-1-hydroxyethyl]-1-methyl-2-[(2S,4S)-2-[(3S)-3-(N-methyl-N-4-nitrobenzyloxycarbonylaminomethyl)-1-(4-nitrobenzyloxycarbonyl)pyrrolidin-1-ylcarbonyl]-pyrrolidin-4-ylthio]-1-carbapen-2-em-3-carboxylate (2.52 g) was obtained.

Infrared absorption spectrum (KBr) ν max cm$^{-1}$: 1774, 1707, 1652, 1607, 1522, 1441, 1404, 1346, 1295, 1210, 1143, 1110.

Nuclear magnetic resonance spectrum (400 MHz, CDCl$_3$) δ ppm: 1.29(3H,d,J=7.2Hz), 1.37(3H,d,J=6.1Hz), 1.55–2.73 (5H,m), 2.93–4.58(18H,m), 5.02–5.52(6H,m), 7.40–7.70 (6H,m), 8.15–8.30(6H,m).

(2) To a solution of the compound (2.52 g), which had been obtained in (1), in tetrahydrofuran (120 ml) and water (84 ml), a 10% palladium-carbon catalyst (5.07 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was purified by reversed-phase column chromatography ["Cosmosil 75C18-PREP" (NACALAI TESQUE, INC.), acetonitrile/water=6/94–8/92], followed by concentration by evaporation under reduced pressure and lyophilization, whereby the title compound (406 mg) was obtained as a powder.

Infrared absorption spectrum (KBr) ν max cm$^{-1}$: 1757, 1634, 1598, 1456, 1386, 1311, 1284, 1257, 1225, 1180, 1148, 1099.

Nuclear magnetic resonance spectrum (400 MHz, D$_2$O) δ ppm: 1.22(3H,d,J=7.2Hz), 1.30(3H,d,J=6.4Hz), 1.58–1.87 (2H,m), 2.16–2.31(1H,m), 2.58–2.80(2H,m), 2.76(3H,s), 3.03–4.07(12H,m), 4.18–4.29(2H,m).

EXAMPLE 4

(1R,5S,6S)-6-[(1R)-1-Hydroxyethyl]-1-methyl-2-[(2S,4S)-2-[(3R)-3-methylaminomethylpyrrolidin-1-ylcarbonyl]-1-methylpyrrolidin-4-ylthio]-1-carbapen-2-em-3-carboxylic acid Stereoisomer of Exemplified Compound No. 62

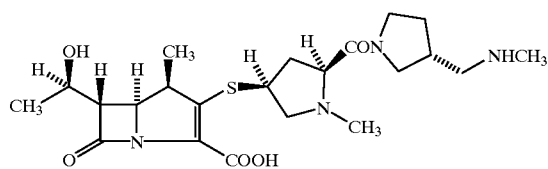

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.72 g) in anhydrous acetonitrile (5 ml), N,N-diisopropylethylamine (0.21 ml) and a solution of (2S,4S)-4-mercapto-1-methyl-2-[(3S)-3-(N-methyl-N-4-nitrobenzyloxycarbonylaminomethyl) pyrrolidin-1-ylcarbonyl]pyrrolidine (0.54 g) in anhydrous acetonitrile (5 ml) were added while stirring in an ice bath. The resulting mixture was allowed to react overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=6/4), whereby 4-nitrobenzyl (1R,5S,6S)-6-[(1R)-1-hydroxyethyl]-1-methyl-2-[(2S,4S)-1-methyl-2-[(3S)-3-(N-methyl-N-4-nitrobenzyloxycarbonylaminomethyl)pyrrolidin-1-ylcarbonyl]pyrrolidin-4-ylthio]-1-carbapen-2-em-3-carboxylate (0.46 g) was obtained.

Infrared absorption spectrum (KBr) ν max cm$^{-1}$: 1770, 1705, 1640, 1607, 1522, 1489, 1452, 1403, 1376, 1346, 1278, 1210, 1143, 1106.

Nuclear magnetic resonance spectrum (400 MHz, CDCl$_3$) δ ppm: 1.27(3H,d,J=7.3Hz), 1.37(3H,d,J=6.2Hz), 1.49–2.83 (5H,m), 2.31,2.35(3H,s2), 2.95–3.80(13H,m), 4.20–4.30 (2H,m), 5.16–5.53(4H,m), 7.52(2H,d,J=8.8Hz), 7.64,7.65 (2H,dx 2,J=8.8Hz), 8.22,8.23(4H,dx2,J=8.8Hz).

(2) To a solution of the compound (0.46 g), which had been obtained in (1), in tetrahydrofuran (22 ml) and water (15 ml), a 10% palladium-carbon catalyst (0.93 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was purified by reversed-phase column chromatography ["Cosmosil 75C18-PREP" (NACALAI TESQUE, INC.), acetonitrile/water=4/96–8/92], followed by concentration by evaporation under reduced pressure and lyophilization, whereby the title compound (150 mg) was obtained as a powder.

Infrared absorption spectrum (KBr) ν max cm$^{-1}$: 1760, 1634, 1598, 1486, 1454, 1383, 1314, 1279, 1253, 1221, 1180, 1148, 1095.

Nuclear magnetic resonance spectrum (400 MHz, D$_2$O) δ ppm: 1.21(3H,d,J=7.2Hz), 1.30(3H,d,J=6.2Hz), 1.65–1.86 (2H,m), 2.15–2.30(1H,m), 2.38(3H,s), 2.57–3.00(2H,m), 3.10–3.99(12H,m), 4.18–4.29(2H,m).

EXAMPLE 5

(1R,5S,6S)-6-[(1R)-1-Hydroxyethyl]-1-methyl-2-[(2S,4S)-2-[(3S)-3-methylaminomethylpyrrolidin-1-ylcarbonyl]pyrrolidin-4-ylthio]-1-carbapen-2-em-3-carboxylic acid Stereoisomer of Exemplified Compound No. 1

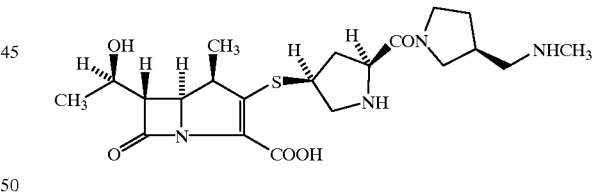

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.85 g) in anhydrous acetonitrile (5 ml), N,N-diisopropylethylamine (0.25 ml) and a solution of (2S,4S)-4-mercapto-2-[(3R)-3-(N-methyl-N-4-nitrobenzyloxycarbonylaminomethyl)pyrrolidin-1-ylcarbonyl]-1-(4-nitrobenzyloxycarbonyl)pyrrolidine (0.90 g) in anhydrous acetonitrile (10 ml) were added while stirring in an ice bath. The resulting mixture was stirred overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=95/5–9/1), whereby 4-nitrobenzyl (1R,5S,6S)-6-[(1R)-1-hydroxyethyl]-1-methyl-2-[(2S,4S)-2-[(3R)-3-(N-methyl- N-4-nitrobenzyloxycarbonylaminomethyl)-1-(4-nitrobenzyloxycarbonyl)pyrrolidin-1-ylcarbonyl]pyrrolidin-4-ylthio]-1-carbapen-2-em-3-carboxylate (1.07 g) was obtained.

Infrared absorption spectrum (KBr) ν max cm$^{-1}$: 1773, 1707, 1654, 1607, 1522, 1441, 1404, 1373, 1346, 1295, 1210, 1180, 1143, 1110, 1047, 1015.

Nuclear magnetic resonance spectrum (400 MHz, CDCl$_3$) δ ppm: 1.27(3H,d,J=7.3Hz), 1.37(3H,d,J=6.3Hz), 1.50–2.72 (5H,m), 2.90–4.3 1(14H,m), 4.40–4.55(1H,m), 5.01–5.52 (6H,m), 7.41–7.67(6H,m), 8.13–8.27(6H,m).

(2) To a solution of the compound (1.05 g), which had been obtained in (1), in tetrahydrofuran (50 ml) and water (35 ml), a 10% palladium-carbon catalyst (2.10 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was purified by reversed-phase column chromatography ["Cosmosil 75C18-PREP" (NACALAI TESQUE, INC.), acetonitrile/water=6/94–1/9], followed by concentration by evaporation under reduced pressure and lyophilization, whereby the title compound (127 mg) was obtained as a powder.

Infrared absorption spectrum (KBr) ν max cm$^{-1}$: 1756, 1633, 1598, 1457, 1387, 1311, 1285, 1258, 1226, 1181, 1149, 1096, 1074.

Nuclear magnetic resonance spectrum (400 MHz, D$_2$O) δ ppm: 1.22(3H,d,J=7.2Hz), 1.30(3H,d,J=6.4Hz), 1.59–1.87 (2H,m), 2.16–2.32(1H,m), 2.58–2.81(2H,m), 2.77(3H,s), 3.05–3.86(12H,m), 3.94–4.03(1H,m), 4.18–4.28(2H,m).

EXAMPLE 6

(1R,5S,6S)-6-[(1R)-1-Hydroxyethyl]-1-methyl-2-[(2S,4S)-2-[(3S)-3-methylaminomethylpyrrolidin-1-ylcarbonyl]-1-methylpyrrolidin-4-ylthio]-1-carbapen-2-em-3-carboxylic acid Stereoisomer of Exemplified Compound No. 62

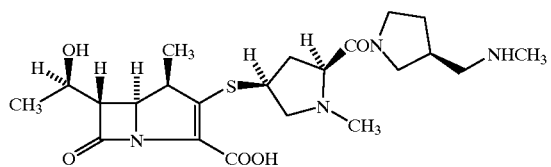

acetonitrile (5 ml) were added while stirring in an ice bath. The resulting mixture was allowed to react overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=6/4), whereby 4-nitrobenzyl (1R,5S,6S)-6-[(1R)-1-hydroxyethyl]-1-methyl-2-[(2S,4S)-1-methyl-2-[(3R)-3-(N-methyl-N-4-nitrobenzyloxycarbonylaminomethyl)pyrrolidin-1-ylcarbonyl]pyrrolidin-4-ylthio]-1-carbapen-2-em-3-carboxylate (0.43 g) was obtained.

Infrared absorption spectrum (KBr) ν max cm$^{-1}$: 1771, 1734, 1705, 1639, 1608, 1522, 1489, 1452, 1403, 1375, 1346, 1278, 1246, 1210, 1142.

Nuclear magnetic resonance spectrum (400 MHz, CDCl$_3$) δ ppm: 1.27(3H,d,J=7.2Hz), 1.37(3H,d,J=6.2Hz), 1.52–2.78 (8H,m), 2.94–3.82(13H,m), 4.19–4.30(2H,m), 5.12–5.50 (4H,m), 7.50–7.68(4H,m), 8.21–8.23(4H,m).

(2) To a solution of the compound (0.42 g), which had been obtained in (1), in tetrahydrofuran (20 ml) and water (15 ml), a 10% palladium-carbon catalyst (0.83 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was purified by reversed-phase column chromatography ["Cosmosil 75C18-PREP" (NACALAI TESQUE, INC.), acetonitrile/water=6/94–8/92], followed by concentration by evaporation under reduced pressure and lyophilization, whereby the title compound (28 mg) was obtained as a powder.

Infrared absorption spectrum (KBr) ν max cm$^{-1}$: 1757, 1642, 1597, 1489, 1457, 1384, 1251, 1210, 1158, 1095, 1028.

Nuclear magnetic resonance spectrum (400 MHz, D$_2$O) δ ppm: 1.21(3H,d,J=7.2Hz), 1.30(3H,d,J=6.4Hz), 1.67–1.88 (2H,m), 2.17–2.32(1H,m), 2.51(3H,br.s), 2.57–2.75(1H,m), 2.76(3H,s), 2.87–3.01(1H,m), 3.05–3.87(1 1H,m), 3.90–4.00(1H,m), 4.18–4.29(2H,m).

EXAMPLE 7

(1R,5S,6S)-2-[(2S,4S)-2-[(3R)-3-Guanidinomethylpyrrolidin-1-ylcarbonyl]pyrrolidin-4-ylthio]-6-[(1R)-1-hydroxyethyl]-1-methyl-1-carbapen-2-em-3-carboxylic acid Stereoisomer of Exemplified Compound No. 18

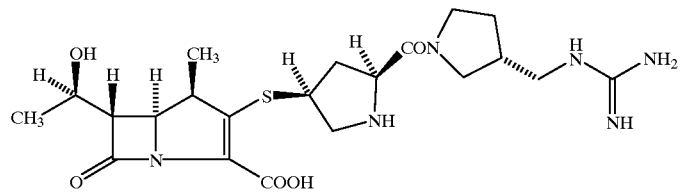

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.66 g) in anhydrous acetonitrile (5 ml), N,N-diisopropylethylamine (0.19 ml) and a solution of (2S,4S)-4-mercapto-1-methyl-2-[(3R)-3-(N-methyl-N-4-nitrobenzyloxycarbonylaminomethyl)pyrrolidin-1-ylcarbonyl]pyrrolidine (0.53 g) in anhydrous (1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.70 g) in anhydrous acetonitrile (10 ml), N,N-diisopropylethylamine (0.21 ml) and a solution of (2S,4S)-4-mercapto-1-(4-nitrobenzyloxycarbonyl)-2-[(3R)-3-(4-nitrobenzyloxycarbonylguanidinomethyl)pyrrolidin-1- ylcarbonyl]pyrrolidine (1.28 g) in anhydrous acetonitrile (10 ml) were added while stirring in an ice bath. The resulting mixture was allowed to react overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=95/5–9/1–6/4), whereby 4-nitrobenzyl (1R,5S,6S)-6-[(1R)-1-hydroxyethyl]-1-methyl-2-[(2S,4S)-1-(4-nitrobenzyloxycarbonyl)-2-[(3R)-3-(4-nitrobenzyloxycarbonylguanidinomethyl)pyrrolidin-1-ylcarbonyl]pyrrolidin-4-ylthio]-1-carbapen-2-em-3-carboxylate (0.97 g) was obtained.

Infrared absorption spectrum (KBr) ν max cm$^{-1}$: 1772, 1709, 1647, 1608, 1522, 1491, 1440, 1404, 1378, 1346, 1322, 1287, 1210, 1178, 1133, 1109.

Nuclear magnetic resonance spectrum (270 MHz, CDCl$_3$) δ ppm: 1.28(3H,d,J=7.4Hz), 1.37(3H,d,J=6.3Hz), 1.50–2.77(8H,m), 2.94–4.05(12H,m), 4.18–4.28(2H,m), 4.40–4.55(1H,m), 5.10–5.51(6H,m), 7.37–7.68(6H,m), 8.10–8.27(6H,m).

(2) To a solution of the compound (0.95 g), which had been obtained in (1), in tetrahydrofuran (50 ml) and water (35 ml), a 10% palladium-carbon catalyst (1.90 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was purified by reversed-phase column chromatography ["Cosmosil 75C18-PREP" (NACALAI TESQUE, INC.), acetonitrile/water=8/92–12/88], followed by concentration by evaporation under reduced pressure and lyophilization, whereby crude title compound (224 mg) was obtained as a powder.

The crude title compound was purified through an HPLC preparative column ["Cosmosil 5C 18-AR" (NACALAI TESQUE, INC.), acetonitrile/water=8/92–12/88], followed by concentration by evaporation under reduced pressure and lyophilization, whereby the title compound (166 mg) was obtained as a powder.

Infrared absorption spectrum (KBr) ν max cm$^{-1}$: 1757, 1630, 1455, 1386, 1313, 1283, 1260, 1224, 1182, 1147, 1102, 1074.

Nuclear magnetic resonance spectrum (400 MHz, D$_2$O) δ ppm: 1.22(3H,d,J=7.2Hz), 1.30(3H,d,J=6.2Hz), 1.55–1.84 (2H,m), 2.18–2.23(1H,m), 2.52–2.78(2H,m), 3.06(1H,dd,J=12.3,3.6Hz), 3.13–3.85(10H,m), 3.96–4.03(1H,m), 4.18–4.29(2H,m).

EXAMPLE 8

(1R,5S,6S)-2-[(2S,4S)-2-[(3R)-3-Acetimidoylaminomethylpyrrolidin-1-ylcarbonyl]pyrrolidin-4-ylthio]-6-[(1R)- 1-hydroxyethyl]-1-methyl-1-carbapen-2-em-3-carboxylic acid Stereoisomer of Exemplified Compound No. 17

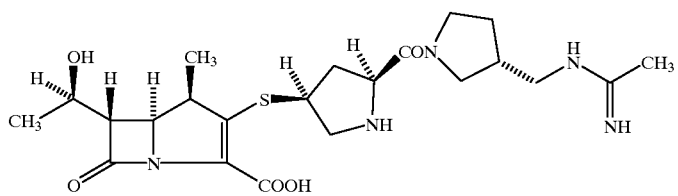

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.81 g) in anhydrous acetonitrile (10 ml), N,N-diisopropylethylamine (0.44 ml) and a solution of (2S,4S)-4-mercapto-1-(4-nitrobenzyloxycarbonyl)-2-[(3R)-3-(4-nitrobenzyloxycarbonylacetimidoylaminomethyl)pyrrolidin-1-ylcarbonyl]pyrrolidine (1.35 g) in anhydrous acetonitrile (15 ml) were added while stirring in an ice bath. The resulting mixture was allowed to react overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=95/5–9/1–8/2), whereby 4-nitrobenzyl (1R,5S,6S)-6-[(1R)-1-hydroxyethyl]-1-methyl-2-[(2S,4S)- 1-(4-nitrobenzyloxycarbonyl)-2-[(3R)-3-(4-nitrobenzyloxycarbonylacetimidoaminomethyl)pyrrolidin-1-ylcarbonyl]pyrrolidin-4-ylthio]-1-carbapen-2-em-3-carboxylate (1.15 g) was obtained.

Infrared absorption spectrum (KBr) ν max cm$^{-1}$: 1773, 1709, 1650, 1607, 1556, 1522, 1494, 1441, 1404, 1373, 1246, 1278, 1237, 1212, 1126, 1110.

Nuclear magnetic resonance spectrum (400 MHz, CDCl$_3$) δ ppm: 1.29(3H,d,J=7. 1Hz), 1.37(3H,d,J=6. 1Hz), 1.50–2.72(9H,m), 2.98–4.06(12H,m), 4.22–4.30(2H,m), 4.46–4.57(1H,m), 5.16–5.52(6H,m), 7.43–7.67(6H,m), 8.17–8.27(6H,m).

(2) To a solution of the compound (1.13 g), which had been obtained in (1), in tetrahydrofuran (60 ml) and water (42 ml), a 10% palladium-carbon catalyst (2.28 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was purified by reversed-phase column chromatography ["Cosmosil 75C18-PREP" (NACALAI TESQUE, INC.), acetonitrile/water=8/92–12/88], followed by concentration by evaporation under reduced pressure and lyophilization, whereby a compound (337 mg) was obtained as a powder.

The resulting compound was purified through an BPLC preparative column ["Cosmosil 5C18-AR" (NACALAI TESQUE, INC.), acetonitrile/water=8/92–12/88], followed by concentration by evaporation under reduced pressure and lyophilization, whereby the title compound (254 mg) was obtained as a powder.

Infrared absorption spectrum (KBr) ν max cm$^{-1}$: 1756, 1684, 1633, 1593, 1455, 1386, 1312, 1284, 1261, 1226, 1182, 1284, 1261, 1226, 1182, 1148.

Nuclear magnetic resonance spectrum (400 MHz, D$_2$O) δ ppm: 1.22(3H,d,J=7.2Hz), 1.30(3H,d,J=6.4Hz), 1.56–1.67 (1H,m), 1.69–1.87(1H,m), 2.12–2.26(1H,m), 2.25(3H,s), 2.58–2.78(2H,m), 3.06(1H,dd,J=12.3,3.5Hz), 3.14–3.85 (10H,m), 3.96–4.04(1H,m), 4.18–4.28(2H,m).

EXAMPLE 9

(1R,5S,6S)-2-[(2S,4S)-2-[(3R)-3-Cyclopropylaminomethylpyrrolidin-1-ylcarbonyl] pyrrolidin-4-ylthio]-6-[(1R)-1-hydroxyethyl]-1-methyl-1-carbapen-2-em-3-carboxylic acid Stereoisomer of Exemplified Compound No. 15

Nuclear magnetic resonance spectrum (400 MHz, CDCl$_3$) δ ppm: 0.60–0.92(4H,m), 1.29(3H,dxJ=7.4Hz), 1.37, 1.38 (3H,dx2,J=6.3Hz), 1.48–2.74(6H,m), 3.00–4.05(1H,m), 4.22–4.30(2H,m), 4.36–4.56(1H,m), 5.16–5.52(6H,m), 7.43–7.68(6H,m), 8.17–8.26(6H,m).

(2) To a solution of the compound (0.78 g), which had been obtained in (1), in tetrahydrofuran (40 ml) and water (28 ml), a 10% palladium-carbon catalyst (1.57 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was purified by reversed-phase column chromatography ["Cosmosil 75C18-PREP" (NACALAI TESQUE, INC.), acetonitrile/water=6/94–1/9], followed by concentration by evaporation under reduced pressure and lyophilization, whereby the title compound (106 mg) was obtained as a powder.

Infrared absorption spectrum (KBr) ν max cm$^{-1}$: 1759, 1637, 1599, 1455, 1386, 1312, 1283, 1259, 1224, 1180, 1147, 1103.

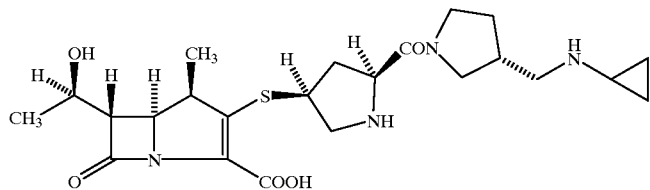

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.66 g) in anhydrous acetonitrile (7 ml), N,N-diisopropylethylamine (0.19 ml) and a solution of (2S,4S)-4-mercapto-1-(4-nitrobenzyloxycarbonyl)-2-[(3S)-3-(N-cyclopropyl-N-4-nitrobenzyloxycarbonylaminomethyl)pyrrolidin-1-ylcarbonyl]pyrrolidine (0.14 g) in anhydrous acetonitrile (8 ml) were added while stirring in an ice bath. The resulting mixture was allowed to react overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=95/5), whereby 4-nitrobenzyl (1R,5S,6S)-6-[(1R)-1-hydroxyethyl]-1-methyl-2-[(2S,4S)-1-(4-nitrobenzyloxycarbonyl)-2-[(3S)-3-(N-cyclopropyl-N-4-nitrobenzyloxycarbonylaminomethyl) pyrrolidin-1-ylcarbonyl]pyrrolidin-4-ylthio]-1-carbapen-2-em-3-carboxylate (0.80 g) was obtained.

Infrared absorption spectrum (KBr) ν max cm$^{-1}$: 1774, 1708, 1652, 1607, 1522, 1496, 1444, 1404, 1346, 1287, 1210, 1181, 1138, 1110.

Nuclear magnetic resonance spectrum (400 MHz, D$_2$O) δ ppm: 0.73–0.88(4H,m), 1.22(3H,d,J=7.2Hz), 1.30(3H,d,J= 6.4Hz), 1.63–1.86(2H,m), 2.14–2.30(1H,m), 2.58–2.83(3H, m), 3.08–3.92(1H,m), 4.06–4.14(1H,m), 4.19–4.30(2H,m).

EXAMPLE 10

(1R,5S,6S)-2-[(2S,4S)-2-[(3S)-3-Acetimidoylaminomethylpyrrolidin-1-ylcarbonyl] pyrrolidin-4-ylthio]-6-[(1R)-1-hydroxyethyl]-1-methyl-1-carbapen-2-em-3-carboxylic acid Stereoisomer of Exemplified Compound No. 17

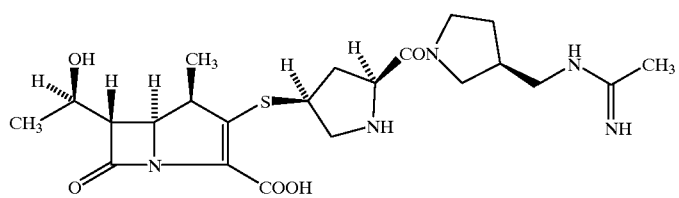

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (0.58 g) in anhydrous acetonitrile (10 ml), N,N-diisopropylethylamine (0.17 ml) and a solution of (2S,4S)-4-mercapto-1-(4-nitrobenzyloxycarbonyl)-2-[(3S)-3-(4-nitrobenzyloxycarbonylacetimidoylaminomethyl)pyrrolidin-1-ylcarbonyl]pyrrolidine (0.93 g) in anhydrous acetonitrile (10 ml) were added while stirring in an ice bath. The resulting mixture was stirred overnight at 0° C. To the reaction mixture, ethyl acetate was added. The resulting mixture was washed with water and saturated saline solution, dried over anhydrous sodium sulfate and then concentrated by evaporation under reduced pressure. The residue was purified by chromatography through a silica gel column (ethyl acetate/methanol=9/1), whereby 4-nitrobenzyl (1R,5S,6S)-6-[(1R)-1-hydroxyethyl]-1-methyl-2-[(2S,4S)-I-(4-nitrobenzyloxycarbonyl)-2-[(3S)-3-(4-nitrobenzyloxycarbonylacetimidoylaminomethyl)pyrrolidin-1-ylcarbonyl]pyrrolidin-4-ylthio]-1-carbapen-2-em-3-carboxylate (0.61 g) was obtained.

Infrared absorption spectrum (KBr) ν max cm$^{-1}$: 1774, 1709, 1651, 1607, 1558, 1522, 1496, 1441, 1404, 1373, 1346, 1278, 1238, 1212, 1126, 1110, 1074, 1015.

Nuclear magnetic resonance spectrum (400 MHz, CDCl$_3$) δ ppm: 1.29(3H,d,J=7.1 Hz), 1.37(3H,d,J=6.2Hz), 1.55–2.75(9H,m), 3.05–4.06(1 1H,m), 4.22–4.27(2H,m), 4.44–4.60(1H,m), 5.17–5.53(6H,m), 7.42–7.68(6H,m), 8.15–8.26(6H,m).

(2) To a solution of the compound (0.58 g), which had been obtained in (1), in tetrahydrofuran (30 ml) and water (20 ml), a 10% palladium-carbon catalyst (1.15 g) was added. The resulting mixture was allowed to absorb hydrogen for 1.5 hours while stirring at an external temperature of 30° C. The catalyst was then filtered off. The filtrate was washed with ether and ethyl acetate, followed by concentration by evaporation under reduced pressure. The residue was purified by reversed-phase column chromatography ["Cosmosil 75C18-PREP" (NACALAI TESQUE, INC.), acetonitrile/water=6/94–1/9], followed by concentration by evaporation under reduced pressure and lyophilization, whereby the title compound (156 mg) was obtained as a powder.

Infrared absorption spectrum (KBr) ν max cm$^{-1}$: 1756, 1687, 1633, 1592, 1454, 1386, 1313, 1284, 1261, 1226, 1182.

Nuclear magnetic resonance spectrum (400 MHz, D$_2$O) δ ppm: 1.22(3H,d,J=7.2Hz), 1.30(3H,d,J=6.2Hz), 1.57–1.67 (1H,m), 1.70–1.85(1H,m), 2.12–2.27(1H,m), 2.25(3H,s), 2.58–2.79(2H,m), 3.03–3.85(1H,m), 3.92–4.01(1H,m), 4.18–4.29(2H,m).

EXAMPLE 11

(1R,5S,6S)-2-[(2S,4S)-2-[(3S)-3-Guanidinomethylpyrrolidin-1-ylcarbonyl]pyrrolidin-4-ylthio]-6-[(1R)-1-hydroxyethyl]-1-methyl-1-carbapen-2-em-3-carboxylic acid Stereoisomer of Exemplified Compound No. 18

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (874 mg) in anhydrous acetonitrile (9 ml), N,N-diisopropylethylamine (0.256 ml) and a solution of (2S,4S)-4-mercapto-1-(4-nitrobenzyloxycarbonyl)-2-[(3S)-3-(4-nitrobenzyloxycarbonylguanidinomethyl)pyrrolidin-1-ylcarbonyl]pyrrolidine (926 mg) in anhydrous acetonitrile (1.0 ml) were added while stirring in an ice bath. The resulting mixture was stirred overnight at 0° C. To the reaction mixture, ethyl acetate was added. The resulting mixture was washed with water and saturated saline solution, dried over anhydrous sodium sulfate and then concentrated by evaporation under reduced pressure.

The residue was purified by chromatography through a silica gel column (ethyl acetate/methanol=7/1), whereby 4-nitrobenzyl (1R,5S,6S)-6-[(1R)-1-hydroxyethyl]-1-methyl-2-[(2S,4S)-1-(4-nitrobenzyloxycarbonyl)-2-[(3S)-3-(4-nitrobenzyloxycarbonylguanidinomethyl)pyrrolidin-1-ylcarbonyl]pyrrolidin-4-ylthio]-1-carbapen-2-em-3-carboxylate (1.23 g) was obtained.

Infrared absorption spectrum (KBr) ν max cm$^{-1}$: 1773, 1710, 1656, 1607, 1521, 1438, 1404, 1385, 1346, 1285, 1208, 1177, 1135, 1109, 1030.

Nuclear magnetic resonance spectrum (400 MHz, CDCl$_3$) δ ppm: 1.28(3H,d,J=7.2Hz), 1.34(3H,d,J=6.3Hz), 1.65–1.85 (1H,m), 1.90–2.10(2H,m), 2.15–2.80(5H,m), 3.05–3.70(1 1H,m), 4.00–4.10(1H,m), 4.10–4.30(2H,m), 4.45–4.60(1H, m), 5.00–5.55(6H,m), 7.40–7.70(6H,m), 8.15–8.30(6H,m).

(2) To a solution of the compound (1.14 g), which had been obtained in (1), in tetrahydrofuran (38 ml) and water (19 ml), a 10% palladium-carbon catalyst (2.3 g) was added. The resulting mixture was allowed to absorb hydrogen for 1.2 hours while stirring at an external temperature of 30° C. The catalyst was then filtered off. The filtrate was washed with ether, followed by concentration by evaporation under reduced pressure. The residue was purified by reversed-phase column chromatography ["Cosmosil 75C18-PREP" (NACALAI TESQUE, INC.), acetonitrile/water=8/92], followed by concentration by evaporation under reduced pressure and lyophilization, whereby the title compound (187 mg) was obtained as a powder.

Nuclear magnetic resonance spectrum (270 MHz, D$_2$O, sodium trimethylsilylpropionate-d4 as internal standard) δ ppm: 1.25(3H,d,J=7.0Hz), 1.33(3H,d,J=6.3Hz), 1.55–1.90 (2H,m), 2.10–2.30(1H,m), 2.50–2.90(2H,m), 3.05–3.35(4H, m), 3.35–3.50(3H,m), 3.60–3.75(2H,m), 3.78–3.90(1H,m), 3.90–4.10(1H,m), 4.20–4.35(2H,m).

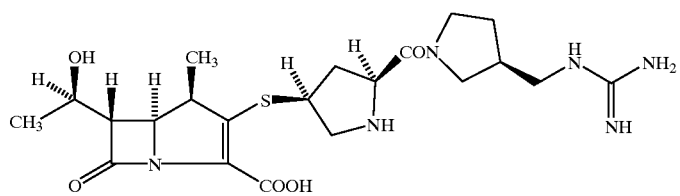

EXAMPLE 12

(1R,5S,6S)-6-[(1R)-1-Hydroxyethyl]-1-methyl-2-[(2S,4S)-2-[(3R)-3-(pyrrolidin-1-ylmethyl)pyrrolidin-1-ylcarbonyl]pyrrolidin-4-ylthio]-1-carbapen-2-em-3-carboxylic acid Stereoisomer of Exemplified Compound No. 54

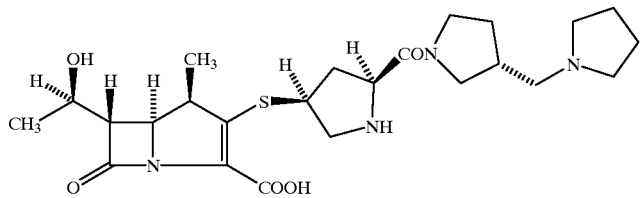

(1) To a solution of 4-nitrobenzyl (1R,5R,6S)-2-(diphenylphosphoryloxy)-6-[(1R)-1-hydroxyethyl]-1-methyl-1-carbapen-2-em-3-carboxylate (225 mg) in anhydrous dimethylformamide (3 ml), a solution of (2S,4S)-4-mercapto-1-(4-nitrobenzyloxycarbonyl)-2-[(3R)-3-(pyrrolidin-1-ylmethyl)pyrrolidin-1-ylcarbonyl]pyrrolidine (198 ml) in anhydrous dimethylformamide (1 ml) and diisopropylethylamine (97 μl) were added in an ice bath. The resulting mixture was stirred for 20 hours at the same temperature. The reaction mixture was concentrated by evaporation under reduced pressure. The residue was dissolved in ethyl acetate. The resulting mixture was washed successively with water and saturated saline solution and dried over anhydrous sodium sulfate. The solvent was then distilled off. The residue was subjected to chromatography through a silica gel column and from the fraction eluted with ethyl acetate/methanol=4/1, 4-nitrobenzyl (1R,5S,6S)-6-[(1R)-1-hydroxyethyl]-1-methyl-2-[(2S,4S)-1-(4-nitrobenzyloxycarbonyl)-2-[(3R)-3-(pyrrolidin-1-ylmethyl)pyrrolidin-1-ylcarbonyl]pyrrolidin-4-ylthio]-1-carbapen-2-em-3-carboxylate (235 mg) was obtained as a powder.

Infrared absorption spectrum (KBr) ν max cm$^{-1}$: 3351, 2970, 1773, 1709, 1697, 1525, 1447, 1246.

Nuclear magnetic resonance spectrum (270 MHz, CDCl$_3$) δ ppm: 1.20–1.30(3H, m), 1.34(3H, d, J=6.1Hz), 1.40–2.10 (6H, m), 2.00–3.00(8H, m), 3.10–3.80(6H, m), 3.80–4.40 (4H, m), 4.50–4.70(1H, m), 5.00–5.40(3H, m), 5.40–5.55 (1H, m), 7.40–7.55(2H, m), 7.60–7.70(2H, m), 8.15–8.25 (4H, m).

(2) The compound (161 mg) obtained in (1) was dissolved in tetrahydrofuran (3 ml)-water (1.5 ml), followed by the addition of a 10% palladium-carbon catalyst (320 mg). The resulting mixture was hydrogenated at room temperature for 90 minutes. The catalyst was then filtered off. The filtrate was concentrated by evaporation under reduced pressure to remove tetrahydrofuran. The residue was washed by ether and the water layer was concentrated by evaporation under reduced pressure. The residue was subjected to reversed-phase column chromatography ("Cosmosil 75C18-PREP" produced by NACALAI TESQUE, INC.) and the fraction eluted with acetonitrile/water=2/98–1/9 was lyophilized, whereby the title compound (51 mg) was obtained as a powder.

Infrared absorption spectrum (KBr) ν max cm$^{-1}$: 3378, 1763, 1655, 1593, 1489, 1376.

Nuclear magnetic resonance spectrum (400 MHz, D$_2$O) δ ppm: 1.20(3H, d, J=7.2Hz), 1.28(3H, d, J=6.4Hz), 1.65–1.90 (2H, m), 1.95–2.40(9H, m), 2.65–2.80(1H, m), 3.00–3.25 (3H, m), 3.30–3.40(2H, m), 3.40–3.55(2H, m), 3.60–4.00 (4H, m), 4.00–4.10(1H, m), 4.20–4.30(2H, m), 4.65–4.75 (1H, m).

EXAMPLE 13

(1R,5S,6S)-6-[(1R)-1-Hydroxyethyl]-2-[(2S,4S)-2-[(3S)-3-(2-hydroxyethylaminomethyl)pyrrolidin-1-ylcarbonyl]pyrrolidin-4-ylthio]-1-methyl-1-carbapen-2-em-3-carboxylic acid Stereoisomer of Exemplified Compound No. 3

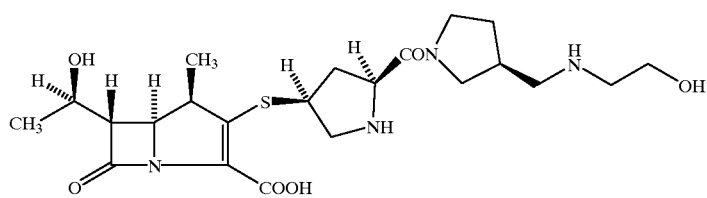

(2S,4S)-2-[(3R)-3-(N-2-Hydroxyethyl-N-4-nitrobenzyloxycarbonylaminomethyl)pyrrolidin-1-ylcarbonyl]-4-mercapto-1-(4-nitrobenzyloxycarbonyl)pyrrolidine (214 mg) was treated in a similar manner to that described in Example 12-(1) and (2), to afford the title compound (85.1 mg) as a powder.

Infrared absorption spectrum (KBr) ν max cm$^{-1}$: 3409, 1747, 1644, 1601, 1455, 1386.

Nuclear magnetic resonance spectrum (400 MHz, D$_2$O) δ ppm: 1.22(3H, d, J=7.2Hz), 1.30(3H, d, J=6.4Hz), 1.70–1.95 (21, m), 2.15–2.35(21, m), 2.60–2.85(2H, m), 2.85–2.95(11, m), 3.15–3.30(31, m), 3.30–3.50(51, m), 3.55–3.90(2H, m), 3.90–4.00(1H, m), 4.20–4.40(5H, m).

EXAMPLE 14

(1R,5S,6S)-2-[(2S,4S)-2-[(3R)-3-(Carbamoylmethylaminomethyl)pyrrolidin-1-ylcarbonyl]pyrrolidin-4-ylthio]-6-[(1R)-1-hydroxyethyl]-1-methyl]-1-carbapen-2-em-3-carboxylic acid Stereoisomer of Exemplified Compound No. 6

(2S,4S)-2-[(3S)-3-(N-Carbamoylmethyl-N-4-nitrobenzyloxycarbonylaminomethyl)pyrrolidin-1-ylcarbonyl]-4-mercapto-1-(4-nitrobenzyloxycarbonyl)pyrrolidine (368 mg) was treated in a similar manner to that described in Example 12-(1) and (2), to give the title compound (158 mg) as a powder.

Infrared absorption spectrum (KBr) ν max cm$^{-1}$: 3401, 1754, 1695, 1645, 1597, 1455.

Nuclear magnetic resonance spectrum (400 MHz, D$_2$O) δ ppm: 1.22(3H, d, J=7.2Hz), 1.30(3H, d, J=6.4Hz), 1.70–1.90 (1H, m), 1.90–2.05(1H, m), 2.20–2.35(1H, m), 2.65–2.80 (1H, m), 2.95–3.10(1H, m), 3.10–3.22(2H, m), 3.22–3.30 (1H, m), 3.35–3.60(4H, m), 3.60–3.95(5H, m), 4.00–4.08 (1H, m), 4.22–4.30(211, m), 4.60–4.70(1H, m).

EXAMPLE 15

(1R,5S,6S)-2-[(2S,4S)-2-[(3R)-3-(2-Aminoethylaminomethyl)pyrrolidin-1-ylcarbonyl]pyrrolidin-4-ylthio]-6-[(1R)-1-hydroxyethyl]-1-methyl-1-carbapen-2-em-3-carboxylic acid Stereoisomer of Exemplified Compound No. 12

(2S,4S)-4-Mercapto-1-(4-nitrobenzyloxycarbonyl)-2-[(3S)-3-(N-2-(4-nitrobenzyloxycarbonylamino)ethyl-N-4-nitrobenzyloxycarbonylaminomethyl)pyrrolidin-1-ylcarbonyl]pyrrolidine (248 mg) was treated in a similar manner to that described in Example 12-(1) and (2), to afford the title compound (48.5 mg) as a powder.

Infrared absorption spectrum (KBr) ν max cm$^{-1}$: 3370, 1758, 1648, 1603, 1455, 1386.

Nuclear magnetic resonance spectrum (400 MHz, D$_2$O) δ ppm: 1.22(3H, d, J=7.2Hz), 1.30(3H, d, J=6.4Hz), 1.70–1.90 (1H, m), 1.90–2.05(1H, m), 2.15–2.33(1H, m), 2.55–2.70 (1H, m), 2.97–3.13(4H, m), 3.15–3.33(5H, m), 3.34–3.52 (3H, m), 3.57–3.67(1H, m), 3.68–3.90(3H, m), 4.21–4.30 (2H, m), 4.60–4.67(1H, m).

EXAMPLE 16

(1R,5S,6S)-2-[(2S,4S)-2-[(3R)-3-(2-Dimethylaminoethylaminomethyl)pyrrolidin-1-ylcarbonyl]pyrrolidin-4-ylthio]-6-[(1R)-1-hydroxyethyl]-1-methyl-I-carbapen-2-em-3-carboxylic acid Stereoisomer of Exemplified Compound No. 14

(2S,4S)-2-[(3S)-3-(N-2-Dimethylaminoethyl-N-4-nitrobenzyloxycarbonylaminomethyl)pyrrolidin-1-ylcarbonyl]-4-mercapto-1-(4-nitrobenzyloxycarbonyl) pyrrolidine (428 mg) was treated in a similar manner to that described in Example 12-(1) and (2), to give the title compound (109 mg) as a powder.

Nuclear magnetic resonance spectrum (270 MHz, D$_2$O) δ ppm: 1.22(3H, d, J=7.2Hz), 1.30(3H, d, J=6.3Hz), 1.60–1.90 (2H, m), 2.10–2.25(1H, m), 2.45–2.60(1H, m), 2.77(3H, s), 2.79(3H, s), 2.70–3.00(2H, m), 3.00–3.10(1H, m), 3.31–3.53(5H, m), 3.55–3.87(3H, m), 3.88–4.00(1H, m), 4.20–4.30(2H, m), 4.30–4.40(1H, m).

EXAMPLE 17

(1R, 5S,6S)-6-[(1R)-1-Hydroxyethyl]-1-methyl-2-[(2S,4S)-2-[(3R)-3-(N-methyl-N-2-methylaminoethylaminomethyl)pyrrolidin-1-ylcarbonyl]pyrrolidin-4-ylthio]-1-carbapen-2-em-3-carboxylic acid hydrochloride Hydrochloride of the Stereoisomer of Exemplified Compound No. 31 layer was concentrated by evaporation under reduced pressure. The residue was subjected to reversed-phase column chromatography ("Cosmosil 75C18-PREP" produced by NACALAI TESQUE, INC.) and the fraction eluted with water was lyophilized, to afford the title compound (61 mg) as a powder.

Nuclear magnetic resonance spectrum (400 MHz, D$_2$O) δ ppm: 1.21(3H, d, J=7.2Hz), 1.29(3H, d, J=6.3Hz), 1.70–1.87 (1H, m), 1.96–2.05(1H, m), 2.22–2.34(1H, m), 2.60–2.69 (1H, m), 2.75(3H, s), 2.90(3H, s), 3.00–3.10(1H, m), 3.10–3.35(7H, m), 3.35–3.44(1H, m), 3.45–3.60(3H, m), 3.62–3.92(3H, m), 4.01–4.08(1H, m), 4.20–4.27(2H, m), 4.65–4.79(1H, m).

EXAMPLE 18

(1R,5S,6S)-2-[(2S,4S)-2-[(3R)-3-(2-Fluoroethylaminomethyl)pyrrolidin-1-ylcarbonyl]pyrrolidin-4-ylthio]-6-[(1R)-1-hydroxyethyl]-1-methyl-1-carbapen-2-em-3-carboxylic acid Stereoisomer of Exemplified Compound No. 4

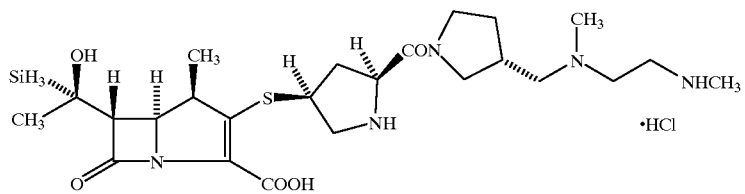

(1) (2S,4S)-4-Mercapto-2-[(3R)-3-[N-2-(N-methyl-N-4-nitrobenzyloxycarbonylamino)ethyl-N-methylaminomethyl]pyrrolidin-1-ylcarbonyl]-1-(4-nitrobenzyloxycarbonyl)pyrrolidine (617 mg) was treated in a similar manner to that described in Example 12-(1), to afford 4-nitrobenzyl (1R,5S,6S)-6-[(1R)-1-hydroxyethyl]-1-methyl-2-[(2S,4S)-1-(4-nitrobenzyloxycarbonyl)-2-[(3R)-3-[N-2-(N-methyl-N-4-nitrobenzyloxycarbonylamino) ethyl-N-methylaminomethyl]pyrrolidin 1-ylcarbonyl] pyrrolidin-4-ylthio]-1-carbapen-2-em-3-carboxylate (527 mg) as a powder.

(2) The compound (202 mg) obtained in (1) was dissolved in water (1.5 ml), 1N hydrochloric acid (0.201 ml) and tetrahydrofuran (3 ml), followed by the addition of a 10% palladium-carbon catalyst (400 mg). The resulting mixture was hydrogenated at room temperature for 45 minutes. The catalyst was then filtered off. The filtrate was concentrated by evaporation under reduced pressure to remove tetrahydrofuran. The residue was washed by ether and the water (2S,4S)-2-[(3S)-3-(N-2-Fluoroethyl-N-4-nitrobenzyloxycarbonylaminomethyl)pyrrolidin-1-ylcarbonyl]-4-mercapto-1-(4-nitrobenzyloxycarbonyl)pyrrolidine can be treated in a similar manner to that described in Example 12-(1) and (2), to afford the title compound.

EXAMPLE 19

(1R,5S,6S)-2-[(2S,4S)-2-[(3R)-3-(1-Methylguanidinomethyl)pyrrolidin-1-ylcarbonyl]pyrrolidin-4-ylthio-6-[(1R)-1-hydroxyethyl]-1-methyl-1-carbapen-2-em-3-carboxylic acid Stereoisomer of Exemplified Compound No. 36

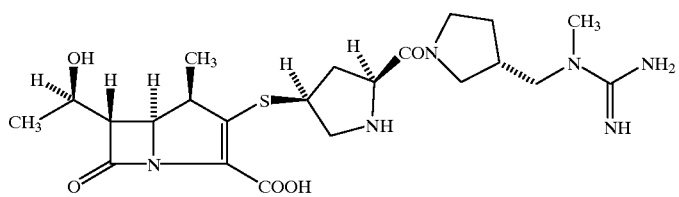

(2S,4S)-4-Mercapto-2-[(3R)-3-[1-methyl-2,3-bis(4-nitrobenzyloxycarbonyl)guanidinomethyl]pyrrolidin-1-ylcarbonyl]-1-(4-nitrobenzyloxycarbonyl)pyrrolidine (996 mg) was treated in a similar manner to that described in Example 12-(1) and (2), to afford the title compound (149 mg).

Nuclear magnetic resonance spectrum (400 MHz, $D_2O$) δ ppm: 1.22(3H, d, J=7.2Hz), 1.30(3H, d, J=6.4Hz), 1.55–1.70 (1H, m), 1.70–1.85(1H, m), 2.10–2.25(1H, m), 2.65–2.80 (2H, m), 3.09(31H, s), 3.15–3.30(2H, m), 3.35–3.55(6H, m), 3.70–3.85(2H, m), 3.95–4.05(1H, m), 4.20–4.30(21 m).

EXAMPLE 20

(1R,5S,6S)-2-[(2S,4S)-2-[(3R)-3-(N-Acetimidoyl-N-methylaminomethyl)pyrrolidin-1-ylcarbonyl]pyrrolidin-4-ylthio]-6-[(1R)-1-hydroxyethyl]-1-methyl-I-carbapen-2-em-3-carboxylic acid Stereoisomer of Exemplified Compound No. 35

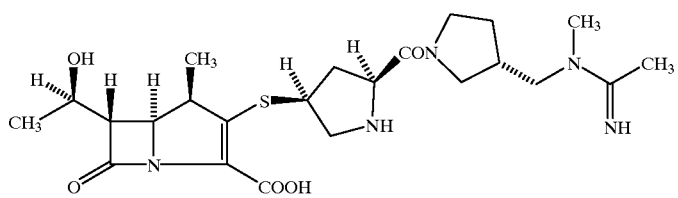

(2S,4S)-4-Mercapto-1-(4-nitrobenzyloxycarbonyl)-2-[(3R)-3-(N-4-nitrobenzyloxycarbonylacetimidoyl-N-methylaminomethyl)pyrrolidin-1-ylcarbonyl]pyrrolidine can be treated in a similar manner to that described in Example 12-(1) and (2), to afford the title compound.

EXAMPLE 21

(1R, 5S,6S)-2-[(2S,4S)-2-[(3R)-3-(N-Formimidoyl-N-methylaminomethyl)pyrrolidin-1-ylcarbonyl]pyrrolidin-4-ylthio]-6-[(1R)-1-hydroxyethyl]-1-methyl-1-carbapen-2-em-3-carboxylic acid Stereoisomer of Exemplified Compound No. 34

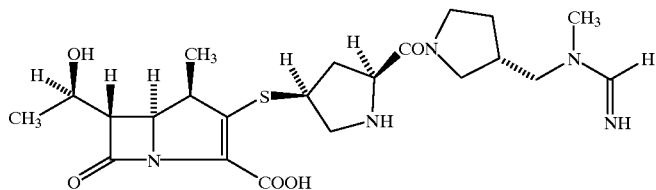

(2S,4S)-4-Mercapto-1-(4-nitrobenzyloxycarbonyl)-2-[(3R)-3-(N-4-nitrobenzyloxycarbonylformimidoyl-N-methylaminomethyl)pyrrolidin-1-ylcarbonyl]pyrrolidine can be treated in a similar manner to that described in Example 12-(1) and (2), to give the title compound.

EXAMPLE 22

(1R,5S,6S)-6-[(1R)-1-Hydroxyethyl]-1-methyl-2-[(2S,4S)-2-[(3R)-3-(2,2,2-trifluoroethylaminomethyl)pyrrolidin-1-ylcarbonyl]pyrrolidin-4-ylthio]-1-carbapen-2-em-3-carboxylic acid Stereoisomer of Exemplified Compound No. 5

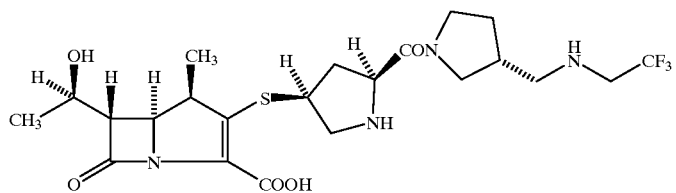

(2S,4S)-4-Mercapto-1-(4-nitrobenzyloxycarbonyl)-2-[(3S)-3-(N-4-nitrobenzyloxycarbonyl-N-2,2,2-trifluoroethylaminomethyl]pyrrolidin-1-ylcarbonyl]pyrrolidine can be treated in a similar manner to that described in Example 12-(1) and (2), to give the title compound.

EXAMPLE 23

(1R,5S,6S)-2-[(2S,4S)-2-[(3R)-3-Formimidoylaminomethylpyrrolidin-1-ylcarbonyl]pyrrolidin-4-ylthio]-6-[(1R)-1-hydroxyethyl]-1-methyl-1-carbapen-2-em-3-carboxylic acid Stereoisomer of Exemplified Compound No. 16

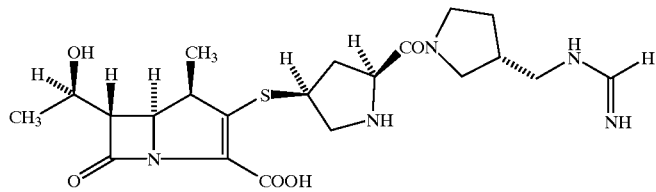

(2S,4S)-4-Mercapto-1-(4-nitrobenzyloxycarbonyl)-2-[(3R)-3-(4-nitrobenzyloxycarbonylformimidoylaminomethyl)pyrrolidin-1-ylcarbonyl]pyrrolidine can be treated in a similar manner to that described in Example 12-(1) and (2), to afford the title compound.

EXAMPLE 24

(1R, 5S,6S)-2-[(2S,4S)-2-[(3R)-3-Guanidinomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomer of Exemplified Compound No. 79

(2S,4S)-2-[(3R)-3-[2,3-bis(4-nitrobenzyloxycarbonyl)guanidinomethyl]pyrrolidin-1-ylcarbonyl]-4-mercapto-1-methylpyrrolidine can be treated in a similar manner to that described in Example 4-(1) and (2), to give title compound.

(2S,4S)-4-Mercapto-1-methyl-2-[(3R)-3-(N-4-nitrobenzyloxycarbonylacetimidoyl-N-methylaminomethyl)pyrrolidin-1-ylcarbonyl]pyrrolidine can be treated in a similar manner to that described in Example 4-(1) and (2), to afford the title compound.

EXAMPLE 26

(1R,5S,6S)-2-[(2S,4S)-2-[(3R)-3-Formimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomer of Exemplified Compound No. 77

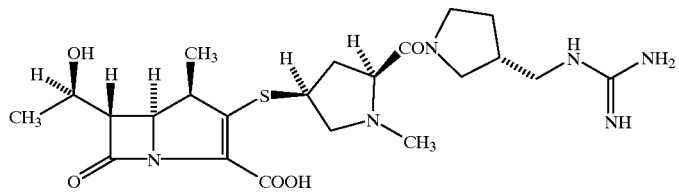

EXAMPLE 25

(1R,5S,6S)-2-[(2S,4S)-2-[(3R)-3-Acetimidoylaminomethylpyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomer of Exemplified Compound No. 78

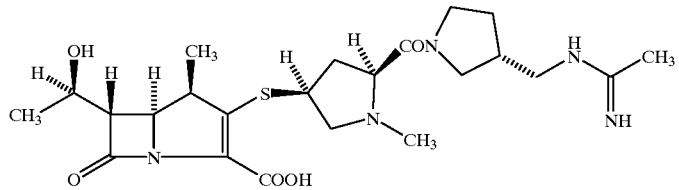

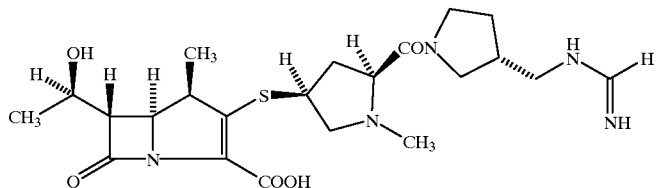

(2S,4S)-4-mercapto-1-methyl-2-[(3R)-3-(4-nitrobenzyloxycarbonylformimidoylaminomethyl)pyrrolidin-1-ylcarbonyl]pyrrolidine can be treated in a similar manner to that described in Example 4-(1) and (2), to give the title compound.

EXAMPLE 27

(1R,5S,6S)-2-[(2S,4S)-2-[(3R)-3-(1-Methylguanidinomethyl)pyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomer of Exemplified Compound No. 96

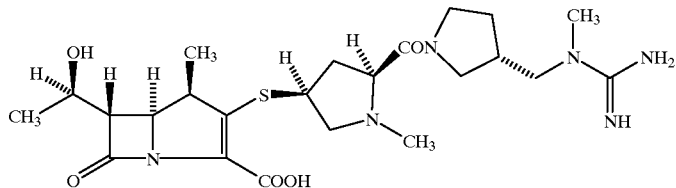

(2S,4S)-2-[(3R)-3-[2,3-Bis(4-nitrobenzyloxycarbonyl)-1-methylguanidinomethyl]pyrrolidin-1-ylcarbonyl]-4-mercapto-1-methylpyrrolidine can be treated in a similar manner to that described in Example 4-(1) and (2), to afford the title.

EXAMPLE 28

(1R,5S6S)-2-[(2S,4S)-2-[(3R)-3-(N-Acetimidoyl-N-methylaminomethyl)pyrrolidin-1-ylcarbonyl]-1-methylpyrrolidin-4-ylthio]-6-[(1R)-1-hydroxyethyl]-1-methyl-1-carbapen-2-em-3-carboxylic acid Stereoisomer of Exemplified Compound No. 95

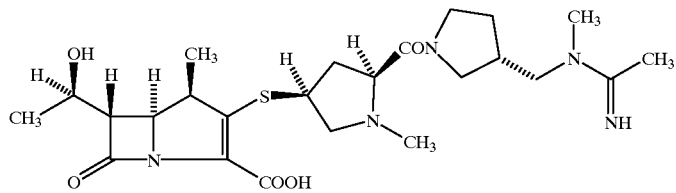

(2S,4S)-4-Mercapto-1-methyl-2-[(3R)-3-(N-4-nitrobenzyloxycarbonylacetimidoyl-N-methylaminomethyl)pyrrolidin-1-ylcarbonyl]pyrrolidine can be treated in a similar manner to that described in Example 4-(1) and (2), to give the title compound.

EXAMPLE 29

(1R,5S,6S)-2-[(2S,4S)-2-[(3R)-3-(N-Formimidoyl-N-methylaminomethyl)pyrrolidin-1-ylcarbonyl]-1-methylpyrrolidin-4-ylthio]-6-[(1R)-1-hydroxyethyl1–1-methyl-1-carbapen-2-em-3-carboxylic acid Stereoisomer of Exemplified Compound No. 94

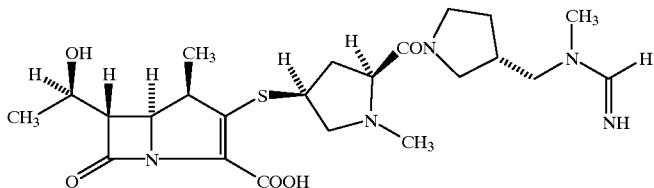

(2S,4S)-4-Mercapto-1-methyl-2-[(3R)-3-(N-4-nitrobenzyloxycarbonylformimidoyl-N-methylaminomethyl)pyrrolidin-1-ylcarbonyl]pyrrolidine can be treated in a similar manner to that described in Example 4-(1) and (2), to afford the title compound.

EXAMPLE 30

(1R, 5S,6S)-6-[(1R)-1-Hydroxyethyl]-1-methyl-2-[(2S,4S)-2-[(3R)-3-methylaminomethylpyrrolidin-1-ylcarbonyl]pyrrolidin-4-ylthio]-1-carbapen-2-em-3-carboxylic acid hydrochloride Hydrochloride of the Stereoisomer of Exemplified Compound No. 1

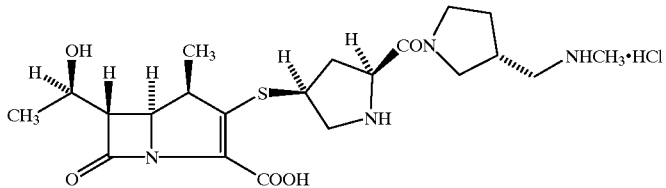

To an aqueous solution (2 ml) of (1R,5S,6S)-6-[(1R)-1-hydroxyethyl]-1-methyl-2-[(2S,4S)-2-[(3R)-3-methylaminomethylpyrrolidin-1-ylcarbonyl]pyrrolidin-4-ylthio]-1-carbapen-2-em-3-carboxylic acid (59.7 mg), obtained in Example 3, 1N hydrochloric acid (0.122 ml) was added. The resulting aqueous solution was subjected to reversed-phase column chromatography ("Cosmosil 75C18-PREP" produced by NACALAI TESQUE, INC.) and from the fraction eluted with water, the title compound (46 mg) was obtained as a powder.

Infrared absorption spectrum (KBr) ν max cm$^{-1}$: 3409, 1757, 1634, 1598, 1456, 1386.

Nuclear magnetic resonance spectrum (400 MHz, D$_2$O) δ ppm: 1.21(3H, d, J=7.2Hz), 1.29(3H, d, J=6.3Hz), 1.70–1.87 (1H, m), 1.96–2.05(1H, m), 2.20–2.32(1H, m), 2.60–2.70 (1H m), 2.75(3H,s), 3.00–3.10(1H, m), 3.10–3.35(3H, m), 3.35–3.45(1H, m), 3.45–3.50(3H,m), 3.60–3.90(3H,m), 4.02–4.09(1H, m), 4.21–4.28(2H, m), 4.66–4.78(1H,m).

REFERENTIAL EXAMPLE 1

(2S,4S)-4-Mercapto-1-methyl-2-[(3R)-3-(4-nitrobenzyloxycarbonylaminomethyl)pyrrolidin-1-ylcarbonyl]pyrrolidine (1) To a solution (240 ml) of (3S)-3-hydroxymethyl-1-[(1R)-1-phenylethyl]pyrrolidine (11.5 g) in ethanol, a palladium hydroxide-carbon catalyst (11.6 g) was added. The resulting mixture was allowed to absorb hydrogen for 3 hours while stirring at an external temperature of 40° C. The catalyst was then filtered off, followed by concentration by evaporation under reduced pressure. Into the residue (6.01 g), acetonitrile (60 ml) was poured and then di-tert-butyl carbonate (14 ml) was added to the resulting mixture in an ice bath. After the temperature of the reaction mixture was allowed to rise to room temperature, the mixture was stirred for one hour. Saturated saline solution was then poured into the reaction mixture to terminate the reaction, followed by extraction three times with ethyl acetate. The combined organic layer was washed with saturated saline solution, dried over anhydrous sodium sulfate and then concentrated by evaporation under reduced pressure. The residue was purified by chromatography through a silica gel column (ethyl acetate), whereby (3S)-1-tertbutoxycarbonyl-3-hydroxymethylpyrrolidine (8.66 g) was obtained.

Optical rotation: [α]$_D^{25}$=–16.5° (C=1.0, CHCl$_3$).

Infrared absorption spectrum (Liquid film) ν max cm$^{-1}$: 3432, 1698, 1675, 1479, 1454, 1418, 1367.

Nuclear magnetic resonance spectrum (270 MHz, CDCl$_3$) δ ppm: 1.46(9H,s), 1.61–1.80(1H,m), 1.92–2.30(2H,m), 2.37–2.47(1H,m), 3.07–3.17(1H,m), 3.30–3. 69(5H,m).

(2) To a solution of the compound (1.30 g) obtained in Referential Example 1-(1) in tetrahydrofuran (13 ml), triethylamine (0.99 ml) and methanesulfonyl chloride (0.55 ml) were successively added in an ice bath, followed by stirring for one hour. Into the reaction mixture, saturated saline solution was poured to terminate the reaction, followed by extraction three times with ethyl acetate. The combined organic layers were washed with saturated saline solution, dried over anhydrous sodium sulfate and then concentrated by evaporation under reduced pressure. Into the residue (1.83 g), N,N-dimethylformamide (20 ml) was poured, to which sodium azide (1.26 g) was added. The resulting mixture was stirred at 80° C. for 1.5 hours. Into the reaction mixture, saturated saline solution was poured to terminate the reaction, followed by extraction three times with diethyl ether. The combined organic layers were washed with saturated saline solution, dried over anhydrous sodium sulfate and then concentrated by evaporation under reduced pressure. The residue was purified by chromatography through a silica gel column (n-hexane/ethyl acetate= 7/3), whereby (3S)-3-azidomethyl-1-tert-butoxycarbonylpyrrolidine (1.39 g) was obtained.

(3) To a solution of the compound (1.23 g) obtained in Referential Example 1-(2) in acetonitrile (13 ml), triphenylphosphine (1.50 g) was added and the resulting mixture was refluxed for one hour. To the reaction mixture, 4-nitrobenzyl chloroformate (1.52 g) and a 1N aqueous sodium hydroxide solution (7 ml) were successively added. After the temperature was allowed to rise to room temperature, the mixture was stirred for 30 minutes. The reaction mixture was diluted with water and then extracted three times with methylene chloride. The combined organic layers were washed with saturated saline solution, dried over anhydrous sodium sulfate and concentrated by evaporation under reduced pressure. The residue was purified by chromatography through a silica gel column (n-hexane/ethyl acetate=4/6), whereby (3R)-1-tert-butoxycarbonyl-3-(4-nitrobenzyloxycarbonylaminomethyl)pyrrolidine (1.97 g) was obtained.

Optical rotation: $[\alpha]_D^{25}$=−14.3° (C=1.0, CHCl$_3$).

Infrared absorption spectrum (Liquid film) ν max cm$^{-1}$: 3326, 1727, 1683, 1524, 1413, 1348, 1250.

Nuclear magnetic resonance spectrum (270 MHz, CDCl$_3$) δ ppm: 1.45(9H,s), 1.55–1.66(1H,m), 1.92–2.03(1H,m), 2.35–2.45(1H,m), 2.95–3.55(6H,m), 5.18(1H,br.s), 5.20 (2H,s), 7.51(2H,d,J=8.6Hz), 8.22(2H,d,J=8.6Hz).

(4) To a solution (20 ml) of the compound (1.90 g) obtained in Referential Example 1-(3) in methylene chloride, trifluoroacetic acid (3.9 ml) was added in an ice bath. After the temperature of the reaction mixture was allowed to rise to room temperature, the mixture was stirred for 2 hours. The reaction mixture was diluted with methylene chloride, followed by extraction three times with water. Into the combined water layers, a 1N aqueous sodium hydroxide solution (60 ml) was poured to make the solution alkaline. The mixture was extracted three times with methylene chloride. The combined organic layers were washed with saturated saline solution, dried over anhydrous sodium sulfate and concentrated by evaporation under reduced pressure, whereby (3S)-3-(4-nitrobenzyloxycarbonylaminomethyl)pyrrolidine (1.38 g) was obtained as the crude product.

(5) To a solution of (2S,4S)-4-(4-methoxybenzylthio)-1-methyl-2-pyrrolidinecarboxylic acid (0.69 g) in tetrahydrofuran (7 ml), N,N-diisopropylethylamine (0.43 ml) and pivaloyl chloride (0.30 ml) were added in an ice bath. The resulting mixture was stirred at 0° C. for 10 minutes. To the reaction mixture, a solution of a mixture of the compound (0.68 g) obtained in Referential Example 1-(4) and N,N-diisopropylethylamine (0.43 ml) in acetonitrile (8 ml) was added and the resulting mixture was stirred at 0° C. for 30 minutes. Into the reaction mixture, saturated saline solution was poured to terminate the reaction, followed by extraction three times with ethyl acetate. The combined organic layers were washed with saturated saline solution, dried over anhydrous sodium sulfate and concentrated by evaporation under reduced pressure. The residue was purified by chromatography through a silica gel column (ethyl acetate/methanol=7/3), whereby (2S,4S)-4-(4-methoxybenzylthio)-1-methyl-2-[(3R)-3-(4-nitrobenzyloxycarbonylaminomethyl)pyrrolidin-1-ylcarbonyl]pyrrolidine (0.73 g) was obtained.

Infrared absorption spectrum (Liquid film) ν max cm$^{-1}$: 1722, 1639, 1610, 1585, 1513, 1445, 1373, 1347, 1322, 1302, 1247, 1177, 1144, 1109.

Nuclear magnetic resonance spectrum (270 MHz, CDCl$_3$) δ ppm: 1.50–2.62(5H,m), 2.29,2.3 1(3H,sx2), 3.02–3.83 (10H,m), 3.69,3.70(2H,sx2), 3.79(3H,s), 4.98–5.18(1H,m), 5.19(2H,s), 6.83(2H,d,J=6.6Hz), 7.21(2H1d,J=6.6Hz), 7.50 (2H,d,J=8.6Hz), 8.22(2H,d,J=8.6Hz).

(6) To a solution of the compound (0.65 g) obtained in Referential Example 1-(5) in a mixture of anisole (0.65 ml) and trifluoroacetic acid (6.5 ml), trifluoromethanesulfonic acid (0.27 ml) was added while stirring in an ice bath. After the temperature of the reaction mixture was allowed to rise to room temperature, the mixture was stirred for one hour. Trifluoroacetic acid was distilled off under reduced pressure and the residue was washed with n-hexane and diethyl ether to remove anisole. Ethyl acetate was added to the residue. The resulting mixture was washed with a saturated aqueous solution of sodium bicarbonate and saturated saline solution, dried over anhydrous sodium sulfate and then concentrated by evaporation under reduced pressure, whereby the title compound (0.54 g) was obtained.

Another Method for Synthesis of the Title Compound (7) In anhydrous pyridine (100 ml), (3R)-1-tert-butoxycarbonyl-3-pyrrolidinole (10.0 g) was dissolved. To the resulting solution, dimethylaminopyridine (652 mg) and p-toluenesulfonyl chloride (15.3 g) was added in an ice bath, followed by stirring for 48 hours in an ice bath. The solvent was removed under reduced pressure. The residue was dissolved in methylene chloride (200 ml), followed by washing with water. After the water layer was extracted twice with methylene chloride, all the organic layers were washed with saturated saline solution. The organic layers were dried over anhydrous magnesium sulfate and subjected to concentration by evaporation under reduced pressure, whereby 24.2 g of the crude product were obtained. The resulting crude product was purified by chromatography through a silica gel column (eluent: methylene chloride/acetonitrile=40/1), whereby (3R)-1-tert-butoxycarbonyl-3-p-toluenesulfonyloxypyrrolidine (16.8 g) was obtained.

Nuclear magnetic resonance spectrum (270 MHz, CDCl$_3$) δ ppm: 1.43(9H,s), 2.25–1.90(2H,m), 2.46(3H,s), 3.60–3.30 (4H,m), 5.05(1H,m), 7.35(2H,d,J=7.9Hz), 7.79(2H,d,J=7.9Hz).

(8) The compound (12.2 g) obtained in (7) was dissolved in anhydrous acetonitrile (122 ml). To the solution, 1,8-diazabicyclo[5,4,0]-7-undecene (8.02 ml) and acetone cyanohydrin (6.53 ml) were added, followed by heating under reflux for 10 hours. The reaction mixture was diluted with ethyl acetate (1 liter) and washed five times with water (200 ml) and once with a saturated aqueous solution of ammonium chloride (200 ml). The organic layer was dried over anhydrous magnesium sulfate and concentrated by evaporation under reduced pressure, whereby the crude product (9.10 g) was obtained. The resulting crude product was purified by column chromatography (eluent: benzene/ethyl acetate=17/1), whereby (3R)-1-tert-butoxycarbonyl-3-cyanopyrrolidine (4.41 g) was obtained.

Nuclear magnetic resonance spectrum (270 MHz, CDCl$_3$) δ ppm: 1.47(9H,s),2.35–2.15(2H,m),3. 15–3.00(1H,m), 3.75–3.35(4H,m).

(9) In anhydrous tetrahydrofuran (21 ml), the compound (2.10 g) obtained in (8) was dissolved. To the solution, lithium aluminum hydride (2.03 g) was added in an ice bath, followed by stirring in an ice bath for 20 minutes and at room temperature for 50 minutes. To the reaction mixture, tetrahydrofuran (40 ml) and water (4.6 ml) were added and the resulting mixture was stirred at room temperature for 10 minutes. The solvent was removed under reduced pressure. To the residue, methylene chloride (250 ml) and anhydrous sodium sulfate (24 g) were added and the resulting mixture was stirred at room temperature for one hour. After filtration, the solvent was distilled off under reduced pressure. The residue was purified by chromatography through a silica gel column (eluent: ethyl acetate/methanol=1:1), whereby (3R)-3-aminomethyl-1-tertbutoxycarbonylpyrrolidine (703 mg) was obtained.

Nuclear magnetic resonance spectrum (270 MHz, CDCl$_3$) δ ppm: 1.30–1.50(2H,br.s), 1.46(9H,s), 1.50–1.65(1H,m), 1.90–2.10(1H,m), 2.15–2.30(1H,m), 2.65–2.80(2H,m), 2.90–3.10(1H,m), 3.20–3.60(3H,m).

(10) In anhydrous acetonitrile (5.5 ml), the compound (550 mg) obtained in (9) was dissolved. To the solution, diisopropylethylamine (0.575 ml) and p-nitrobenzyl chloroformate (711 mg) were added in an ice bath, followed by stirring for 5 minutes in an ice bath. The solvent was removed under reduced pressure. The residue was dissolved in methylene chloride (50 ml) and the resulting solution was washed with water. The water layer was extracted twice with methylene chloride. All the organic layers were washed with saturated saline solution. The organic layers were dried over anhydrous sodium sulfate. The solvent was distilled off under reduced pressure. The residue was then purified by chromatography through a silica gel column (eluent: benzene/acetonitrile=8/1), whereby (3R)-1-tert-butoxycarbonyl-3-(4-nitrobenzyloxycarbonylaminomethyl) pyrrolidine (599 mg) was obtained. The resulting product coincided completely with that obtained in (3) in data of optical rotation, infrared absorption spectrum and nuclear magnetic resonance spectrum.

REFERENCE EXAMPLE 2

(2S,4S)-4-Mercapto-1-methyl-2-[(3S)-3-(4-nitrobenzyloxycarbonylaminomethyl)pyrrolidin-1-ylcarbonyl]pyrrolidine (1) To a solution (250 ml) of (3R)-3-hydroxymethyl-1-[(1R)-1-phenylethyl]pyrrolidine (12.6 g) in ethanol, a palladium hydroxide-carbon catalyst (12.5 g) was added. The resulting mixture was allowed to absorb hydrogen for 5 hours while stirring at an external temperature of 40° C. The catalyst was filtered off, followed by concentration by evaporation under reduced pressure. Into the residue (7.08 g), acetonitrile (70 ml) was poured, to which di-tert-butylcarbonate (16 ml) was added in an ice bath. After the temperature of the reaction mixture was allowed to rise back to room temperature, the reaction mixture was stirred for one hour. The reaction mixture was treated in a similar manner to that described in Referential Example 1-(1), whereby (3R)-1-tert-butoxycarbonyl-3-hydroxymethylpyrrolidine (10.6 g) was obtained.

Optical rotation: $[\alpha]_D^{25}$=+16.7° (C=1.0, CHCl$_3$).

Infrared absorption spectrum (Liquid film) ν max cm$^{-1}$: 3434, 1698, 1675, 1479, 1454, 1418, 1367.

Nuclear magnetic resonance spectrum (270 MHz, CDCl$_3$) δ ppm: 1.46(9H,s), 1.61–1.80(2H,m), 1.92–2.30(1H,m), 2.37–2.47(1H,m), 3.07–3.17(1H,m), 3.30–3.69(5H,m).

(2) To a solution of the compound (1.55 g) obtained in Referential Example 2-(1) in tetrahydrofuran (16 ml), triethylamine (1.18 ml) and methanesulfonyl chloride (0.66 ml) were successively added in an ice bath, followed by stirring for one hour. Into the reaction mixture, saturated saline solution was poured to terminate the reaction. The resulting mixture was extracted three times with ethyl acetate. The combined organic layers were washed with saturated saline solution, dried over anhydrous sodium sulfate and concentrated by evaporation under reduced pressure. Into the residue (2.19 g), N,N-dimethylformamide (20 ml) was poured, followed by the addition of sodium azide (1.50 g). The mixture was stirred at 80° C. for 1.5 hours. The reaction mixture was treated in a similar manner to that described in Referential Example 1-(2), whereby (3R)-3-azidomethyl-1-tert-butoxycarbonylpyrrolidine (1.43 g) was obtained.

(3) To a solution of the compound (1.00 g) obtained in Referential Example 2-(2) in acetonitrile (10 ml), triphenylphosphine (1.22 g) was added and the resulting mixture was refluxed for one hour. To the reaction mixture, 4-nitrobenzyl chloroformate (1.24 g) and a 1N aqueous sodium hydroxide solution (6 ml) were successively added in an ice bath. After the temperature was allowed to rise to room temperature, the mixture was stirred for 30 minutes. The reaction mixture was treated in a similar manner to that described in Referential Example 1-(3), whereby (3S)-1-tertbutoxycarbonyl-3-(4-nitrobenzyloxycarbonylaminomethyl)pyrrolidine (1.51 g) was obtained.

Optical rotation: $[\alpha]_D^{25}$=+14.5° (C=1.0, CHCl$_3$).

Infrared absorption spectrum (Liquid film) ν max cm$^{-1}$: 3325, 1726, 1682, 1524, 1414, 1348, 1249.

Nuclear magnetic resonance spectrum (270 MHz, CDCl$_3$) δ ppm: 1.45(9H,s), 1.55–1.66(1H,m), 1.92–2.03(1H,m), 2.35–2.45(1H,m), 2.95–3.55(6H,m), 5.06(1H,br.s), 5.19 (2H,s), 7.51(2H,d,J=8.6Hz), 8.22(2H,d,J=8.6Hz).

(4) To a solution of the compound (1.51 g) obtained in Referential Example 2-(3) in methylene chloride (17 ml), trifluoroacetic acid (3.1 ml) was added in an ice bath. After the temperature of the reaction mixture was allowed to rise to room temperature, the mixture was stirred for two hours. The reaction mixture was treated in a similar manner to that described in Referential Example 1-(4), (3R)-3-(4-nitrobenzyloxycarbonylaminomethyl)pyrrolidine (1.16 g) was obtained as a crude product.

Nuclear magnetic resonance spectrum (270 MHz, CDCl$_3$) δ ppm: 1.42–1.60(1H,m), 1.90–2.07(1H,m), 2.27–2.50(1H, m), 2.52–3.28(7H,m), 5.13–5.3(1H,m), 5.19(2H,s), 7.51 (2H,d,J=8.6Hz), 8.22(2H,d,J=8.6Hz).

(5) To a solution of (2S,4S)-4-(4-methoxybenzylthio) 1-methyl-2-pyrrolidinecarboxylic acid (0.70 g) in tetrahydrofuran (7 ml), N,N-diisopropylethylamine (0.43 ml) and pivaloyl chloride (0.31 ml) were added in an ice bath. The resulting mixture was stirred at 0° C. for 10 minutes. To the reaction mixture, a solution of a mixture of the compound (0.70 g) obtained in Referential Example 2-(4) and N,N-diisopropylethylamine (0.43 ml) in acetonitrile (8 ml) was added, followed by stirring at 0° C. for 30 minutes. The reaction mixture was treated in a similar manner to that described in Referential Example 1-(5), whereby (2S,4S)-4-(4-methoxybenzylthio)-1-methyl-2-[(3S)-3-(4-nitrobenzyloxycarbonylaminomethyl)pyrrolidin-1-ylcarbonyl]pyrrolidine (0.75 g) was obtained.

Infrared absorption spectrum (Liquid film) ν max cm$^{-1}$: 1722, 1639, 1610, 1585, 1513, 1445, 1347, 1302, 1248, 1176, 1144, 1120, 1109.

Nuclear magnetic resonance spectrum (270 MHz, CDCl$_3$) δ ppm: 1.52–2.61(5H,m), 2.30(3H,s), 3.03–3.78(10H,m), 3.70(2H,s), 3.79,3.80(3H,sx2), 5.04–5.05(1H,m), 5.19(2H, s), 6.83,6.84(2H,dx2,J=8.6Hz), 7.20,7.22(2H,d 2,J=8.6Hz), 7.51 (2H,dxJ=8.6Hz), 8.22(2H,d,J=8.6Hz).

(6) To a solution of the compound (0.67 g) obtained in Referential Example 2-(5) in a mixture of anisole (0.67 ml) and trifluoroacetic acid (6.7 ml), trifluoromethanesulfonic acid (0.27 ml) was added while stirring in an ice bath. The temperature of the reaction mixture was allowed to rise to room temperature, followed by stirring for one hour. The reaction mixture was treated in a similar manner to that described in Referential Example 1-(6), whereby the title compound (0.57 g) was obtained.

REFERENCE EXAMPLE 3

(2S,4S)-4-Mercapto-2-[(3S)-3-(N-methyl-N-(4-nitrobenzyloxycarbonyl)aminomethyl)pyrrolidin-1-ylcarbonyl]-1-(4-nitrobenzyloxycarbonyl)pyrrolidine (1) To a solution of the compound (0.82 g) obtained in Referential Example 1-(1) in tetrahydrofuran (8 ml), triethylamine (0.62 ml) and methanesulfonyl chloride (0.35 ml) were successively added. The resulting mixture was stirred for one hour. Into the reaction mixture, saturated saline solution was poured to terminate the reaction, followed by extraction three times with ethyl acetate. The combined organic layers were washed with saturated saline solution, dried over anhydrous sodium sulfate and then concentrated by evaporation under reduced pressure.

To the residue (1 16 g), a 40% methylamine-methanol solution (18 ml) was added and the mixture was heated in a pressure bottle at 100° C. for 4 hours. After the temperature of the reaction mixture was allowed to lower to room temperature, the mixture was concentrated by evaporation under reduced pressure. To a solution of the residue (1.32 g) in acetonitrile (15 ml), N,N-diisopropylethylamine (1.4 ml) and 4-nitrobenzyl chloroformate (1.73 g) were added in an ice bath, followed by stirring at 0° C. for 2 hours. Saturated saline solution was poured into the reaction mixture to terminate the reaction and the resulting mixture was extracted three times with ethyl acetate. The combined organic layers were washed with saturated saline solution, dried over anhydrous sodium sulfate and concentrated by evaporation under reduced pressure. The residue was purified by chromatography through a silica gel column (n-hexane/ethyl acetate=4/6–3/7), whereby (3R)-1-tert-butoxycarbonyl-3-[N-methyl-N-(4-nitrobenzyloxycarbonyl)aminomethyl]pyrrolidine (1.42 g) was obtained.

Optical rotation: $[\alpha]_D^{25}$=–6.9° (C=1.0, CHCl$_3$).

Infrared absorption spectrum (Liquid film) ν max cm$^{-1}$: 1696, 1608, 1524, 1480, 1455, 1404, 1366, 1347, 1293, 1255, 1211, 1191, 1170, 1152, 1125.

Nuclear magnetic resonance spectrum (270 MHz, CDCl$_3$) δ ppm: 1.45(9H,s), 1.56–1.68(1H,m), 1.89–2.01(1H,m), 2.45–2.55(1H,m), 2.98(3H,s), 2.98–3.10(1H,m), 3.27–3.57 (5H,m), 5.23(2H,s), 7.51(2H,d,J=8.6Hz), 8.23(2H,d,J=8.6Hz).

(2) To a solution of the compound (1.96 g) obtained in Referential Example 3-(1) in methylene chloride (25 ml), trifluoroacetic acid (3.8 ml) was added in an ice bath, followed by stirring at room temperature for 2 hours. The reaction mixture was treated in a similar manner to that described in Referential Example 1-(4), whereby (3S)-3-[N-methyl-N-(4-nitrobenzyloxycarbonyl)aminomethyl] pyrrolidine (1.55 g) was obtained.

Nuclear magnetic resonance spectrum (270 MHz, CDCl$_3$) δ ppm: 1.30–1.51(1H,m), 1.81–1.97(1H,m), 2.20–2.69(3H, m), 2.85–3.06(6H,m), 3.20–3.35(2H,m), 5.22(2H,s), 7.51 (2H,d,J=8.6Hz), 8.22(2H,d,J=8.6Hz).

(3) To a solution of (2S,4S)-4-(4-methoxybenzylthio)-1-(4-nitrobenzyloxycarbonyl)-2-pyrrolidinecarboxylic acid (1.52 g) in tetrahydrofuran (15 ml), N,N-diisopropylethylamine (0.59 ml) and pivaloyl chloride (0.42 ml) were added in an ice bath. The resulting mixture was stirred at 0° C. for 10 minutes. To the reaction mixture, a solution of a mixture of the compound (1.00 g) obtained in Referential Example 3-(2) and N,N-diisopropylethylamine (0.59 ml) in acetonitrile (15 ml) was added and the resulting mixture was stirred at 0° C. for 30 minutes. The reaction mixture was treated in a similar manner to that described in Referential Example 1-(5), whereby (2S,4S)-4-(4-methoxybenzylthio)-2-[(3S)-3-(N-methyl-N-(4-nitrobenzyloxycarbonyl)aminomethyl)pyrrolidin-1-ylcarbonyl]-1-(4-nitrobenzyloxycarbonyl)pyrrolidine (2.08 g) was obtained.

Infrared absorption spectrum (KBr) ν max cm$^{-1}$: 1706, 1654, 1608, 1585, 1520, 1439, 1403, 1346, 1299, 1249, 1210, 1194, 1175, 1149, 1110.

Nuclear magnetic resonance spectrum (270 MHz, CDCl$_3$) δ ppm: 1.50–2.70(5H,m), 2.92–4.08(12H,m), 3.74(2H,s), 3.80,3.81(3H,sx2), 4.22–4.45(1H,m), 4.98–5.33(4H,m), 6.87(2H,d,J=8.6Hz), 7.22–7.56(6H,m), 8.20–8.30(4H,m).

(4) To a solution of the compound (2.03 g) obtained in Referential Example 3-(3) in a mixture of anisole (2.0 ml) and trifluoroacetic acid (20 ml), trifluoromethanesulfonic acid (0.62 ml) was added while stirring in an ice bath. The resulting mixture was then stirred at room temperature for one hour. The reaction mixture was treated in a similar manner to that described in Referential Example 1-(6), whereby the title compound (1.92 g) was obtained.

Another Method for a Synthesis of the Title Compound (5) To a solution of (2S,4R)-4-hydroxy-1-(4-nitrobenzyloxycarbonyl)proline (4.65 g) in anhydrous dimethylformamide (60 ml), (3S)-3-[N-methyl-N-(4-nitrobenzyloxycarbonyl)aminomethyl]pyrrolidine hydrochloride (4.95 g), diisopropylethylamine (5.23 ml), 1-ethyl-3-(3-dimethylaminopropyl)carbodiimide hydrochloride (4.03 g) and 1-hydroxybenzotriazole (2.23 g) were added. The resulting mixture was stirred at room temperature for 10 hours. The reaction mixture was concentrated by evaporation under reduced pressure. The residue was dissolved in ethyl acetate. The resulting solution was washed with water and the organic layer was dried over anhydrous sodium sulfate. The solvent was distilled off and the residue was subjected to chromatography through a silica gel column. From the fractions eluted with ethyl acetate/methanol= 9/1, (2S,4R)-4-hydroxy-2-[(3S)-3-[N-methyl-N-(4-nitrobenzyloxycarbonyl)aminomethyl]pyrrolidin-1-ylcarbonyl]-1-(4-nitrobenzyloxycarbonyl)pyrrolidine (8.70 g) was obtained as a powder.

Infrared absorption spectrum (KBr) ν max cm$^{-1}$: 3402, 1706, 1654, 1607, 1522, 1436, 1346.

Nuclear magnetic resonance spectrum (400 MHz, DMSO-d$_6$) δ ppm: 1.30–2.20(3H, m), 2.30–2.60(1H, m), 2.80–3.00(3H, m), 3.00–3.80(10H, m), 4.20–4.40(1H, m), 4.40–4.60(11, m), 5.00–5.30(4H, m), 7.50–7.70(41, m), 8.10–8.30(4H, m).

(6) The compound (8.70 g) obtained in (5) was dissolved in anhydrous acetonitrile (87 ml). To the solution, triethylamine (2.72 ml) and methanesulfonyl chloride (1.34 ml) were added in an ice bath, followed by stirring at the same temperature for 5 minutes. The reaction mixture was concentrated by evaporation under reduced pressure. The residue was dissolved in ethyl acetate. The resulting solution was washed successively with water and saturated saline solution and then dried over anhydrous sodium sulfate. The residue was subjected to chromatography through a silica gel column. From the fractions eluted with ethyl acetate/ methanol=18/1–14/1, (2S,4R)-4-methanesulfonyloxy-2-[(3S)-3-[N-methyl-N-(4-nitrobenzyloxycarbonyl) aminomethyl]pyrrolidin-1-ylcarbonyl]-1-(4-nitrobenzyloxycarbonyl)pyrrolidine (9.33 g) was obtained.

Infrared absorption spectrum (KBr) ν max cm$^{-1}$: 1706, 1652, 1607, 1522, 1441, 1405, 1347.

Nuclear magnetic resonance spectrum (400 MHz, DMSO-d$_6$) δ ppm: 1.50–2.20(3H, m), 2.30–2.80(3H, m), 2.90–3.05(3H, m), 3.08(3H, s), 3.10–3.70(6H, m), 3.80–4.10(2H, m), 4.50–4.70(1H, m), 5.20–5.40(4H, m), 7.40–7.55(4H, m), 8.15–8.25(4H, m).

(7) The compound (2.00 g) obtained in (6) was dissolved in anhydrous dimethylformamide (25 ml). To the solution, potassium thioacetate (520 mg) was added and the resulting mixture was stirred at 75° C. for 1.5 hours. After cooling to room temperature, the reaction mixture was diluted with ethyl acetate, washed with water and saturated saline solution and then dried over anhydrous sodium sulfate. The residue was subjected to chromatography through a silica gel column. From the fractions eluted with ethyl acetate/methanol=100/1, (2S,4S)-4-acetylthio-2-[(3S)-3-[N-methyl-N-(4-nitrobenzyloxycarbonyl)aminomethyl]pyrrolidin-1-ylcarbonyl]-1-(4-nitrobenzyloxycarbonyl)pyrrolidine (1.60 g) was obtained.

Infrared absorption spectrum (KBr) ν max cm$^{-1}$: 1705, 1654, 1607, 1522, 1437, 1404, 1346.

Nuclear magnetic resonance spectrum (400 MHz, DMSO-d$_6$) δ ppm: 1.70–2.10(3H, m), 2.34(3H, s), 2.40–2.70(2H, m), 2.90–3.10(3H, m), 3.10–3.70(6H, m), 3.80–4.10(2H, m), 4.11(1H, t, J=9.1Hz), 4.40–4.60(1H, m), 5.00–5.40(4H, m), 7.40–7.60(4H, m), 8.15–8.30(4H, m).

(8) The compound (1.48 g) obtained in (7) was dissolved in methanol (30 ml) and methylene chloride (4.4 ml). To the resulting solution, a 1N sodium methoxide solution in methanol (2.3 ml) was added in an ice bath, followed by stirring at the same temperature for 10 minutes. To the reaction mixture, 1N hydrochloric acid (2.4 ml) was added and the resulting mixture was concentrated by evaporation under reduced pressure. The residue was dissolved in ethyl acetate. The resulting solution was washed successively with water and saturated saline solution and dried over anhydrous sodium sulfate. The solvent was distilled off under reduced pressure, whereby the title compound (1.34 g) was obtained as a powder. The resulting compound coincided with that obtained in (4) in infrared absorption spectrum and nuclear magnetic resonance spectrum.

REFERENTIAL EXAMPLE 4

(2S,4S)-4-Mercapto-1-methyl-2-[(3S)-3-(N-methyl-N-(4-nitrobenzyloxycarbonyl)aminomethyl)pyrrolidin-1-ylcarbonyl]pyrrolidine (1) A solution of (2S,4S)-4-(4-methoxybenzylthio)-1-methyl-2-pyrrolidinecarboxylic acid (0.49 g) in tetrahydrofuran (5 ml), N,N-diisopropylethylamine (0.30 ml) and pivaloyl chloride (0.21 ml) were added in an ice bath. The resulting mixture was stirred at 0° C. for 10 minutes. To the reaction mixture, a solution of a mixture of the compound (0.46 g) obtained in Referential Example 3-(2) and N,N-diisopropylethylamine (0.30 ml) in acetonitrile (10 ml) was added and the resulting mixture was stirred at 0° C. for 30 minutes. Saturated saline solution was poured into the reaction mixture to terminate the reaction, followed by extraction three times with ethyl acetate. The combined organic layers were washed with saturated saline solution, dried over anhydrous sodium sulfate and then concentrated by evaporation under reduced pressure. The residue was purified by chromatography through a silica gel column (ethyl acetate/methanol=6/4), whereby (2S,4S)-4-(4-methoxybenzylthio)- -methyl-2-[(3S)-3-(N-methyl-N-(4-nitrobenzyloxycarbonyl)aminomethyl)pyrrolidin-1-ylcarbonyl]pyrrolidine (0.76 g) was obtained.

Infrared absorption spectrum (Liquid film) ν max cm$^{-1}$: 1734, 1705, 1646, 1609, 1585, 1513, 1440, 1403, 1373, 1346, 1301, 1248, 1212, 1191, 1149, 1107.

Nuclear magnetic resonance spectrum (270 MHz, CDCl$_3$) δ ppm: 1.55–2.18(2H,m), 2.35,2.37(3H,sx2), 2.41–2.70(3H, m), 3.04,3.06(3H,sx2), 3.10–3.88(10H,m), 3.75(2H,s), 3.85 (3H,s), 5.27(2H,s), 6.89(2H,d,J=8.6Hz), 7.27(2H,d,J=7.9Hz), 7.57(2H,d,J=8.6Hz), 8.28(2H,d,J=7.9Hz).

(2) To a solution of the compound (0.64 g) obtained in Referential Example 4-(1) in a mixture of anisole (0.65 ml) and trifluoroacetic acid (6.5 ml), trifluoromethanesulfonic acid (0.26 ml) was added while stirring in an ice bath, followed by stirring at room temperature for one hour. The reaction mixture was treated in a similar manner to that described in Referential Example 1-(6), whereby the title compound (0.54 g) was obtained.

REFERENTIAL EXAMPLE 5

(2S,4S)-4-Mercapto-2-[(3R)-3-(N-methyl-N-(4-nitrobenzyloxycarbonyl)aminomethyl)pyrrolidin-1-ylcarbonyl]-1-(4-nitrobenzyloxycarbonyl)pyrrolidine (1) To a solution of the compound (1.17 g), which had been obtained in Referential Example 2-(1), in tetrahydrofuran (12 ml), triethylamine (0.89 ml) and methanesulfonyl chloride (0.50 ml) were added successively in an ice bath. The resulting mixture was stirred for one hour. Saturated saline solution was poured into the reaction mixture to terminate the reaction, followed by extraction three times with ethyl acetate. The combined organic layers were washed with saturated saline solution, dried over anhydrous sodium sulfate and concentrated by evaporation under reduced pressure.

To the residue (1.66 g), a 40% methylamine-methanol solution (25 ml) was added and the resulting mixture was heated at 100° C. for 4 hours in a pressure bottle. After the temperature of the reaction mixture was allowed to lower to room temperature, the mixture was concentrated by evaporation under reduced pressure. To a solution of the residue (1.89 g) in acetonitrile (20 ml), N,N-diisopropylethylamine (1.84 ml) and 4-nitrobenzyl chloroformate (2.28 g) were added in an ice bath and the resulting mixture was stirred at 0° C. for 2 hours. The reaction mixture was treated in a similar manner to that described in Referential Example 3(1), whereby (3S)-1-tert-butoxycarbonyl-3-[N-methyl-N-(4-nitrobenzyloxycarbonyl)aminomethyl]pyrolidine (1.92 g) was obtained.

Optical rotation: [α]$_D^{25}$=+7.2° (C=1.0, CHCl$_3$).

Infrared absorption spectrum (Liquid film) ν max cm$^{-1}$: 1696, 1608, 1524, 1480, 1455, 1404, 1366, 1347, 1293, 1255, 1211, 1191, 1170, 1152, 1125.

Nuclear magnetic resonance spectrum (270 MHz, CDCl$_3$) δ ppm: 1.45(9H,s), 1.56–1.68(1H,m), 1.89–2.01(1H,m), 2.45–2.55(1H,m), 2.98(3H,s), 2.98–3.10(1H,m), 3.27–3.57 (5H,m), 5.22(2H,s), 7.51(2H,d,J=8.6Hz), 8.23(2H,d,J=8.6Hz).

(2) To a solution of the compound (0.84 g) obtained in Referential Example 5-(1) in methylene chloride (8 ml), trifluoroacetic acid (1.6 ml) was added in an ice bath. The resulting mixture was stirred at room temperature for 2 hours. The reaction mixture was treated in a similar manner to that described in Referential Example 1-(4), whereby (3R)-3-[N-methyl-N-(4-nitrobenzyloxycarbonyl) aminomethyl]pyrrolidine (0.58 g) was obtained.

Nuclear magnetic resonance spectrum (270 MHz, CDCl$_3$) δ ppm: 1.30–1.51(1H,m), 1.81–1.97(1H,m), 2.20–2.69(3H, m), 2.85–3.06(6H,m), 3.20–3.35(2H,m), 5.22(2H,s), 7.51 (2H,d,J=8.6Hz), 8.22(2H,d,J=8.6Hz).

(3) To a solution of (2S,4S)-4-(4-methoxybenzylthio)-1-(4-nitrobenzyloxycarbonyl)-2-pyrrolidinecarboxylic acid (0.92 g) in tetrahydrofuran (10 ml), N,N-diisopropylethylamine (0.36 ml) and pivaloyl chloride (0.25 ml) were added in an ice bath, followed by stirring at 0° C. for 10 minutes. To the reaction mixture, a solution of a mixture of the compound (0.55 g) obtained in Referential Example 5-(2) and N,N-diisopropylethylamine (0.36 ml) in acetonitrile (10 ml) was added and the resulting mixture was stirred at 0° C. for 30 minutes. The reaction mixture was treated in a similar manner to that described in Referential Example 1-(5), whereby (2S,4S)-4-(4-methoxybenzylthio)-2-[(3R)-3-(N-methyl-N-(4-nitrobenzyloxycarbonyl)aminomethyl)pyrrolidin-1-ylcarbonyl]-1-(4-nitrobenzyloxycarbonyl)pyrrolidine (1.00 g) was obtained.

Infrared absorption spectrum (KBr) ν max cm$^{-1}$: 1706, 1654, 1608, 1585, 1520, 1438, 1403, 1346, 1299, 1249, 1210, 1194, 1175, 1148, 1109.

Nuclear magnetic resonance spectrum (270 MHz, CDCl$_3$) δ ppm: 1.50–2.68(5H,m), 2.92–4.08(9H,m), 2.97(3H,s), 3.73(2H,s), 3.79,3.80(3H,sx2), 4.30–4.46(1H,m), 4.97–5.35(4H,m), 6.85(2H,d,J=8.6Hz), 7.24(2H,d,J=8.6Hz), 7.46(2H,d,J=8.6Hz), 7.51(2H,d,J=8.6Hz), 8.23(4H,d,J=8.6Hz).

(4) To a solution of the compound (0.99 g) obtained in Referential Example 5-(3) in a mixture of anisole (1.0 ml) and trifluoroacetic acid (10 ml), trifluoromethanesulfonic acid (0.30 ml) was added in an ice bath. The resulting mixture was stirred at room temperature for one hour. The reaction mixture was treated in a similar manner to that described in Referential Example 1-(6), whereby the title compound (0.90 g) was obtained.

REFERENTIAL EXAMPLE 6

(2S,4S)-4-Mercapto- -methyl-2-[(3R)-3-(N-methyl-N-(4-nitrobenzyloxycarbonyl)aminomethyl)pyrrolidin-1-ylcarbonyl]pyrrolidine (1) To a solution of (2S,4S)-4-(4-methoxybenzylthio)-1-methyl-2-pyrrolidinecarboxylic acid (0.50 g) in tetrahydrofuran (5 ml), N,N-diisopropylethylamine (0.31 ml) and pivaloyl chloride (0.22 ml) were added in an ice bath. The resulting mixture was stirred at 0° C. for 10 minutes. To the reaction mixture, a solution of a mixture of the compound (0.47 g) obtained in Referential Example 5-(2) and N,N-diisopropylethylamine (0.31 ml) in acetonitrile (10 ml) was added, followed by stirring at 0° C. for 30 minutes. The reaction mixture was treated in a similar manner to that described in Referential Example 4-(1), whereby (2S,4S)-4-(4-methoxybenzylthio)-1-methyl-2-[(3R)-3-(N-methyl-N-(4-nitrobenzyloxycarbonyl)aminomethyl)pyrrolidin-1-ylcarbonyl]pyrrolidine (0.67 g) was obtained.

Infrared absorption spectrum (Liquid film) ν max cm$^{-1}$: 1705, 1647, 1609, 1585, 1512, 1440, 1403, 1346, 1301, 1248, 1212, 1191, 1149, 1107.

Nuclear magnetic resonance spectrum (270 MHz, CDCl$_3$) δ ppm: 1.50–2.12(2H,m), 2.29,2.32(3H,sx2), 2.37–2.66(3H,m), 3.00,3.02(3H,sx2), 3.00–3.88(10H,m), 3.72(2H,s), 3.81(3H,s), 5.23(2H,s), 6.85(2H,d,J=8.6Hz), 7.23(2H,d,J=8.6Hz), 7.53(2H,d,J=8.6Hz), 8.24(2H,d,J=8.6Hz).

(2) To a solution of the compound (0.59 g), which had been obtained in Referential Example 6-(1), in a mixture of anisole (0.6 ml) and trifluoroacetic acid (6.0 ml), trifluoromethanesulfonic acid (0.24 ml) was added while stirring in an ice bath. The resulting mixture was stirred at room temperature for one hour. The reaction mixture was treated in a similar manner to that described in Referential Example 1-(6), whereby the title compound (0.53 g) was obtained.

REFERENTIAL EXAMPLE 7

(2S,4S)-4-Mercapto-1-(4-nitrobenzyloxycarbonyl)-2-[(3R)-3-(4-nitrobenzyloxycarbonylguanidinomethyl)pyrrolidin-1-ylcarbonyl]pyrrolidine (1) To a solution of the compound (1.50 g) obtained in Referential Example 1-(2) in acetonitrile (15 ml), triphenylphosphine (1.83 g) was added and the resulting mixture was refluxed for one hour. To the reaction mixture, sodium sulfate hydrate (2.24 g) was added, followed by reflux for a further one hour. After the temperature was allowed to lower to room temperature, the insoluble material was filtered off. The filtrate was then concentrated by evaporation under reduced pressure. Diethyl ether was poured into the residue and insoluble material so precipitated was filtered off. The filtrate was concentrated by evaporation under reduced pressure.

To a solution of the residue (1.90 g) in ethanol (20 ml), 1H-pyrazole-1-carboxamidine hydrochloride (1.02 g) was added and the resulting mixture was refluxed for 3 hours. After the temperature of the reaction mixture was allowed to lower to room temperature, the mixture was concentrated by evaporation under reduced pressure. The residue was washed with diethyl ether.

To a solution of the residue (2.86 g) in a tetrahydrofuran (25 ml)—water (25 ml) mixture, 4-nitrobenzyl chloroformate (3.57 g) and a 1N aqueous sodium hydroxide solution (33 ml) were added successively in an ice bath, followed by stirring at 0° C. for 30 minutes. The reaction mixture was diluted with water, followed by extraction three times with methylene chloride. The combined organic layers were washed with saturated saline solution, dried over anhydrous sodium sulfate and concentrated by evaporation under reduced pressure. The residue so obtained was purified by chromatography through a silica gel column (ethyl acetate/methanol=9/1), whereby (3R)-1-tert-butoxycarbonyl-3-(4-nitrobenzyloxycarbonylguanidinomethyl)pyrrolidine (1.29 g) was obtained.

Infrared absorption spectrum (KBr) ν max cm$^{-1}$: 3393, 3327, 1693, 1652, 1641, 1604, 1523, 1408, 1347, 1289.

Nuclear magnetic resonance spectrum (270 MHz, CDCl$_3$) δ ppm: 1.44(9H,s), 1.68–1.52(1H,m), 1.95–2.04(1H,m), 2.36–2.48(1H,m), 3.03(1H,dd,J=11.2,7.2Hz), 3.15–3.54(5H,m), 5.19(2H,s), 6.72(2H,br.s), 7.54(2H,d,J=8.6Hz), 8.20(2H,d,J=8.6Hz).

(2) To a solution of the compound (1.23 g) obtained in Referential Example 7-(1) in methylene chloride (13 ml), trifluoroacetic acid (2.2 ml) was added in an ice bath. The resulting mixture was stirred at room temperature for 5 hours. The reaction mixture was treated in a similar manner to that described in Referential Example 1-(4), whereby (3S)-3-(4-nitrobenzyloxycarbonylguanidinomethyl)pyrrolidine (0.72 g) was obtained.

(3) To a solution of (2S,4S)-4-(4-methoxybenzylthio)-1-(4-nitrobenzyloxycarbonyl)-2-pyrrolidinecarboxylic acid (1.05 g) in tetrahydrofuran (10 ml), N,N-diisopropylethylamine (0.41 ml) and pivaloyl chloride (0.29 ml) were added in an ice bath. The resulting mixture was stirred at 0° C. for 10 minutes. To the reaction mixture, a solution of a mixture of the compound (0.72 g) obtained in Referential Example 7-(2) and N,N-diisopropylethylamine (0.41 ml) in acetonitrile (10 ml) was added, followed by stirring at 0° C. for 30 minutes. Into the reaction mixture, saturated saline solution was poured to terminate the reaction, followed by extraction three times with ethyl acetate. The combined organic layers were washed with saturated saline solution, dried over anhydrous sodium sulfate and concentrated by evaporation under reduced pressure. The residue so obtained was purified by chromatography through a silica gel column (ethyl acetate/methanol=9/1), whereby (2S,4S)-4-(4-methoxybenzylthio)-1-(4-nitrobenzyloxycarbonyl)-2-[(3R)-3-(4-nitrobenzyloxycarbonylguanidinomethyl)pyrrolidin-1-ylcarbonyl]pyrrolidine (0.93 g) was obtained.

Infrared absorption spectrum (KBr) ν max cm$^{-1}$: 1707, 1651, 1609, 1521, 1432, 1405, 1346, 1319, 1287, 1251, 1207, 1174, 1110.

Nuclear magnetic resonance spectrum (270 MHz, CDCl$_3$) δ ppm: 1.55–2.71(5H,m), 2.96–4.40(10H,m), 3.72,3.74(2H,sx2), 3.79(3H,s), 4.97–5.38(4H,m), 6.81–6.88(2H,m), 7.20–7.25(2H,m), 7.39–7.56(4H,m), 7.99–8.25(4H,m).

(4) To a solution of the compound (0.88 g) obtained in Referential Example 7-(3) in a mixture of anisole (1.4 ml) and trifluoroacetic acid (14 ml) trifluoromethanesulfonic acid (0.31 ml) was added while stirring in an ice bath. The resulting mixture was stirred at room temperature for one hour. The reaction mixture was treated in a similar manner to that described in Referential Example 1-(6), whereby the title compound (1.28 g) was obtained.

REFERENTIAL EXAMPLE 8

(2S,4S)-4-Mercapto-1-(4-nitrobenzyloxycarbonyl)-2-[(3R)-3-(4-nitrobenzyloxycarbonylacetimidoylaminomethyl)pyrrolidin-1-ylcarbonyl]pyrrolidine (1) To a solution of the compound (1.00 g) obtained in Referential Example 1-(2) in acetonitrile (10 ml), triphenylphosphine (1.22 g) was added. The resulting mixture was refluxed for one hour. Sodium sulfate decahydrate (1.50 g) was added to the reaction mixture, followed by reflux for further one hour. After the temperature was allowed to rise to room temperature, insoluble material was filtered off. The filtrate was concentrated by evaporation under reduced pressure. Diethyl ether was poured into the residue. Insoluble material so precipitated was filtered off and the filtrate was concentrated by evaporation under reduced pressure.

To a solution of the residue (1.27 g) in acetonitrile (25 ml), a 4N hydrogen chloride—ethyl acetate solution (1.1 ml) was added in an ice bath, followed by stirring at 0° C. for 15 minutes. To the reaction mixture, N-(4-nitrobenzyloxycarbonyl)acetamidine (1.15 g) was added in an ice bath and the resulting mixture was stirred at 50° C. for 1.5 hours. After the temperature of the reaction mixture was allowed to lower to room temperature, it was diluted with ethyl acetate. The diluted solution was washed with a saturated aqueous solution of sodium bicarbonate and saturated saline solution, dried over anhydrous sodium sulfate and concentrated by evaporation under reduced pressure. The residue so obtained was purified by chromatography through a silica gel column, whereby (3R)-1-tert-butoxycarbonyl-3-[N-(4-nitrobenzyloxycarbonyl)acetimidoylaminomethyl)pyrrolidine (1.66 g) was obtained.

Infrared absorption spectrum (Liquid film) ν max cm$^{-1}$: 3313, 3112, 1687, 1564, 1523, 1411, 1346, 1220.

Nuclear magnetic resonance spectrum (270 MHz, CDCl$_3$) δ ppm: 1.46(9H,s), 1.58–1.72(1H,m), 1.95–2.12(1H,m), 2.16,2.25(3H,sx2), 2.39–2.53(1H,m), 3.00–3.11 (1H,m), 3.28–3.62(5H,m), 5.20,5.23(2H,sx2), 7.57(2H,d,J=8.6Hz), 8.21 (2H,d,J=8.6Hz).

(2) To a solution of the compound (1.66 g) obtained in Referential Example 8-(1) in methylene chloride (17 ml), trifluoroacetic acid (2.9 ml) was added in an ice bath. The resulting mixture was stirred at room temperature for 2 hours. The reaction mixture was treated in a similar manner to that described in Referential Example 1-(4), whereby (3S)-3-[N-(4-nitrobenzyloxycarbonyl)acetimidoylaminomethyl]pyrrolidine (0.81 g) was obtained.

(3) To a solution of (2S,4S)-4-(4-methoxybenzylthio)-1-(4-nitrobenzyloxycarbonyl)-2-pyrrolidinecarboxic acid (1.18 g) in tetrahydrofuran (12 ml), N,N-diisopropylethylamine (0.46 ml) and pivaloyl chloride (0.33 ml) were added in an ice bath. The resulting mixture was stirred at 0° C. for 10 minutes. To the reaction mixture, a solution of a mixture of the compound (0.81 g), obtained in Referential Example 8-(2) and N,N-diisopropylethylamine (0.46 ml) in acetonitrile (10 ml) was added, followed by stirring at 0° C. for 30 minutes. Saturated saline solution was poured into the reaction mixture to terminate the reaction, followed by extraction three times with ethyl acetate. The combined organic layers were washed with saturated saline solution, dried over anhydrous sodium sulfate and concentrated by evaporation under reduced pressure. The residue so obtained was purified by chromatography through a silica gel column (ethyl acetate/methanol=95/5–9/1), whereby (2S,4S)-4-(4-methoxybenzylthio)-1-(4-nitrobenzyloxycarbonyl)-2-[(3R)-3-(N-(4-nitrobenzyloxycarbonyl)acetimidoylaminomethyl)pyrrolidin-1-ylcarbonyl]pyrrolidine (1.05 g) was obtained.

Infrared absorption spectrum (KBr) ν max cm$^{-1}$: 3300, 31113, 3080, 1709, 1651, 1608, 1585, 1564, 1520, 1439, 1404, 1346, 1301, 1241, 1213, 1176, 1110.

Nuclear magnetic resonance spectrum (270 MHz, CDCl$_3$) δ ppm: 1.49–2.77(8H,m), 3.03–4.12(10H,m), 3.79(2H,s), 3.84(3H,s), 4.30–4.50(1H,m), 5.04–5.40(4H,m), 6.90(2H,d, J=8.6Hz), 7.29(2H,d,J=8.6Hz), 7.43–7.65(4H,m), 8.16–8.32 (4H,m).

(4) To a solution of the compound (1.02 g) obtained in Referential Example 8-(3) in a mixture of anisole (1.5 ml) and trifluoroacetic acid (15 ml), trifluoromethanesulfonic acid (0.36 ml) was added while stirring in an ice bath. The resulting mixture was stirred at room temperature for one hour. The reaction mixture was treated in a similar manner to that described in Referential Example 1-(6), whereby the title compound (1.35 g) was obtained.

REFERENTIAL EXAMPLE 9

(2S,4S)-2-[(3S)-3-(N-cyclopropyl-N-(4-nitrobenzyloxycarbonyl)aminomethyl)pyrrolidin-1-ylcarbonyl]-4-mercapto-1-(4-nitrobenzyloxycarbonyl]pyrrolidine (1) To a solution of the compound (1.00 g) obtained in Referential Example 1-(1) in tetrahydrofuran (10 ml), triethylamine (0.83 ml) and methanesulfonyl chloride (0.46 ml) were successively added in an ice bath. The resulting mixture was stirred for one hour. Saturated saline solution was poured into the reaction mixture to terminate the reaction, followed by extraction three times with ethyl acetate. The combined organic layers were washed with saturated saline solution, dried over anhydrous sodium sulfate and concentrated by evaporation under reduced pressure.

To a solution of the residue (1.53 g) in methanol (10 ml), cyclopropylamine (10 ml) was added and the resulting mixture was heated at 100° C. for 4 hours in a pressure bottle. After the temperature of the reaction mixture was allowed to lower to room temperature, the mixture was concentrated by evaporation under reduced pressure. To a solution of the residue (1.93 g) in acetonitrile (20 ml), N,N-diisopropylethylamine (0.95 ml) and 4-nitrobenzyl chloroformate (I.18 g) were added in an ice bath and the resulting mixture was stirred at room temperature for 2 hours. Saturated saline solution was poured into the reaction mixture to terminate the reaction, followed by extraction three times with ethyl acetate. The combined organic layers were washed with saturated saline solution, dried over anhydrous sodium sulfate and concentrated by evaporation under reduced pressure. The residue so obtained was purified by chromatography through a silica gel column (n-hexane/ethyl acetate=4/6), whereby (3S)-1-tertbutoxycarbonyl-3-[N-cyclopropyl-N-(4-nitrobenzyloxycarbonyl)aminomethyl]-pyrrolidine (0.95 g) was obtained.

Infrared absorption spectrum (Liquid film) ν max cm$^{-1}$: 1697, 1607, 1524, 1494, 1479, 1453, 1405, 1366, 1346, 1288, 1258, 1210, 1171, 1141, 11111.

Nuclear magnetic resonance spectrum (270 MHz, CDCl$_3$) δ ppm: 0.63–0.71(2H,m), 0.78–0.87(2H,m), 1.45(9H,s), 1.55–1.68(1H,m), 1.90–2.00(1H,m), 2.50–2.67(2H,m), 2.96–3.09(1H,m), 3.18–3.59(5H,m), 5.23(2H,s), 7.53(2H,d, J=8.6Hz), 8.23(2H,d,J=8.6Hz).

(2) To a solution of the compound (0.77 g) obtained in Referential Example 9-(1) in methylene chloride (12 ml), trifluoroacetic acid (1.4 ml) was added in an ice bath, followed by stirring at room temperature for 3 hours. The reaction mixture was treated in a similar manner to that described in Referential Example 1-(4), whereby (3S)-3-[N-cyclopropyl-N-(4-nitrobenzyloxycarbonyl)aminomethyl] pyrrolidine (0.72 g) was obtained.

(3) To a solution of (2S,4S)-4-(4-methoxybenzylthio)-1-(4-nitrobenzyloxycarbonyl)-2-pyrrolidinecarboxylic acid (1.00 g) in tetrahydrofuran (10 ml), N,N-diisopropylethylamine (0.39 ml) and pivaloyl chloride (0.28 ml) were added in an ice bath. The resulting mixture was stirred at 0° C. for 10 minutes. To the reaction mixture, a solution of a mixture of the compound (0.72 g), obtained in Referential Example 9-(2) and N,N-diisopropylethylamine (0.39 ml) in acetonitrile (10 ml) was added, followed by stirring at 0° C. for 30 minutes. Saturated saline solution was poured into the reaction mixture to terminate the reaction, followed by extraction three times with ethyl acetate. The combined organic layer was washed with saturated saline solution, dried over anhydrous sodium sulfate and concentrated by evaporation under reduced pressure. The residue was purified by chromatography through a silica gel column (ethyl acetate), whereby (2S,4S)-2-[(3S)-3-(N-cyclopropyl-N-(4-nitrobenzyloxycarbonyl)aminomethyl)pyrrolidin-1-ylcarbonyl]-4-(4-methoxybenzylthio)-1-(4-nitrobenzyloxycarbonyl)pyrrolidine (0.93 g) was obtained.

Infrared absorption spectrum (KBr) ν max cm$^{-1}$: 1707, 1655, 1609, 1585, 1521, 1440, 1404, 1346, 1289, 1250, 1210, 1176, 1139, 1110.

Nuclear magnetic resonance spectrum (270 MHz, CDCl$_3$) δ ppm: 0.50–0.75(2H,m), 0.75–0.95(2H,m), 1.47–2.02(3H, m), 2.32–2.74(3H,m), 2.92–4.08(9H,m), 3.73(2H,s), 3.79, 3.80(3H,sx2), 4.26–4.45(1H,m), 4.97–5.34(4H,m), 6.85 (2H,d,J=8.6Hz), 7.23,7.25(2H,d2,J=8.6Hz), 7.46,7.53(4H, dx2,J=8.6Hz), 8.23(4H,d,J=8.6Hz).

(4) To a solution of the compound (0.82 g) obtained in Referential Example 9-(3) in a mixture of anisole (0.8 ml) and trifluoroacetic acid (8 ml), trifluoromethanesulfonic acid (0.24 ml) was added while stirring in an ice bath, followed by stirring at room temperature for one hour. The reaction mixture was treated in a similar manner to that described in Referential Example 1-(6), whereby the title compound (0.77 g) was obtained.

REFERENTIAL EXAMPLE 10

(2S,4S)-4-Mercapto-1-(4-nitrobenzyloxycarbonyl)-2-[(3S)-3-(4-nitrobenzyloxycarbonylacetimidoylaminomethyl) pyrrolidin-1-ylcarbonyl]pyrrolidine.

(1) To a solution of the compound (1.00 g) obtained in Referential Example 2-(2) in acetonitrile (10 ml), triphenylphosphine (1.22 g) was added and the resulting mixture was refluxed for one hour. To the reaction mixture, sodium sulfate decahydrate (1.50 g) was added, followed by reflux for further one hour. After the temperature of the reaction mixture was allowed to lower to room temperature, insoluble material was filtered off. The filtrate was then concentrated by evaporation under reduced pressure. Into the residue, diethyl ether was poured and insoluble material so precipitated was filtered off. The filtrate was then concentrated by evaporation under reduced pressure.

To a solution of the residue (1.33 g) in acetonitrile (25 ml), a 4N hydrogen chloride—ethyl acetate solution (1.1 ml) was added in an ice bath and the resulting mixture was stirred at 0° C. for 15 minutes. To the reaction mixture, N-(4-nitrobenzyloxycarbonyl)acetamidine (1.15 g) was added in an ice bath. The resulting mixture was stirred at 50° C. for 1.5 hours. The reaction mixture was treated in a similar manner to that described in Referential Example 8-(1), whereby (3S)-1-tertbutoxycarbonyl-3-[(N-4-nitrobenzyloxycarbonyl)acetimidoylaminomethyl] pyrrolidine (1.58 g) was obtained.

Infrared absorption spectrum (Liquid film) ν max cm$^{-1}$: 3314, 3112, 1690, 1565, 1523, 1409, 1346, 1221.

Nuclear magnetic resonance spectrum (270 MHz, CDCl$_3$) δ ppm: 1.46(9H,s), 1.58–1.72(1H,m), 1.95–2.12(1H,m), 2.16,2.25(3H,sx2), 2.39–2.53(1H,m), 3.00–3.11(1H,m), 3.28(5H,m), 5.20,5.23(2H,sx2), 7.57(2H,d,J=8.6Hz), 8.21 (2H,d,J=8.6Hz).

(2) To a solution of the compound (1.58 g) obtained in Referential Example 10-(1) in methylene chloride (15 ml), trifluoroacetic acid (2.9 ml) was added in an ice bath. The resulting mixture was stirred at room temperature for 2 hours. The reaction mixture was treated in a similar manner to that described in Referential Example 1-(4), whereby (3R)-3-[N-(4-nitrobenzyloxycarbonyl) acetimidoylaminomethyl]pyrrolidine (0.97 g) was obtained.

(3) To a solution of (2S,4S)-4-(4-methoxybenzylthio)-1-(4-nitrobenzyloxycarbonyl)-2-pyrrolidinecarboxylic acid (1.06 g) in tetrahydrofuran (10 ml), N,N-diisopropylethylamine (0.41 ml) and pivaloyl chloride (0.29 ml) were added in an ice bath. The resulting mixture was stirred at 0° C. for 10 minutes. To the reaction mixture, a solution of a mixture of the compound (0.76 g) obtained in Referential Example 10-(2) and N,N-diisopropylethylamine (0.41 ml) in acetonitrile (10 ml) was added, followed by stirring at 0° C. for 30 minutes. The reaction mixture was treated in a similar manner to that described in Referential Example 8-(3), whereby (2S,4S)-4-(4-methoxybenzylthio)-1-(4-nitrobenzyloxycarbonyl)-2-[(3S)-3-(N-(4-nitrobenzyloxycarbonyl)acetimidoylaminomethyl) pyrrolidin-1-ylcarbonyl]pyrrolidine (1.00 g) was obtained.

Infrared absorption spectrum (KBr) ν max cm$^{-1}$: 3296, 3113, 3080, 1708, 1680, 1652, 1608, 1584, 1564, 1521, 1432, 1405, 1346, 1301, 1239, 1216, 1176, 1110.

Nuclear magnetic resonance spectrum (270 MHz, CDCl$_3$) δ ppm: 1.60–1.80(8H,m), 3.02–4.10(9H,m), 3.78(2H,s), 3.83(3H, s), 4.32–4.52(1H,m), 5.02–5.38(4H,m), 6.90(2H, d,J=8.6Hz), 7.28(2F,d,J=8.6Hz), 7.45–7.69(4H,m), 8.20–8.34(4H,m).

(4) To a solution of the compound (1.00 g) obtained in Referential Example 10-(3) in a mixture of anisole (1 ml) and trifluoroacetic acid (10 ml), trifluoromethanesulfonic acid (0.20 ml) was added while stirring in an ice bath. The resulting mixture was stirred at room temperature for two hours. The reaction mixture was treated in a similar manner to that described in Referential Example 1-(6), whereby the title compound (0.93 g) was obtained.

REFERENTIAL EXAMPLE 11

(2S,4S)-4-Mercapto-1-(4-nitrobenzyloxycarbonyl)-2-[(3S)-3-(4-nitrobenzyloxycarbonylguanidinomethyl)pyrrolidin-1-ylcarbonyl]pyrrolidine (1) To a solution of the compound (1.01 g) obtained in Referential Example 2-(2) in anhydrous acetonitrile (10 ml), triphenylphosphine (1.23 g) was added and the resulting mixture was refluxed for one hour. To the reaction mixture, 1.51 g of sodium sulfate decahydrate were added, followed by reflux for further one hour. After cooling to room temperature, the reaction mixture was filtered. The filtrate was then concentrated by evaporation under reduced pressure. The residue was purified by chromatography through a silica gel column (ethyl acetate/methanol=1/1), whereby (3S)-3-aminomethyl-1-tert-butoxycarbonylpyrrolidine (840 mg) was obtained. The product completely coincided with the compound obtained in Referential Example 1-(9) in HPLC and NMR data.

(2) To a solution of the compound (840 mg) obtained in (1) in ethanol (14 ml), 1H-pyrazole-1-carboxamidine hydrochloride (686 mg) was added and the resulting mixture was refluxed for 3 hours. After the temperature of the reaction mixture was allowed to lower to room temperature, the mixture was concentrated by evaporation under reduced pressure. The residue was washed with diisopropyl ether.

To a solution of the residue (1.50 g) in a tetrahydrofuran (20 ml)—water (20 ml) mixture, 4-nitrobenzyl chloroformate (2.41 g) and a 1N aqueous sodium hydroxide solution (22 ml) were successively added and the resulting mixture was stirred at 0° C. for 30 minutes. The reaction mixture was diluted with water, followed by extraction three times with ethyl acetate. The combined organic layers were washed with saturated saline solution, dried over anhydrous sodium sulfate and concentrated by evaporation under reduced pressure. The residue so obtained was purified by chromatography through a silica gel column (ethyl acetate/methanol=25/1), whereby (3S)-1-tertbutoxycarbonyl-3-(4-nitrobenzyloxycarbonylguanidinomethyl)pyrrolidine (746 mg) was obtained.

Nuclear magnetic resonance spectrum (270 MHz, $CDCl_3$) δ ppm: 1.44(9H,s), 1.68–1.52(1H,m), 1.95–2.04(1H,m), 2.36–2.48(1H,m), 3.03(1H,dd,J=11.1,7.1Hz), 3.15–3.54 (5H,m), 5.19(2H,s), 6.70(1H,br.s), 7.54(2H,d,J=8.6Hz), 8.20(2H,d,J=8.6Hz).

(3) To a solution of the compound (701 mg) obtained in (2) in ethyl acetate (7 ml), a 4N hydrochloric acid ethyl acetate solution (3.3 ml) was added and the resulting mixture was stirred at room temperature for one hour. The reaction mixture was concentrated. The residue was then washed with ethyl ether, whereby (3S)-3-(4-nitrobenzyloxycarbonylguanidinomethyl)pyrrolidine hydrochloride (647 mg) was obtained.

(4) To (2S,4S)-4-(4-methoxybenzylthio)-1-(4-nitrobenzyloxycarbonyl)-2-pyrrolidinecarboxylic acid (947 ml) in N,N-dimethylformamide (10 ml), N,N-diisopropylethylamine (0.369 ml), the compound obtained in (3) (647 mg), 1-ethyl-3-(3-dimethylaminopropyl) carbodiimide hydrochloride (406 mg) and 1-hydroxybenzotriazole (286 mg) were added and the resulting mixture was stirred overnight at room temperature. Ethyl acetate was added to the reaction mixture. The resulting mixture was washed with water and saturated saline solution, dried over anhydrous sodium sulfate and then concentrated by evaporation under reduced pressure. The residue so obtained was separated by chromatography through a silica gel column (ethyl acetate/methanol=12/1), whereby (2S,4S)-4-(4-methoxybenzylthio)-1-(4-nitrobenzyloxycarbonyl)-2-[(3S)-3-(4-nitrobenzyloxycarbonylguanidinomethyl)pyrolidin-1-ylcarbonyl]pyrrolidine (I.13 g) was obtained.

Infrared absorption spectrum (KBr) ν max $cm^{-1}$: 1708, 1520, 1251, 1032, 739.

Nuclear magnetic resonance spectrum (270 MHz, $CDCl_3$) δ ppm: 1.5–2.7(5H,m), 2.9–3.6(10H,m), 3.71,3.73(2H,sx2), 3.77(3H,s), 3.80–3 .90(1H,m), 4.95–5.25(4H,m), 6.87(2H, d,J=8.45Hz), 7.25–7.28(2H,m), 7.45–7.65(4H,m), 8.15–8.3 (4H,m).

(5) To a solution of the compound (1.10 g) obtained in (4) in a mixture of anisole (1.65 ml) and trifluoroacetic acid (8.0 ml), trifluoromethanesulfonic acid (0.26 ml) was added while stirring in an ice bath. The resulting mixture was stirred at the same temperature for 30 minutes. The reaction mixture was treated as in Referential Example 1-(6), whereby the title compound (926 mg) was obtained.

REFERENTIAL EXAMPLE 12

(2S,4S)-4-Mercapto-1-(4-nitrobenzyloxycarbonyl)-2-[(3R)-3-(pyrrolidin-1-ylmethyl)pyrrolidin-1-ylcarbonyl]pyrrolidine (1) To a solution of (3S)-3-(pyrrolidin-1-ylmethyl) pyrrolidine hydrochloride (367 mg), which had been prepared from (3R)-1-tert-butoxycarbonyl-3-hydroxymethylpyrrolidine, in anhydrous dimethylformamide (10 ml), (2S,4S)-4-(4-methoxybenzylthio)-1-(4-nitrobenzyloxycarbonyl)-2-pyrrolidinecarboxylic acid (804 mg), diisopropylethylamine (1.16 ml), 1-hydroxybenzotriazole (243 mg) and 1-ethyl-3-(3-dimethylaminopropyl)carbodiimide hydrochloride (483 mg) were added. The resulting mixture was stirred at room temperature for 10 hours. The solvent was then distilled off under reduced pressure. The residue was dissolved in ethyl acetate. The resulting solution was washed with a saturated aqueous solution of sodium bicarbonate. The organic layer was dried over anhydrous sodium sulfate and then concentrated by evaporation under reduced pressure. The residue was purified by chromatography through a silica gel column (ethyl acetate/methanol=5/1–1/1), whereby (2S,4S)-4-(4-methoxybenzylthio)-2-[(3R)-3-(pyrrolidin-1-ylmethyl) pyrrolidin-1-ylcarbonyl]-1-(4-nitrobenzyloxycarbonyl) pyrrolidine (362 mg) was obtained.

Nuclear magnetic resonance spectrum (270 MHz, $CDCl_3$) δ ppm: 1.00–2.00(3H, m), 2.00–3.00(2H, m), 3.00–4.20 (171, m), 3.73(2H, s), 3.79(31, s), 4.32–4.46(1H, m), 4.90–5.40(2H, m), 6.85(2H, d, J=8.5 Hz), 7.24(21, d, J=8.5 Hz), 7.46(2H, d, J=8.6 Hz), 8.23(2H, d, J=8.6 Hz).

(2) To a solution of the compound (362 mg) obtained in (1) in a mixture of anisole (0.68 ml) and trifluoroacetic acid (3.4 ml), trifluoromethanesulfonic acid (0.14 ml) was added while stirring in an ice bath. The resulting mixture was stirred at the same temperature for 30 minutes. Trifluoroacetic acid was distilled off under reduced pressure. The residue was washed with hexane and ether, dried under reduced pressure, extracted with ethyl acetate after addition of a saturated aqueous solution of sodium bicarbonate and then washed with saturated saline solution. The organic layer was dried over anhydrous sodium sulfate and concentrated by evaporation under reduced pressure, whereby the title compound (287 mg) was obtained as a powder.

Infrared absorption spectrum (KBr) ν max $cm^{-1}$: 1697, 1525, 1246.

REFERENTIAL EXAMPLE 13

(2S,4S)-2-[(3R)-3-(N-2-Hydroxyethyl-N-4-nitrobenzyloxycarbonylaminomethyl)pyrrolidin-1-ylcarbonyl]-4-mercapto-1-(4-nitrobenzyloxycarbonyl)-pyrrolidine (3S)-3-(N-2-Hydroxyethyl-N-4-nitrobenzyloxycarbonylaminomethyl)pyrrolidine hydrochloride (197 mg) was treated in a similar manner to that described in Referential Example 12-(1) and (2), to afford the title compound (214 mg) as a powder.

Nuclear magnetic resonance spectrum (270 MHz, $CDCl_3$) δ ppm: 1.50–2.20(2H, m), 2.50–2.90(2H, m), 2.90–4.10 (12H, m), 4.15–4.30(2H, m), 4.40–4.55(1H, m), 5.20–5.30 (4H, m), 7.50–7.60(4H, m), 8.19–8.28(4H, m).

REFERENTIAL EXAMPLE 14

(2S,4S)-2-[(3S)-3-(N-carbamoylmethyl-N-4-nitrobenzyloxycarbonylaminomethyl)pyrrolidin-1-ylcarbonyl1–4-mercapto-1-(4-nitrobenzyloxycarbonyl)pyrrolidine (3S)-3-(N-Carbamoylmethyl-N-4-nitrobenzyloxycarbonylaminomethyl)pyrrolidine hydrochloride (261 mg) was treated in a similar manner to that described in Referential Example 12-(1) and (2), to give the title compound (368 mg) as a powder.

Infrared absorption spectrum (KBr) ν max $cm^{-1}$: 3371, 2948, 2879, 1706, 1645, 1608, 1522, 1347, 1259.

Nuclear magnetic resonance spectrum (400 MHz, DMSO-$d_6$) δ ppm: 1.40–2.05(2H, m), 2.30–2.75(3H, m), 2.90–3.60(5H, m), 3.60–4.95(4H, m), 4.30–4.60(1H, m), 5.00–5.30(4H, m), 7.40–7.70(4H, m), 8.10–8.30(4H, m).

REFERENTIAL EXAMPLE 15

(2S,4S)-4-Mercapto-1-(4-nitrobenzyloxycarbonyl)-2-[(3S)-3-[N-2-(4-nitrobenzyloxycarbonylamino)ethyl-N-4-nitrobenzyloxycarbonylaminomethyl]-pyrrolidin-1-ylcarbonyl]pyrrolidine (3S)-3-[N-2-(4-nitrobenzyloxycarbonylamino)ethyl)-N-4-nitrobenzyloxycarbonylaminomethyl]pyrrolidine hydrochloride (195 mg) was treated in a similar manner to that described in Referential Example 12-(1) and (2) to give the title compound (248 mg) as a powder.

Infrared absorption spectrum (KBr) ν max $cm^{-1}$: 1705, 1648, 1607, 1521, 1437, 1347.

Nuclear magnetic resonance spectrum (270 MHz, $CDCl_3$+$CD_3OD$) δ ppm: 1.50–2.10(3H, m), 2.60–2.80(2H, m), 3.00–3.70(1H, m), 3.80–4.00(1H, m), 4.00–4.20(1H, m), 4.40–4.60(1H, m), 5.15–5.30(6H, m), 7.45–7.60(6H, m), 8.10–8.30(6H, m).

REFERENTIAL EXAMPLE 16

(2S,4S)-2-[(3S)-3-(N-2-Dimethylaminoethyl-N-4-nitrobenzyloxycarbonylaminomethyl)pyrrolidin-1-ylcarbonyl]-4-mercapto-1-(4-nitrobenzyloxycarbonyl)pyrrolidine (3S)-3-(N-2-Dimethylaminoethyl-N-4-nitrobenzyloxycarbonylaminomethyl)pyrrolidine dihydrochloride (302 mg) was treated in a similar manner to that described in Referential Example 12-(1) and (2), to afford the title compound (461 mg) as a powder.

REFERENTIAL EXAMPLE 17

(2S,4S)-4-Mercapto-2-[(3R)-3-[N-2-(N-methyl-N-4-nitrobenzyloxycarbonylamino)ethyl-N-methylaminomethyl]pyrrolidin-1-ylcarbonyl]-1-(4-nitrobenzyloxycarbonyl)pyrrolidine (3S)-3-[N-2-(N-Methyl-N-4-nitrobenzyloxycarbonylamino)ethyl-N-methylaminomethyl]pyrrolidine dihydrochloride (580 mg) was treated in a similar manner to that described in Referential Example 12-(1) and (2), to give the title compound (628 mg) as a powder.

Infrared absorption spectrum (KBr) ν max $cm^{-1}$: 1699, 1645, 1523, 1442, 1347.

Nuclear magnetic resonance spectrum (270 MHz, DMSO-$d_6$) δ ppm: 1.40–2.00(3H, m), 2.00–4.10(21H, m), 4.30–4.60(1H, m), 5.00–5.30(4H, m), 7.51–7.65(4H, m), 8.21–8.28(4H, m).

REFERENTIAL EXAMPLE 18

(2S,4S)-2-[(3S)-3-(N-2-Fluoroethyl-N-4-nitrobenzyloxycarbonlaminomethyl)pyrrolidin-1-ylcarbonyl]-4-mercapto-1-(4-nitrobenzyloxycarbonyl)pyrrolidine (3S)-3-(N-2-Fluoroethyl-N-4-nitrobenzyloxycarbonylaminomethyl)pyrrolidine hydrochloride is treated in a similar manner to that described in Referential Example 12-(1) and (2), to afford the title compound.

REFERENTIAL EXAMPLE 19

(2S,4S)-4-Mercapto-2-[(3R)-3-[1-methyl-2,3-bis(4-nitrobenzyloxycarbonyl)guanidinomethyl]pyrrolidin-1-ylcarbonyl]-1-(4-nitrobenzyloxycarbonyl)pyrrolidine (3S)-3-[1-Methyl-2,3-bis(4-nitrobenzyloxycarbonyl)guanidinomethyl]-pyrrolidine hydrochloride (1.20 g) was treated in a similar manner to that described in Referential Example 12-(1) and (2), to give the title compound (996 mg).

Infrared absorption spectrum (KBr) ν max $cm^{-1}$: 1754, 1709, 1645, 1608, 1521, 1441, 1405, 1347.

Nuclear magnetic resonance spectrum (270 MHz, DMSO-$d_6$) δ ppm: 1.50–2.00(2H, m), 2.60–2.80(1H, m), 2.90–3.05(4H, m), 3.10–3.60(7H, m), 3.65–3.80(2H, m), 3.80–4.05(1H, m), 4.30–4.60(1H, m), 5.00–5.30(6H, m), 7.45–7.70(6H, m), 8.05–8.30(6H, m).

REFERENTIAL EXAMPLE 20

(2S,4S)-4-Mercapto-1-(4-nitrobenzyloxycarbonyl)-2-[(3R)-3-(N-4-nitrobenzyloxycarbonylacetiethylaminomethyl)pyrrolidin-1-ylcarbonyl]pyrrolidine (3S)-3-(N-4-Nitrobenzyloxycarbonylacetimidoyl-N-methylaminomethyl)pyrrolidine hydrochloride is treated in a similar manner to that described in Referential Example 12-(1) and (2), to afford the title compound.

REFERENTIAL EXAMPLE 21

(2S,4S)-4-Mercapto-1-(4-nitrobenzyloxycarbonyl)-2-[(3R)-3-(N-4-nitrobenzyloxycarbonylformimidoyl-N-methylaminomethyl)pyrrolidin-1-ylcarbonyl]pyrrolidine (3S)-3-(N-4-Nitrobenzyloxycarbonylformimidoyl-N-methylaminomethyl)pyrrolidine hydrochloride is treated in a similar manner to that described in Referential Example 12-(1) and (2), to give the title compound.

REFERENTIAL EXAMPLE 22

(2S,4S)-4-Mercapto-1-(4-nitrobenzyloxycarbonyl)-2-[(3S)-3-(N-2,2,2-trifluoroethyl-N-4-nitrobenzyloxycarbonylaminomethyl)pyrrolidin-1-ylcarbonyl]pyrrolidine (3S)-3-(N-2,2,2-Trifluoroethyl-N-4-nitrobenzyloxycarbonylaminomethyl)pyrrolidine hydrochloride is treated in a similar manner to that described in Referential Example 12-(1) and (2), to afford the title compound.

REFERENTIAL EXAMPLE 23

(2S,4S)-4-Mercapto-1-(4-nitrobenzyloxycarbonyl)-2-[(3R)-3-(4-nitrobenzyloxycarbonylformimidoylaminomethyl)pyrrolidin-1-ylcarbonyl]pyrrolidine (3S)-3-(4-Nitrobenzyloxycarbonylformimidoylmethylaminomethyl)pyrrolidine hydrochloride is treated in a similar manner to that described in Referential Example 12-(1) and (2), to afford the title compound.

REFERENTIAL EXAMPLE 24

(2S,4S)-2-[(3S)-3-[2, 3-Bis(4-nitrobenzyloxycarbonyl)guanidinomethyl]pyrrolidin-1-ylcarbonyl]-4-mercapto-1-methylpyrrolidine (3S)-3-[2,3-bis(4-Nitrobenzyloxycarbonyl)guanidinomethyl]pyrrolidine is treated in a similar manner to that described in Referential Example 4-(1) and (2), to give the title compound.

REFERENTIAL EXAMPLE 25

(2S,4S)-4-Mercapto-1-methyl-2-[(3S)-3-(4-nitrobenzyloxycarbonylacetimidoylaminomethyl)pyrrolidin 1-ylcarbonyl]pyrrolidine (3S)-3-(4-Nitrobenzyloxycarbonylacetimidoylaminomethyl)pyrrolidine is treated in a similar manner to that described in Referential Example 4-(1) and (2), to afford the title compound.

REFERENTIAL EXAMPLE 26

(2S,4S)-4-Mercapto-1-ethylaminomethyl)pyrrolidin-1-ylcarbonyl]pyrrolidine (3S)-3-(4-Nitrobenzyloxycarbonylformimidoylaminomethyl)pyrrolidine is treated in a similar manner to that described in Referential Example 4-(1) and (2), to give the title compound.

REFERENTIAL EXAMPLE 27

(2S,4S)-2-[(3R)-3-[1-Methyl-2,3 bis(4-nitrobenzyloxycarbonyl)guanidinomethyl]-4-mercapto-1-methylpyrrolidin-1-ylcarbonyl]pyrrolidine (3S)-3-[ -Methyl-2,3-bis(4-Nitrobenzyloxycarbonyl)guanidinomethyl]- pyrrolidine is treated in a similar manner to that described in Referential Example 12-(1) and (2), to afford the title compound.

REFERENTIAL EXAMPLE 28

(2S,4S)-4-Mercapto-1-methyl-2-[(3S)-3-(N-4-nitrobenzyloxycarbonylacetimidoyl-N-methylaminomethyl)pyrrolidin-1-ylcarbonyl]pyrrolidine (3S)-3-(N-4-Nitrobenzyloxycarbonylacetimidoyl-N-methylaminomethyl)pyrrolidine is treated in a similar manner to that described in Referential Example 4-(1) and (2), to afford the title compound.

REFERENTIAL EXAMPLE 29

(2S,4S)-4-Mercapto-1-methyl-2-[(3R)-3-(N-4-nitrobenzyloxycarbonylformimidoyl-N-methylaminomethyl)pyrrolidin-1-ylcarbonyl]pyrrolidine (3S)-3-(N-4-Nitrobenzyloxycarbonylformimidoyl-N-methylaminomethyl)pyrrolidine is treated in a similar manner to that described in Referential Example 4-(1) and (2), to give the title compound.

TEST 1

In Vitro Antibacterial Activity

Antibacterial activity was measured by the agar plate dilution method, whereby the minimum growth inhibitory concentration (MIC: μg/ml) against various pathogenic bacteria was determined. The test results on the antibacterial activity of the compounds of the invention of Examples 3 and 7 against *Staphylococcus aureus* 209P, *Escherichia coli* NIHJ and *Pseudomonas aeruginosa* No. 7 are shown in Table 2.

Incidentally, Compounds A and B used for comparison are compounds of Example 3 in Japanese Patent Application Kokai No. Hei 5-310740 [compounds represented by the formula (I) of the present invention, wherein $R^1$, $R^2$ and $R^3$ represent hydrogen atoms]. Compound A has the R configuration at the binding position of the aminomethyl group. Compound B has the S configuration at the binding position of the aminomethyl group.

TABLE 2

Minimum Growth Inhibitory Concentration (MIC: μg/ml)

| | Bacterial strain tested | | |
|---|---|---|---|
| | *Staphylococcus aureus* 209P | *Escherichia coli* NIHJ | *Pseudomonas aeruginosa* No. 7 |
| Compound of Ex. 3 | 0.02 | 0.02 | 0.05 |
| Compound of Ex. 7 | 0.02 | 0.02 | 0.05 |
| Compound A | 0.02 | 0.02 | 0.1 |
| Compound B | 0.02 | 0.02 | 0.1 |

The medium used for the measurement was Mueller-Hinton II agar (MHA, Becton Dikinson Microbiology Systems).

TEST 2

In Vitro Antibacterial Activity

The antibacterial activities of the compounds of the invention of Examples 3 and 7 and meropenem against *Staphylococcus aureus* 209P, *Escherichia coli* NIHJ and *Pseudomonas aeruginosa* 3719 (strain resistant to meropenem) are shown in Table 3.

TABLE 3

Minimum Growth Inhibitory Concentration (MIC: μg/ml)

| | Bacterial strain tested | | |
|---|---|---|---|
| | *Staphylococcus aureus* 209P | *Escherichia coli* NIHJ | *Pseudomonas aeruginosa* 3719 |
| Compound of Ex. 3 | ≦0.01 | ≦0.01 | 0.2 |
| Compound of Ex. 7 | ≦0.01 | ≦0.01 | 0.1 |
| Meropenem | 0.02 | ≦0.01 | 6.2 |

The medium used for the measurement was Nutrient Agar Eiken (Eiken Chemicals Co., Ltd.).

TEST 3

In Vivo Antibacterial Activity (Treatment for Infections)

The culture of the bacterial strain to be tested was inoculated intraperitoneally to groups of mice (SPF, DDY, male), each group consisting of 7 animals. A solution of the test compound was subcutaneously administered twice in total to the mice, once immediately and once four hours after the inoculation. From the survival ratio five days after infection, the 50% effective dose ($ED_{50}$: mg/kg) was determined by the Probit method and the single dose of test compound was indicated.

The test results of the compound of Example 3, compound A and Meropenem against *Pseudomonas aeruginosa* 1008 are shown in Table 4. Incidentally, Compound A is as described above.

TABLE 4

Treatment against infections ($ED_{50}$: mg/kg)

| | Bacterial strain tested<br>*Pseudomonas aeruginosa* 1008 |
|---|---|
| Compound of Ex. 3 | 0.22 |
| Compound A | 0.44 |
| Meropenem | 0.72 |

The above results indicate that the compounds of the present invention have strong antibacterial activity in the in vitro test and also have excellent effects in the treatment of infections in the in vivo test. Described specifically, compared with the aminomethyl compounds [compounds represented by the formula (I) of the present invention wherein $R^1$, $R^2$ and $R^3$ represent hydrogen atoms; Compounds A and B disclosed in Japanese Patent Application Kokai Hei 5-310740], the compounds of the present invention (e.g. the compound of Example 3) exhibited superior activity against *Pseudomonas aeruginosa*. In addition, the compounds of the present invention exhibited excellent antibacterial activity against *Pseudomonas aeruginosa* 3719 which is resistant to Meropenem.

Furthermore, the compounds of the present invention (e.g. the compound of Example 3) exhibited excellent pharmacokinetic properties such as half-life in blood. When the compounds of the present invention were administered to rabbits, the incorporation in to the renal cortex is relatively low. When the compound of Example 3 was intravenously administered to rabbits at a dose of 200 mg/kg, the rabbits did not exhibit nephrotoxicity.

FORMULATION EXAMPLE 1

Injections

In 5 ml of distilled water for injection, 500 mg of the compound of Example 3 were dissolved. The solution was allowed to pass through a filter for sterilizing the solution, followed by lyophilization to afford a lyophilized preparation for injection.

FORMULATION EXAMPLE 2

Tablets

| Compound of Example 3 | 50 mg |
|---|---|
| Lactose | 126 mg |
| Corn starch | 23 mg |
| Magnesium stearate | 1 mg |
| | 200 mg |

The above ingredients, each in the powdery form, were mixed, subjected to wet granulation with corn starch, dried and then tableted by a tableting machine, whereby tablets, each 200 mg, were prepared. The tablets so obtained can be coated with sugar, if necessary.

We claim:

1. (1R,5S,6S)-6-[(1R)-1-Hydroxyethyl]-1-methyl-2-[(2S,4S)-2-[(3R)-3-methylaminomethylpyrrolidin-1-ylcarbonyl]pyrrolidin-4-ylthio]-1-carbapen-2-em-3-carboxylic acid.

2. A composition for the prevention or treatment of bacterial infections, which comprises an effective amount of the compound of claim 1 in a pharmaceutical carrier.

3. A method for the prevention or treatment of bacterial infections, which comprises administering to a warm-blooded animal a pharmacologically effective amount of the compound of claim 1.

4. (1R,5S,6S)-6-[(1R)-1-Hydroxyethyl]-1-methyl-2-[(2S,4S)-2-[(3R)-3-methylaminomethylpyrrolidin-1-ylcarbonyl]pyrrolidin-4-ylthio]-1-carbapen-2-em-3-carboxylic acid hydrochloride.

5. A composition for the prevention or treatment of bacterial infections, which comprises an effective amount of the compound of claim 4 in a pharmaceutical carrier.

6. A method for the prevention or treatment of bacterial infections, which comprises administering to a warm-blooded animal a pharmacologically effective amount of the compound of claim 4.

7. (1R,5S,6S)-6-[(1R)-1-Hydroxyethyl]-1-methyl-2-[(2S,4S)-2-[(3R)-3-methylaminomethylpyrrolidin-1-ylcarbonyl]pyrrolidin-4-ylthio]-1-carbapen-2-em-3-carboxylic acid or a pharmacologically acceptable salt thereof.

8. A composition for the prevention or treatment of bacterial infections, which comprises an effective amount of the compound or a pharmacologically acceptable salt thereof of claim 7 in a pharmaceutical carrier.

9. A method for the prevention or treatment of bacterial infections, which comprises administering to a warm-blooded animal a pharmacologically effective amount of the compound or a pharmacologically acceptable salt thereof of claim 7.

* * * * *